US012653727B2

(12) United States Patent
Raycheck et al.

(10) Patent No.: US 12,653,727 B2
(45) Date of Patent: Jun. 16, 2026

(54) ABSORBENT ARTICLE WITH WAIST GASKETING ELEMENT AND LEG CUFFS

(71) Applicant: The Procter & Gamble Company, Cincinnati, OH (US)

(72) Inventors: Jeromy Thomas Raycheck, South Lebanon, OH (US); Abhishek Prakash Surushe, Schwalbach am Taunus (DE); Zachary Aaron Freije, Milford, OH (US); Cornelia Beate Martynus, Nidderau-Ostheim (DE); Donald Carroll Roe, West Chester, OH (US); Andrew James Sauer, Cincinnati, OH (US); Christopher Erin Kiger, Union Township, OH (US); Sara Lyn Giovanni, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 386 days.

(21) Appl. No.: 18/133,549

(22) Filed: Apr. 12, 2023

(65) Prior Publication Data

US 2023/0270600 A1     Aug. 31, 2023

Related U.S. Application Data

(63) Continuation of application No. 16/690,841, filed on Nov. 21, 2019, now abandoned, which is a
(Continued)

(51) Int. Cl.
*A61F 13/15*          (2006.01)
*A61F 13/49*          (2006.01)
(Continued)

(52) U.S. Cl.
CPC .... *A61F 13/49011* (2013.01); *A61F 13/4942* (2013.01); *A61F 13/49466* (2013.01);
(Continued)

(58) Field of Classification Search
CPC .............. A61F 13/4901; A61F 13/4942; A61F 13/4946; A61F 13/495; A61F 13/496;
(Continued)

(56) References Cited

U.S. PATENT DOCUMENTS

| 3,848,594 A | 11/1974 | Buell |
| 3,860,003 A | 1/1975 | Buell |

(Continued)

FOREIGN PATENT DOCUMENTS

| CA | 2922316 A1 | 3/2015 |
| CN | 1047970 A | 12/1990 |

(Continued)

OTHER PUBLICATIONS

All Office Actions; U.S. Appl. No. 18/432,499, filed Feb. 5, 2024.
(Continued)

*Primary Examiner* — Jacqueline F Stephens
(74) *Attorney, Agent, or Firm* — Charles R. Matson

(57)          ABSTRACT

A disposable absorbent article may include a chassis that includes a topsheet, a backsheet, and an absorbent core disposed between the topsheet and the backsheet; and a leg gasketing system and a waist gasketing element. The leg gasketing system may include an inner cuff and an outer cuff; the inner cuff may include an inner cuff folded edge and an inner cuff material edge and the outer cuff may include an outer cuff folded edge and an outer cuff material edge such that the web of material is folded laterally inward to form the outer cuff folded edge and folded laterally outward to form the inner cuff folded edge. The leg gasketing system may
(Continued)

also include a leg gasketing system pocket with an opening on an inboard longitudinal edge of the pocket.

17 Claims, 31 Drawing Sheets

Related U.S. Application Data continuation of application No. 15/074,300, filed on Mar. 18, 2016, now Pat. No. 10,531,991.

(60) Provisional application No. 62/134,977, filed on Mar. 18, 2015.

(51) Int. Cl.

| | |
|---|---|
| *A61F 13/494* | (2006.01) |
| *A61F 13/495* | (2006.01) |
| *A61F 13/496* | (2006.01) |
| *A61F 13/551* | (2006.01) |

(52) U.S. Cl.
CPC .......... *A61F 13/495* (2013.01); *A61F 13/496* (2013.01); *A61F 13/55105* (2013.01); *A61F 2013/49092* (2013.01)

(58) Field of Classification Search
CPC .. A61F 13/49; A61F 13/531; A61F 13/55105; A61F 2013/49092
See application file for complete search history.

(56) References Cited

U.S. PATENT DOCUMENTS

| | | |
|---|---|---|
| 4,055,182 A | 10/1977 | Mack |
| 4,324,245 A | 4/1982 | Mesek et al. |
| 4,552,795 A | 11/1985 | Hansen et al. |
| 4,610,678 A | 9/1986 | Weisman |
| 4,639,390 A | 1/1987 | Shoji |
| 4,662,875 A | 5/1987 | Hirotsu |
| 4,673,402 A | 6/1987 | VVeisman et al. |
| 4,699,622 A | 10/1987 | Toussant |
| 4,738,677 A | 4/1988 | Foreman |
| 4,753,646 A | 6/1988 | Enloe |
| 4,808,178 A | 2/1989 | Aziz |
| 4,808,252 A | 2/1989 | Lash |
| 4,816,025 A | 3/1989 | Foreman |
| 4,834,735 A | 5/1989 | Alemany |
| 4,846,815 A | 7/1989 | Scripps |
| 4,850,990 A | 7/1989 | Huntoon et al. |
| 4,883,549 A | 11/1989 | Frost et al. |
| 4,888,231 A | 12/1989 | Angstadt |
| 4,892,536 A | 1/1990 | Desmarais |
| 4,894,060 A | 1/1990 | Nestegard |
| 4,909,803 A | 3/1990 | Aziz |
| 4,923,660 A | 5/1990 | Willenberg |
| 4,938,754 A | 7/1990 | Mesek |
| 4,938,755 A | 7/1990 | Foreman |
| 4,940,464 A | 7/1990 | Van Gompel |
| 4,946,527 A | 8/1990 | Battrell |
| 4,963,140 A | 10/1990 | Robertson |
| 4,990,147 A | 2/1991 | Freeland |
| 5,021,051 A | 6/1991 | Hiuke |
| 5,026,334 A | 6/1991 | Jeffries |
| 5,026,364 A | 6/1991 | Robertson |
| 5,037,416 A | 8/1991 | Allen |
| 5,061,261 A | 10/1991 | Suzuki |
| 5,137,537 A | 8/1992 | Herron |
| 5,147,345 A | 9/1992 | Lavon |
| 5,151,092 A | 9/1992 | Buell |
| 5,156,793 A | 10/1992 | Buell |
| 5,167,653 A | 12/1992 | Igaue et al. |
| 5,167,897 A | 12/1992 | Weber |
| 5,171,391 A | 12/1992 | Suzuki et al. |
| 5,187,817 A | 2/1993 | Zolner |
| 5,196,000 A | 3/1993 | Clear et al. |
| 5,221,274 A | 6/1993 | Buell |
| 5,242,436 A | 9/1993 | Weil |
| 5,260,345 A | 11/1993 | Desmarais |
| 5,269,775 A | 12/1993 | Freeland |
| 5,281,207 A | 1/1994 | Chmielewski et al. |
| 5,342,338 A | 8/1994 | Roe |
| 5,358,500 A | 10/1994 | Lavon et al. |
| 5,387,207 A | 2/1995 | Dyer |
| 5,397,316 A | 3/1995 | Young |
| 5,397,318 A | 3/1995 | Dreier |
| 5,415,644 A | 5/1995 | Enloe |
| 5,482,625 A | 1/1996 | Shimizu et al. |
| 5,486,418 A | 1/1996 | Ohmory |
| 5,499,978 A | 3/1996 | Buell |
| 5,507,736 A | 4/1996 | Clear |
| 5,531,730 A | 7/1996 | Dreier |
| 5,540,671 A | 7/1996 | Dreier |
| 5,545,158 A | 8/1996 | Jessup |
| 5,554,145 A | 9/1996 | Roe |
| 5,558,660 A | 9/1996 | Dreier |
| 5,558,661 A | 9/1996 | Roe et al. |
| 5,567,254 A | 10/1996 | Sageser |
| 5,569,227 A | 10/1996 | Vandemoortele et al. |
| 5,569,234 A | 10/1996 | Buell |
| 5,571,096 A | 11/1996 | Dobrin |
| 5,575,785 A | 11/1996 | Gryskiewicz et al. |
| 5,576,090 A | 11/1996 | Suzuki |
| 5,580,411 A | 12/1996 | Nease |
| 5,584,828 A | 12/1996 | Yamamoto et al. |
| 5,591,152 A | 1/1997 | Buell |
| 5,593,401 A | 1/1997 | Sosalla et al. |
| 5,601,543 A | 2/1997 | Dreier et al. |
| 5,607,760 A | 3/1997 | Roe |
| 5,609,587 A | 3/1997 | Roe |
| 5,625,222 A | 4/1997 | Yoneda |
| 5,635,191 A | 6/1997 | Roe |
| 5,643,243 A | 7/1997 | Klemp |
| 5,643,588 A | 7/1997 | Roe |
| 5,672,166 A | 9/1997 | Vandemoortele |
| 5,674,215 A | 10/1997 | Roennberg |
| 5,681,302 A | 10/1997 | Melbye et al. |
| 5,694,918 A | 12/1997 | Blount |
| 5,695,488 A | 12/1997 | Sosalla |
| 5,749,865 A | 5/1998 | Yamamoto et al. |
| 5,769,838 A | 6/1998 | Buell et al. |
| 5,827,259 A | 10/1998 | Laux |
| 5,827,387 A | 10/1998 | Reynolds et al. |
| 5,833,677 A | 11/1998 | Sauer |
| 5,865,823 A | 2/1999 | Curro |
| 5,879,341 A | 3/1999 | Odorzynski et al. |
| 5,895,382 A | 4/1999 | Coenen et al. |
| 5,899,895 A | 5/1999 | Robles et al. |
| 5,904,675 A | 5/1999 | Laux |
| 5,911,713 A | 6/1999 | Yamada |
| 5,931,825 A | 8/1999 | Kuen et al. |
| 5,931,826 A | 8/1999 | Faulks et al. |
| 5,938,652 A | 8/1999 | Sauer |
| 5,942,179 A | 8/1999 | Tallentire |
| 5,993,433 A | 11/1999 | St Louis |
| 6,004,306 A | 12/1999 | Robles |
| 6,107,537 A | 8/2000 | Elder |
| 6,117,121 A | 9/2000 | Faulks et al. |
| 6,120,486 A | 9/2000 | Toyoda et al. |
| 6,120,487 A | 9/2000 | Ashton |
| 6,123,694 A | 9/2000 | Pieniak et al. |
| 6,132,410 A | 10/2000 | Van Gompel et al. |
| 6,135,988 A | 10/2000 | Turner et al. |
| 6,140,551 A | 10/2000 | Niemeyer et al. |
| 6,142,985 A | 11/2000 | Feist |
| 6,152,906 A | 11/2000 | Faulks et al. |
| 6,171,290 B1 | 1/2001 | Boisse et al. |
| 6,174,302 B1 | 1/2001 | Kumasaka |
| 6,186,996 B1 | 2/2001 | Martin |
| 6,217,563 B1 | 4/2001 | Van Gompel et al. |
| 6,231,558 B1 | 5/2001 | Mosley |
| 6,248,097 B1 * | 6/2001 | Beitz ................... A61F 13/4942 604/385.27 |
| 6,258,076 B1 | 7/2001 | Glaug et al. |

(56) References Cited

U.S. PATENT DOCUMENTS

| | | | |
|---|---|---|---|
| 6,264,639 | B1 | 7/2001 | Sauer |
| 6,264,641 | B1 | 7/2001 | Gompel |
| 6,264,642 | B1 | 7/2001 | Kuen et al. |
| 6,264,643 | B1 | 7/2001 | Toyoda |
| 6,280,426 | B1 | 8/2001 | Turner et al. |
| 6,293,934 | B1 | 9/2001 | Kumasaka |
| 6,312,420 | B1 | 11/2001 | Sasaki et al. |
| 6,315,764 | B1 | 11/2001 | Faulks et al. |
| 6,336,922 | B1 | 1/2002 | Vangompel et al. |
| 6,346,162 | B1 | 2/2002 | Reynolds et al. |
| 6,364,863 | B1 | 4/2002 | Yamamoto et al. |
| 6,375,646 | B1 | 4/2002 | Widlund et al. |
| 6,413,249 | B1 | 7/2002 | Turi et al. |
| 6,425,889 | B1 | 7/2002 | Kitaoka et al. |
| 6,432,098 | B1 | 8/2002 | Kline |
| 6,436,216 | B1 | 8/2002 | Grover |
| 6,440,117 | B1 | 8/2002 | Itoh et al. |
| 6,440,239 | B1 | 8/2002 | Vogt |
| 6,451,001 | B2 | 9/2002 | Kumasaka |
| 6,461,342 | B2 | 10/2002 | Tanji et al. |
| 6,478,785 | B1 | 11/2002 | Ashton et al. |
| 6,491,677 | B1 | 12/2002 | Glaug et al. |
| 6,494,872 | B1 | 12/2002 | Suzuki et al. |
| 6,506,185 | B1 | 1/2003 | Sauer et al. |
| 6,527,893 | B1 | 3/2003 | Boisse et al. |
| 6,562,123 | B2 | 5/2003 | Falster et al. |
| 6,565,976 | B1 | 5/2003 | Qureshi et al. |
| 6,569,139 | B1 | 5/2003 | Datta et al. |
| 6,569,140 | B1 | 5/2003 | Mizutani et al. |
| 6,592,562 | B2 | 7/2003 | Menard et al. |
| 6,613,033 | B1 | 9/2003 | Coenen et al. |
| 6,629,967 | B1 | 10/2003 | Simmons et al. |
| 6,638,262 | B2 | 10/2003 | Suzuki et al. |
| 6,641,570 | B2 | 11/2003 | Mishima et al. |
| 6,641,692 | B2 | 11/2003 | Reynolds et al. |
| 6,659,990 | B1 | 12/2003 | Odorzynski et al. |
| 6,682,515 | B1 | 1/2004 | Mizutani et al. |
| 6,682,516 | B2 | 1/2004 | Johnston et al. |
| 6,699,228 | B1 | 3/2004 | Chmielewski et al. |
| 6,702,801 | B2 | 3/2004 | Van Gompel et al. |
| 6,706,029 | B1 | 3/2004 | Suzuki et al. |
| 6,706,030 | B1 | 3/2004 | Okuda et al. |
| 6,767,343 | B2 | 7/2004 | Shimada et al. |
| 6,767,344 | B2 | 7/2004 | Suzuki |
| 6,808,582 | B2 | 10/2004 | Coenen et al. |
| 6,837,958 | B2 | 1/2005 | Otsubo et al. |
| 6,840,930 | B1 | 1/2005 | Miyamoto et al. |
| 6,884,310 | B2 | 4/2005 | Roessler et al. |
| 6,903,793 | B2 | 6/2005 | Kaneko et al. |
| 6,921,394 | B2 | 7/2005 | Sayama et al. |
| 6,978,486 | B2 | 12/2005 | Zhou et al. |
| 7,014,632 | B2 | 3/2006 | Takino et al. |
| 7,018,368 | B2 | 3/2006 | Van Gompel et al. |
| 7,037,300 | B2 | 5/2006 | Kling |
| 7,135,014 | B2 | 11/2006 | Sasaki et al. |
| 7,150,729 | B2 | 12/2006 | Shimada et al. |
| 7,156,828 | B2 | 1/2007 | Ostrow |
| 7,163,530 | B1 | 1/2007 | Toyoshima et al. |
| 7,169,136 | B2 | 1/2007 | Otsubo et al. |
| 7,189,219 | B1 | 3/2007 | Kasai et al. |
| 7,195,621 | B2 | 3/2007 | Ohnishi et al. |
| 7,207,978 | B2 | 4/2007 | Takino et al. |
| 7,226,437 | B2 | 6/2007 | Sasaki et al. |
| 7,264,686 | B2 | 9/2007 | Thorson et al. |
| 7,291,138 | B2 | 11/2007 | Hoshino et al. |
| 7,331,946 | B2 | 2/2008 | Shimada et al. |
| 7,338,479 | B2 | 3/2008 | Fujioka et al. |
| 7,378,360 | B2 | 5/2008 | Clark et al. |
| 7,378,568 | B2 | 5/2008 | Thomas et al. |
| 7,435,243 | B2 | 10/2008 | Miyamoto |
| 7,435,244 | B2 | 10/2008 | Schroer, Jr. et al. |
| 7,527,616 | B2 | 5/2009 | Miyamoto |
| 7,561,602 | B1 | 7/2009 | Nakabayashi |
| 7,569,039 | B2 | 8/2009 | Matsuda |
| 7,604,625 | B2 | 10/2009 | Turi et al. |
| 7,621,900 | B2 | 11/2009 | Van Gompel et al. |
| 7,626,073 | B2 | 12/2009 | Catalan |
| 7,666,176 | B2 | 2/2010 | Erdman et al. |
| 7,670,325 | B2 | 3/2010 | Oji et al. |
| 7,708,725 | B2 | 5/2010 | Tamagawa et al. |
| 7,722,590 | B2 | 5/2010 | Tsuji et al. |
| 7,722,591 | B2 | 5/2010 | Baeck |
| 7,727,214 | B2 | 6/2010 | Torigoshi et al. |
| 7,727,215 | B2 | 6/2010 | Kenmochi et al. |
| 7,744,576 | B2 | 6/2010 | Busam |
| 7,744,579 | B2 | 6/2010 | Langdon et al. |
| 7,750,203 | B2 | 7/2010 | Becker et al. |
| 7,753,899 | B2 | 7/2010 | Mori et al. |
| 7,754,040 | B2 | 7/2010 | Norrby |
| 7,785,309 | B2 | 8/2010 | Van Gompel et al. |
| 7,794,441 | B2 | 9/2010 | Ashton et al. |
| 7,834,236 | B2 | 11/2010 | Middlesworth et al. |
| 7,838,724 | B2 | 11/2010 | Van Gompel et al. |
| 7,879,017 | B1 | 2/2011 | Tabata |
| 7,918,839 | B2 | 4/2011 | Ehrnsperger et al. |
| 7,918,840 | B2 | 4/2011 | Corneliusson |
| 7,959,619 | B2 | 6/2011 | Cartier et al. |
| 8,002,760 | B2 | 8/2011 | Ehrnsperger et al. |
| 8,038,662 | B2 | 10/2011 | Hornung et al. |
| 8,043,274 | B2 | 10/2011 | Mlinar et al. |
| 8,043,275 | B2 | 10/2011 | Peterson |
| 8,062,279 | B2 | 11/2011 | Miyamoto |
| 8,075,543 | B2 | 12/2011 | Okuda |
| 8,105,303 | B2 | 1/2012 | Sakaguchi |
| 8,114,059 | B2 | 2/2012 | Ehrnsperger et al. |
| 8,152,788 | B2 | 4/2012 | Beckert et al. |
| 8,182,627 | B2 | 5/2012 | Eckstein et al. |
| 8,211,077 | B2 | 7/2012 | Sugiyama et al. |
| 8,212,102 | B2 | 7/2012 | Kumasaka |
| 8,231,592 | B2 | 7/2012 | Suzuki et al. |
| 8,251,967 | B2 | 8/2012 | Malowaniec et al. |
| 8,328,782 | B2 | 12/2012 | Catalan |
| 8,333,749 | B2 | 12/2012 | Tsang et al. |
| 8,348,919 | B2 | 1/2013 | Langdon et al. |
| 8,353,891 | B2 | 1/2013 | Hornung et al. |
| 8,377,023 | B2 | 2/2013 | Sawyer et al. |
| 8,382,735 | B2 | 2/2013 | Torigoshi et al. |
| 8,475,424 | B2 | 7/2013 | Fujimoto et al. |
| 8,496,638 | B2 | 7/2013 | Lord et al. |
| 8,513,483 | B2 | 8/2013 | Tee, Jr. et al. |
| 8,518,010 | B2 | 8/2013 | Kuwano et al. |
| 8,551,064 | B2 | 10/2013 | Lavon et al. |
| 8,568,566 | B2 | 10/2013 | Jackels et al. |
| 8,663,184 | B2 | 3/2014 | Liu et al. |
| 8,668,680 | B2 | 3/2014 | Ichikawa et al. |
| 8,679,084 | B2 | 3/2014 | Kurihara |
| 8,716,549 | B2 | 5/2014 | Cheng et al. |
| 8,764,722 | B2 | 7/2014 | Rhein et al. |
| 8,777,918 | B2 | 7/2014 | Kuwano et al. |
| 8,795,250 | B2 | 8/2014 | O'connell |
| 8,939,957 | B2 | 1/2015 | Raycheck |
| 9,044,358 | B2 | 6/2015 | Nakajima et al. |
| 9,066,838 | B2 | 6/2015 | Hippe et al. |
| 9,089,455 | B2 | 7/2015 | Raycheck et al. |
| 9,737,444 | B2 | 8/2017 | Lawson et al. |
| 9,750,651 | B2 | 9/2017 | Bianchi et al. |
| 10,022,280 | B2 | 7/2018 | Ehrnsperger et al. |
| 10,085,895 | B2 | 10/2018 | Takino et al. |
| 10,485,710 | B2 | 11/2019 | Surushe |
| 10,524,962 | B2 | 1/2020 | Raycheck |
| 10,531,990 | B2 | 1/2020 | Raycheck et al. |
| 10,531,991 | B2 | 1/2020 | Raycheck |
| 10,537,481 | B2 | 1/2020 | Raycheck et al. |
| 10,583,049 | B2 | 3/2020 | Raycheck et al. |
| 10,588,789 | B2 | 3/2020 | Surushe et al. |
| 10,588,791 | B2 | 3/2020 | Raycheck |
| 11,478,385 | B2 | 10/2022 | Surushe |
| 11,504,282 | B2 | 11/2022 | Raycheck et al. |
| 11,504,283 | B2 | 11/2022 | Raycheck et al. |
| 2002/0128626 | A1 | 9/2002 | Friderich et al. |
| 2002/0177829 | A1 | 11/2002 | Fell |
| 2003/0012024 | A1 | 1/2003 | Wu |
| 2003/0023220 | A1 | 1/2003 | Ukegawa et al. |
| 2003/0050616 | A1 | 3/2003 | Reynolds et al. |

(56) References Cited

U.S. PATENT DOCUMENTS

| | | |
|---|---|---|
| 2003/0078558 A1 | 4/2003 | Karami et al. |
| 2003/0120247 A1 | 6/2003 | Miyamoto |
| 2003/0135185 A1 | 7/2003 | Crowther |
| 2004/0002690 A1 | 1/2004 | Miyamoto |
| 2004/0127876 A1 | 7/2004 | Stevens |
| 2004/0129597 A1 | 7/2004 | Fregonese et al. |
| 2004/0158217 A1 | 8/2004 | Wu |
| 2004/0222553 A1 | 11/2004 | Desai et al. |
| 2004/0243085 A1 | 12/2004 | Veith |
| 2005/0003048 A1 | 1/2005 | Pearce |
| 2005/0004549 A1 | 1/2005 | Maas et al. |
| 2005/0095700 A1 | 5/2005 | Budzowski et al. |
| 2005/0113790 A1 | 5/2005 | Suzuki et al. |
| 2005/0177123 A1 | 8/2005 | Catalan |
| 2005/0203479 A1 | 9/2005 | Sakaguchi et al. |
| 2005/0215155 A1 | 9/2005 | Young et al. |
| 2005/0222550 A1 | 10/2005 | Mitsui et al. |
| 2005/0281757 A1 | 12/2005 | Ibrahim |
| 2005/0288645 A1 | 12/2005 | Lavon |
| 2006/0014460 A1 | 1/2006 | Alexander et al. |
| 2006/0058767 A1 | 3/2006 | Zhang et al. |
| 2006/0058768 A1 | 3/2006 | Zhang et al. |
| 2006/0111686 A1 | 5/2006 | Schneider |
| 2006/0264860 A1 | 11/2006 | Lavon |
| 2006/0270302 A1 | 11/2006 | Ando |
| 2007/0005040 A1 | 1/2007 | Langdon et al. |
| 2007/0032772 A1 | 2/2007 | Ehrnsperger |
| 2007/0088116 A1 | 4/2007 | Abba et al. |
| 2007/0123834 A1 | 5/2007 | Mcdowall et al. |
| 2007/0191808 A1 | 8/2007 | Toyoshima et al. |
| 2007/0287980 A1 | 12/2007 | Kline et al. |
| 2007/0287983 A1 | 12/2007 | Lodge |
| 2008/0077111 A1 | 3/2008 | Erdman et al. |
| 2008/0195070 A1 | 8/2008 | Ponomarenko |
| 2008/0195071 A1 | 8/2008 | Ponomarenko et al. |
| 2008/0312617 A1 | 12/2008 | Hundorf |
| 2008/0312631 A1 | 12/2008 | Okuda |
| 2009/0118689 A1 | 5/2009 | Lawson et al. |
| 2009/0157034 A1 | 6/2009 | Mattingly et al. |
| 2009/0182298 A1 | 7/2009 | Kumasaka |
| 2009/0195187 A1 | 8/2009 | Chen et al. |
| 2009/0275911 A1 | 11/2009 | Hormung et al. |
| 2009/0312730 A1 | 12/2009 | Lavon |
| 2009/0312734 A1 | 12/2009 | Lavon et al. |
| 2010/0028638 A1 | 2/2010 | Reichardt et al. |
| 2010/0193110 A1 | 8/2010 | Eckstein et al. |
| 2010/0305532 A1 | 12/2010 | Ashton et al. |
| 2010/0312214 A1 | 12/2010 | Shimada et al. |
| 2010/0318054 A1 | 12/2010 | Langdon et al. |
| 2011/0004177 A1 | 1/2011 | Roe et al. |
| 2011/0022019 A1 | 1/2011 | Shimada et al. |
| 2011/0066128 A1 | 3/2011 | Takahashi |
| 2011/0092944 A1 | 4/2011 | Sagisaka et al. |
| 2011/0172626 A1 | 7/2011 | Mitsuno |
| 2011/0178489 A1 | 7/2011 | Baba et al. |
| 2011/0196327 A1 | 8/2011 | Chhabra et al. |
| 2011/0223381 A1 | 9/2011 | Sauter |
| 2011/0245792 A1 | 10/2011 | Oconnell |
| 2011/0250256 A1 | 10/2011 | Hyun-oh et al. |
| 2012/0027702 A1 | 2/2012 | Bernoud et al. |
| 2012/0073760 A1 | 3/2012 | Hamada et al. |
| 2012/0277702 A1 | 11/2012 | Raycheck |
| 2012/0277713 A1* | 11/2012 | Raycheck .............. A61F 13/496 604/385.01 |
| 2012/0289921 A1 | 11/2012 | Hashino et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0330262 A1 | 12/2012 | Lawson |
| 2012/0330263 A1 | 12/2012 | Lawson |
| 2012/0330264 A1 | 12/2012 | Lawson |
| 2013/0041340 A1 | 2/2013 | Kawakami |
| 2013/0255865 A1 | 10/2013 | Brown |
| 2014/0005621 A1 | 1/2014 | Roe |
| 2014/0142529 A1 | 5/2014 | Cheng |
| 2014/0163511 A1 | 6/2014 | Roe et al. |
| 2014/0371700 A1 | 12/2014 | Patel et al. |
| 2015/0073372 A1 | 3/2015 | Hippe et al. |
| 2016/0067940 A1 | 3/2016 | Liebe et al. |
| 2016/0270971 A1 | 9/2016 | Raycheck et al. |
| 2016/0270972 A1 | 9/2016 | Surushe et al. |
| 2016/0270973 A1 | 9/2016 | Surushe et al. |
| 2016/0270974 A1 | 9/2016 | Surushe et al. |
| 2016/0270975 A1 | 9/2016 | Surushe et al. |
| 2016/0270977 A1 | 9/2016 | Surushe et al. |
| 2016/0270978 A1 | 9/2016 | Raycheck et al. |
| 2016/0270979 A1 | 9/2016 | Raycheck et al. |
| 2016/0270980 A1 | 9/2016 | Raycheck et al. |
| 2016/0270981 A1 | 9/2016 | Raycheck et al. |
| 2016/0270982 A1 | 9/2016 | Raycheck et al. |
| 2016/0270983 A1 | 9/2016 | Roe et al. |
| 2016/0270985 A1 | 9/2016 | Raycheck et al. |
| 2016/0287449 A1 | 10/2016 | Surushe et al. |
| 2017/0266062 A1 | 9/2017 | Raycheck et al. |
| 2018/0042777 A1 | 2/2018 | Dalal |
| 2019/0365577 A1 | 12/2019 | Raycheck et al. |
| 2020/0054499 A1 | 2/2020 | Surushe et al. |
| 2020/0085643 A1 | 3/2020 | Raycheck et al. |
| 2020/0085646 A1 | 3/2020 | Raycheck et al. |
| 2020/0107972 A1 | 4/2020 | Raycheck et al. |
| 2020/0155366 A1 | 5/2020 | Raycheck et al. |
| 2020/0170852 A1 | 6/2020 | Surushe et al. |
| 2020/0188192 A1 | 6/2020 | Raycheck et al. |
| 2020/0397624 A1 | 12/2020 | Prakash et al. |
| 2022/0257432 A1 | 8/2022 | Raycheck et al. |
| 2023/0000695 A1 | 1/2023 | Surushe et al. |
| 2023/0037340 A1 | 2/2023 | Raycheck et al. |

FOREIGN PATENT DOCUMENTS

| | | |
|---|---|---|
| CN | 1589129 A | 3/2005 |
| CN | 101010053 A | 8/2007 |
| CN | 101027027 A | 8/2007 |
| CN | 101277664 A | 10/2008 |
| CN | 102413799 A | 4/2012 |
| CN | 102753129 A | 10/2012 |
| CN | 102821724 A | 12/2012 |
| CN | 202682191 U | 1/2013 |
| CN | 103705344 A | 4/2014 |
| CN | 103732194 A | 4/2014 |
| CN | 203576760 U | 5/2014 |
| CN | 104185462 A | 12/2014 |
| CN | 104185465 A | 12/2014 |
| CN | 104958139 A | 10/2015 |
| EA | 200901264 A1 | 4/2010 |
| EP | 0214636 B1 | 11/1991 |
| EP | 0486006 A2 | 5/1992 |
| EP | 0404648 B1 | 2/1994 |
| EP | 0412579 B1 | 6/1994 |
| EP | 0403832 B1 | 10/1994 |
| EP | 0773769 B1 | 11/2000 |
| EP | 0866682 B1 | 3/2002 |
| EP | 0376022 B2 | 3/2006 |
| EP | 1905402 A2 | 6/2008 |
| GB | 2383522 A | 7/2003 |
| JP | 6426701 A | 1/1989 |
| JP | H0265861 A | 3/1990 |
| JP | 7184955 A | 7/1995 |
| JP | 07313550 A | 12/1995 |
| JP | H08215239 A | 8/1996 |
| JP | 8252280 A | 10/1996 |
| JP | 2525656 B2 | 2/1997 |
| JP | 9215709 A | 8/1997 |
| JP | 2810738 B2 | 10/1998 |
| JP | H10277091 A | 10/1998 |
| JP | 11253483 A | 9/1999 |
| JP | 11318978 A | 11/1999 |
| JP | 11323611 A | 11/1999 |
| JP | 2602070 Y2 | 12/1999 |
| JP | 2000014702 A | 1/2000 |
| JP | 2603259 Y2 | 3/2000 |
| JP | 2000254176 A | 9/2000 |
| JP | 2000288012 A | 10/2000 |

(56) References Cited

FOREIGN PATENT DOCUMENTS

| | | | |
|---|---|---|---|
| JP | 2000288016 | A | 10/2000 |
| JP | 2000342623 | A | 12/2000 |
| JP | 2001245922 | A | 9/2001 |
| JP | 3242586 | B2 | 12/2001 |
| JP | 2002102279 | A | 4/2002 |
| JP | 2002209938 | A | 7/2002 |
| JP | 3315993 | B2 | 8/2002 |
| JP | 2002253604 | A | 9/2002 |
| JP | 3391776 | B2 | 3/2003 |
| JP | 3391779 | B2 | 3/2003 |
| JP | 3406231 | B2 | 5/2003 |
| JP | 3488506 | B2 | 1/2004 |
| JP | 3493211 | B2 | 2/2004 |
| JP | 3592591 | B2 | 9/2004 |
| JP | 3605426 | B2 | 10/2004 |
| JP | 3606297 | B2 | 10/2004 |
| JP | 3615894 | B2 | 11/2004 |
| JP | 3771466 | B2 | 2/2006 |
| JP | 3773550 | B2 | 2/2006 |
| JP | 3825977 | B2 | 7/2006 |
| JP | 3856904 | B2 | 9/2006 |
| JP | 2006263306 | A | 10/2006 |
| JP | 3884292 | B2 | 11/2006 |
| JP | 2006320709 | A | 11/2006 |
| JP | 3926585 | B2 | 3/2007 |
| JP | 2007143633 | A | 6/2007 |
| JP | 3953228 | B2 | 8/2007 |
| JP | 2008302138 | A | 12/2008 |
| JP | 4215370 | B2 | 1/2009 |
| JP | 2009056142 | A | 3/2009 |
| JP | 4330281 | B2 | 9/2009 |
| JP | 2011177288 | A | 9/2011 |
| JP | 4996508 | B2 | 5/2012 |
| JP | 5001756 | B2 | 5/2012 |
| JP | 5192367 | B2 | 2/2013 |
| JP | 2014012219 | A | 1/2014 |
| JP | 2014068848 | A | 4/2014 |
| JP | 2014083191 | A | 5/2014 |
| JP | 5651801 | B1 | 11/2014 |
| WO | 199404656 | A2 | 3/1994 |
| WO | 199303698 | A1 | 6/1994 |
| WO | 199516746 | A1 | 6/1995 |
| WO | 199603953 | A1 | 2/1996 |
| WO | 199720532 | A1 | 6/1997 |
| WO | 200236059 | A1 | 10/2002 |
| WO | 20051095700 | | 1/2006 |
| WO | 2006135357 | A1 | 12/2006 |
| WO | 2012067216 | A1 | 5/2012 |
| WO | 2013065618 | A1 | 5/2013 |
| WO | 2013065619 | A1 | 5/2013 |
| WO | 2014020382 | A1 | 2/2014 |
| WO | 2014125858 | A1 | 8/2014 |
| WO | 2014147879 | A1 | 9/2014 |
| WO | 2015005166 | A1 | 1/2015 |
| WO | 2015198928 | A1 | 12/2015 |
| WO | 2016051936 | A1 | 4/2016 |
| WO | 2016051937 | A1 | 4/2016 |
| WO | 2016051938 | A1 | 4/2016 |

OTHER PUBLICATIONS

All Office Actions; U.S. Appl. No. 18/599,292, filed Mar. 8, 2024.

U.S. Unpublished U.S. Appl. No. 18/432,499, filed Feb. 5, 2024, to Abhishek Prakash Surushe et al.

U.S. Unpublished U.S. Appl. No. 18/599,292, filed Mar. 8, 2024, to Jeromy Thomas Raycheck et al.

All Office Actions; U.S. Appl. No. 15/074,047, filed Mar. 18, 2016.

All Office Actions; U.S. Appl. No. 15/074,066, filed Mar. 18, 2016.

All Office Actions; U.S. Appl. No. 15/074,352, filed Mar. 18, 2016.

All Office Actions; U.S. Appl. No. 15/074,496, filed Mar. 18, 2016.

All Office Actions; U.S. Appl. No. 15/074,543, filed Mar. 18, 2016.

All Office Actions; U.S. Appl. No. 15/074,583, filed Mar. 18, 2016.

All Office Actions; U.S. Appl. No. 15/074,650, filed Mar. 18, 2016.

All Office Actions; U.S. Appl. No. 15/074,675, filed Mar. 18, 2016.

All Office Actions; U.S. Appl. No. 15/074,108, filed Mar. 18, 2016.

All Office Actions; U.S. Appl. No. 15/074,145, filed Mar. 18, 2016.

All Office Actions; U.S. Appl. No. 15/074,300, filed Mar. 18, 2016.

All Office Actions; U.S. Appl. No. 15/074,453, filed Mar. 18, 2016.

All Office Actions; U.S. Appl. No. 16/543,984, filed Aug. 19, 2019.

All Office Actions; U.S. Appl. No. 16/663,763, filed Oct. 25, 2019.

All Office Actions; U.S. Appl. No. 16/690,841, filed Nov. 21, 2019.

All Office Actions; U.S. Appl. No. 16/693,457, filed Nov. 25, 2019.

All Office Actions; U.S. Appl. No. 16/693,766, filed Nov. 25, 2019.

All Office Actions; U.S. Appl. No. 16/752,769, filed Jan. 27, 2020.

All Office Actions; U.S. Appl. No. 16/782,187, filed Feb. 5, 2020.

All Office Actions; U.S. Appl. No. 16/795,778, filed Feb. 20, 2020.

All Office Actions; U.S. Appl. No. 17/009,836, filed Sep. 2, 2020.

All Office Actions; U.S. Appl. No. 17/712,545, filed Apr. 4, 2022.

All Office Actions; U.S. Appl. No. 17/903,281, filed Sep. 6, 2022.

All Office Actions; U.S. Appl. No. 17/964,993, filed Oct. 13, 2022.

All Office Actions; U.S. Appl. No. 18/133,230, filed Apr. 11, 2023.

All Office Actions; U.S. Appl. No. 15/074,382, filed Mar. 18, 2016.

All Office Actions; U.S. Appl. No. 15/074,211, filed Mar. 18, 2016.

All Office Actions; U.S. Appl. No. 15/074,240, filed Mar. 18, 2016.

PCT Search Report and Written Opinion for PCT/US2016/023084 dated Jun. 21, 2016, 13 pages.

U.S. Unpublished U.S. Appl. No. 18/133,230, filed Apr. 11, 2023, to Jeromy Thomas Raycheck et al.

* cited by examiner

ABSORBENT ARTICLE WITH WAIST GASKETING ELEMENT AND LEG CUFFS

CROSS REFERENCE TO RELATED APPLICATION

This application is a continuation of U.S. application Ser. No. 16/690,841, filed on Nov. 21, 2019, which is a continuation of U.S. application Ser. No. 15/074,300, filed on Mar. 18, 2016, which claims the benefit of U.S. Provisional Application No. 62/134,977, filed Mar. 18, 2015, which are incorporated herein by reference.

FIELD OF INVENTION

This invention relates to absorbent articles (e.g., diapers, adult incontinence articles, feminine hygiene pads) having improved leg cuffs that yield a more garment-like article, as well as having improved functional characteristics (e.g., reduced leakage, fecal material containment).

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Current diaper designs frequently include the use of a barrier leg cuff to prevent leakage of bodily exudates and an outer cuff which provides a covering over the barrier leg cuff to minimize the visibility of exudates through the barrier cuff and provide a secondary means to capture bodily exudates should they breach the barrier leg cuff. The barrier leg cuff may be made using a hydrophobic nonwoven and may be disposed on the body-facing surface of the absorbent article or connected to the body-facing surface of the film backsheet layer. The barrier leg cuff may be a substantially liquid impervious layer that prevents bodily exudates from passing out of the sides of the article and may also be highly breathable, allowing outside air to reach the skin to help maintain a healthy level of skin hydration. In many current diapers, the outer cuff comprises the polymeric film layer of the backsheet to provide high opacity required to cover the barrier leg cuff as well as to prevent molten adhesive from passing through the cuff to the garment-facing surface of the article during manufacturing. The outer cuff contains the outer leg elastic strands, which create the contraction forces and gathers, and can be sandwiched between the cuff material and backsheet material. The elastic strands in the leg cuffs are typically joined with molten adhesive during manufacture, and the hot adhesive generally has the potential to pass through nonwoven materials during manufacture, causing contamination of manufacturing lines as well as the potential for stickiness on the outside surface of the article. The polymeric film generally is used to prevent these issues, however, results in a plastic-like look as well as a noisy application process.

Because of manufacturing tolerances when cutting, tracking, and combining materials, the outer leg elastic strands are generally spaced inboard from the longitudinal edge of the article in the crotch region. This prevents inadvertent cutting or exposure of the outer leg elastic strands during the manufacturing process. This design does not result in the outermost portion of the longitudinal edge of the product continuously contacting closely to the skin of the user during wear. Thus, the ability of the elastic strand(s) to control the edge of the article diminishes as the distance between the outermost elastic and the edge increases, leading to a more random distribution of larger gathers which contact the skin at larger intervals or sometimes not at all. This effect can lead to user perception that the diaper may leak where the longitudinal edge does not contact the skin of the user. In addition, many articles currently available contain only two to three outer leg elastics per side to create the gathers, increasing the difficulty of achieving the desired appearance of a wide finished leg cuff or more garment-like cuff such as the elasticized hemmed edge of the arm cuff of a sweater. If the elastics are spaced more closely, the result is a narrow section of elasticized zone, which results in a less finished, less comfortable, and less clothing-like appearance. If the elastics are spaced farther apart, the gathers can appear to separate further from the skin of the user, leading to a perception of potential leakage risk. As discussed above, this is driven by having less control of the gathers between strands of increasing separation.

Accordingly, it is desirable to provide an absorbent article with a folded outer cuff design having finished edges with elastics that are close to the edge to maintain a close proximity to the skin to create improved fit, a more aesthetically pleasing, clothing-like design and improved leakage protection.

However, even with the improved leakage protection provided by the cuff designs detailed herein, the most common mode of failure for absorbent articles still occurs when body exudates leak out of the gaps between the article and the wearer's legs and/or waist. When fecal material (e.g., runny bowel movement, a mixture of bowel movement and urine, etc.) is not absorbed into the topsheet and core of absorbent article, the fecal material can leak out of the gaps between the article and the wearer's legs or waist. In situations where a wearer exudes a higher quantity of fecal material—which is absorbed by the absorbent core more slowly than urine—the fecal material may move laterally along the body-side surface of the absorbent article and reach the barrier leg cuff. Fecal material may also travel longitudinally along the barrier leg cuffs or longitudinally up the gluteal grove of the wearer towards the waist. Due to the movement of the wearer and/or a shortage of available space under the barrier cuffs and/or within the absorbent article, the fecal material may leak out of the gaps between the article and the wearer's legs and/or waist. This results in soiling, wetting, or otherwise contaminating the wearer's clothing or other articles (e.g., bedding, furniture, caregiver clothing, etc.) that come in contact with the wearer's leaky absorbent article.

Accordingly, it is of continued interest to provide an economically viable disposable absorbent article with the ability to minimize the negative effects of bodily extrudate leaks, while also making it easier to clean the wearer when the soiled disposable absorbent article is removed. To that end, it is of continued interest to provide a disposable absorbent article having sufficient retention capability to safely and cleanly retain bodily extrudate away from the wearer's clothing and/or skin throughout the expected time of article use.

SUMMARY OF THE INVENTION

In one aspect, a disposable absorbent article for wearing about the lower torso of a wearer includes a first waist region, a second waist region, a crotch region disposed between the first and second waist regions; a first waist edge and a second waist edge; and a first longitudinal edge and a second longitudinal edge; wherein the disposable absorbent article includes a chassis including a topsheet; a backsheet; and an absorbent core disposed between the topsheet and the backsheet; wherein the disposable absorbent article further includes a leg gasketing system and at least one waist gasketing element; wherein the leg gasketing system includes a web of material forming an inner cuff and an outer cuff; wherein the inner cuff includes an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the web of material between the outer cuff folded edge and the outer cuff material edge in the crotch region and the first waist region; and the web of material between the inner cuff folded edge and the outer cuff folded edge is unattached to the web of material between the outer cuff folded edge and the outer cuff material edge in at least a portion of the second waist region, forming a leg gasketing system pocket with an opening on an inboard longitudinal edge of the leg gasketing system pocket; wherein the at least one waist gasketing element has an inboard lateral edge, an outboard lateral edge, and two longitudinal edges; the at least one waist gasketing element including at least one elastic material; wherein the at least one waist gasketing element is attached to: 1) the chassis of the disposable absorbent article and 2) the leg gasketing system, such that at least a portion of the outboard lateral edge of the waist gasketing element is attached to the chassis and at least a portion of the outboard lateral edge of the waist gasketing element is attached to the web of material forming the leg gasketing system; and wherein the inboard lateral edge of the waist gasketing element is unattached to the chassis of the disposable absorbent article.

In another aspect, a disposable absorbent article for wearing about the lower torso of a wearer includes: a first waist region, a second waist region, a crotch region disposed between the first and second waist regions; a first waist edge and a second waist edge; and a first longitudinal edge and a second longitudinal edge; wherein the disposable absorbent article comprises a chassis includes a topsheet; a backsheet; and an absorbent core disposed between the topsheet and the backsheet; wherein the disposable absorbent article further includes a leg gasketing system and at least one waist gasketing element; wherein the leg gasketing system includes a web of material forming an inner cuff and an outer cuff; wherein the inner cuff includes an inner cuff folded edge and an inner cuff material edge and the outer cuff includes an outer cuff folded edge and an outer cuff material edge, such that the web of material is folded laterally inward to form the outer cuff folded edge and folded laterally outward to form the inner cuff folded edge; wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the web of material between the outer cuff folded edge and the outer cuff material edge in the crotch region and the first waist region; wherein the outer cuff includes an elastics adhesive and at least one longitudinally oriented elastic member running parallel to the outer cuff folded edge, the elastics adhesive and at least one elastic member disposed between 1) the web of material between the outer cuff folded edge and the outer cuff material edge and 2) the web of material between the outer cuff folded edge and the inner cuff folded edge; wherein in at least a portion of the second waist region, the outer cuff is free of elastics adhesive and elastic members, thus forming a leg gasketing system pocket between 1) the web of material between the outer cuff folded edge and the outer cuff material edge and 2) the web of material between the outer cuff folded edge and the inner cuff folded edge; the leg gasketing system pocket having an outboard longitudinal edge at the outer cuff folded edge; wherein the leg gasketing system pocket includes an opening on an inboard longitudinal edge of the leg gasketing system pocket; wherein the at least one waist gasketing element has an inboard lateral edge, an outboard lateral edge, and two longitudinal edges; the at least one waist gasketing element including at least one elastic material; wherein the at least one waist gasketing element is attached to: 1) the chassis of the disposable absorbent article and 2) the leg gasketing system, such that at least a portion of the outboard lateral edge of the waist gasketing element is attached to the chassis and at least a portion of the outboard lateral edge of the waist gasketing element is attached to the web of material forming the leg gasketing system; and wherein the inboard lateral edge of the waist gasketing element is unattached to the chassis of the disposable absorbent article.

In another aspect, a package includes at least ten disposable absorbent articles for wearing about the lower torso of a wearer, the disposable absorbent articles including a first waist region, a second waist region, a crotch region disposed between the first and second waist regions; a first waist edge and a second waist edge; and a first longitudinal edge and a second longitudinal edge; wherein the disposable absorbent article includes a chassis including a topsheet; a backsheet; and an absorbent core disposed between the topsheet and the backsheet; wherein the disposable absorbent article further includes a leg gasketing system and at least one waist gasketing element; wherein the leg gasketing system includes a web of material forming an inner cuff and an outer cuff; wherein the inner cuff includes an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the web of material between the outer cuff folded edge and the outer cuff material edge in the crotch region and the first waist region; and the web of material between the inner cuff folded edge and the outer cuff folded edge is unattached to the web of material between the outer cuff folded edge and the outer cuff material edge in at least a portion of the second waist region, forming a leg gasketing system pocket with an opening on an inboard longitudinal edge of the leg gasketing system pocket; wherein the at least one waist gasketing element has an inboard lateral edge, an outboard lateral edge, and two longitudinal edges; the at least one waist gasketing element including at least one elastic material; wherein the at least one waist gasketing element is attached to: 1) the chassis of the disposable absorbent article and 2) the leg gasketing system, such that at least a portion of the outboard lateral edge of the waist gasketing element is attached to the chassis and at least a portion of the outboard lateral edge of the waist gasketing element is attached to the web of material forming the leg gasketing system; and wherein the inboard lateral edge of the waist gasketing element is unattached to the chassis of the disposable absorbent article.

The disposable absorbent articles described herein comprise leg gasketing systems or waist gasketing elements that may comprise one web or multiple webs of material. The description and claims herein may refer to leg gasketing system embodiments and waist gasketing elements that are formed from "a web of material." The recitation of "a web of material" encompasses a single continuous web of material, multiple webs of material that are joined together to become one web of material, or multiple distinct webs of material that are separate from the disposable absorbent article chassis, and form part of the leg gasketing system or the waist gasketing element. The leg gasketing systems and/or waist gasketing elements described herein may comprise N-fiber material or other non-woven materials.

BRIEF DESCRIPTION OF THE DRAWINGS

FIG. 24 is substantially identical to the exemplary embodiment of FIG. 1, with the addition of a waist gasketing element in the second waist region.

DETAILED DESCRIPTION OF THE INVENTION

Figure 1:
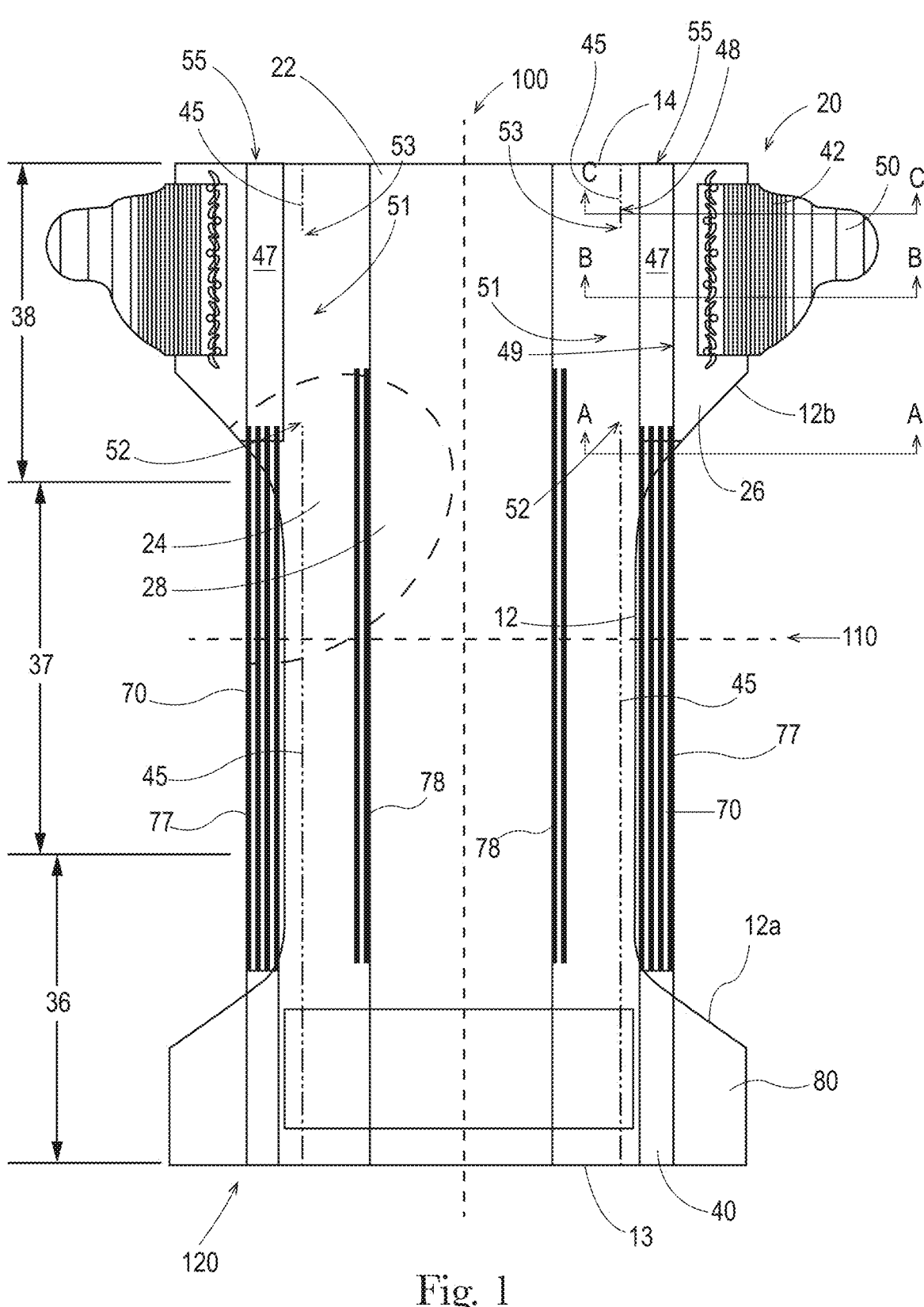
FIG. 1 is a schematic plan view of an exemplary embodiment of an absorbent article as detailed herein.

Definitions:

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Absorbent Article:

The present disclosure is directed to a disposable absorbent article with a leg gasketing system that comprises a folded outer cuff having neatly finished outer cuff folded edges that creates an aesthetically pleasing design that is garment like, the absorbent article also including a leg gasketing system pocket with an opening towards the interior of the article, wherein the pocket reduces runny bowel movement leaks. In one embodiment, the folded outer cuff design is advantageous in preventing penetration and adhesive bleedthrough without the use of a polymeric film layer in the elasticized region. In one embodiment, the absorbent article may comprise an opacity strengthening patch to provide the strength needed to prevent the article from extending excessively during application and wearing, and provide the opacity at the sides and waist to prevent the skin of the user from showing through the article.

Figure 24:
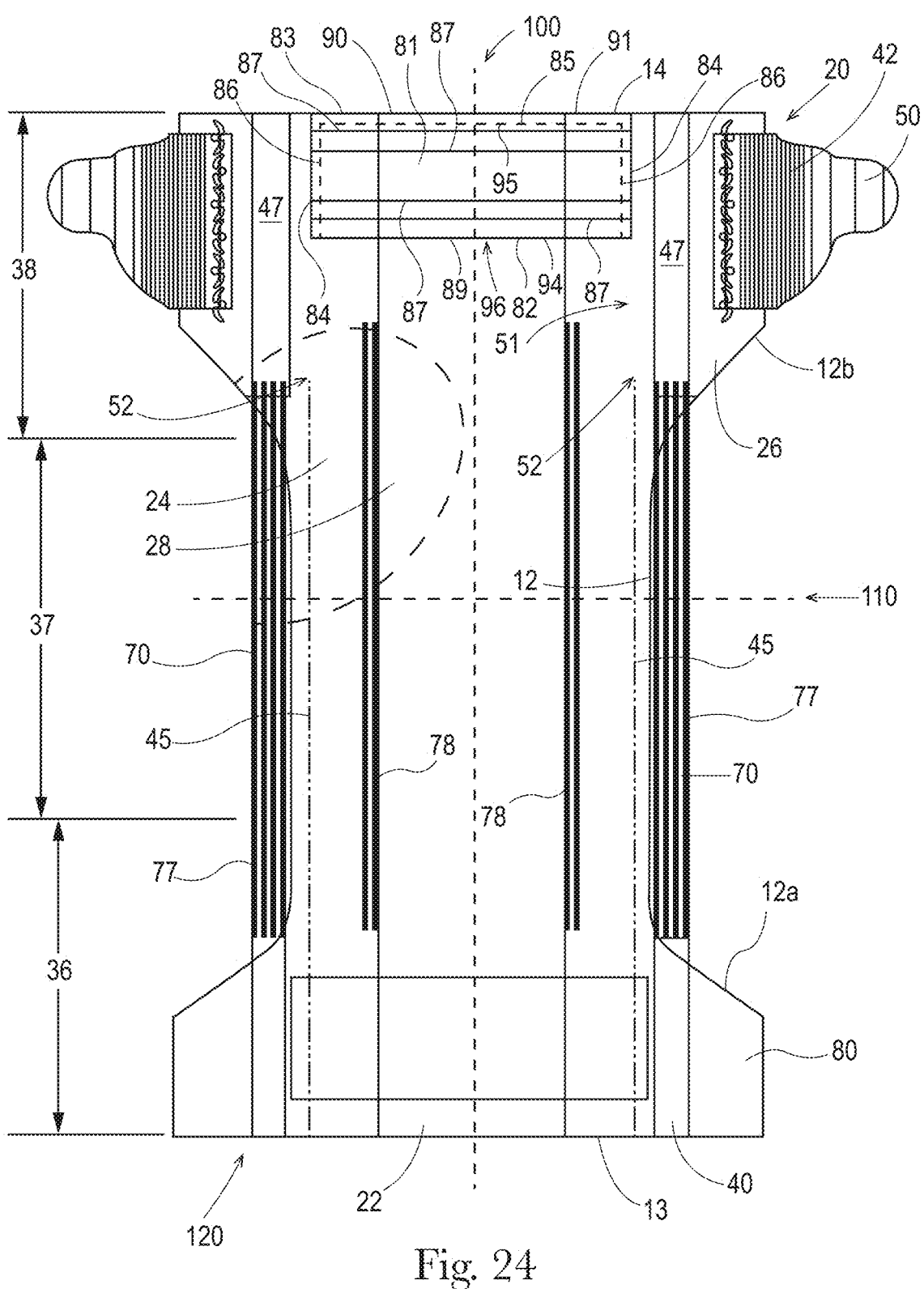
FIG. 24 is a schematic plan view of an exemplary embodiment of an absorbent article as detailed herein.

FIGS. 1 and 24 are plan views of exemplary, non-limiting embodiments of the absorbent article described herein in a flat, uncontracted state. FIGS. 1 and 24 illustrate substantially the same disposable absorbent article, with the difference being that FIG. 24 also incorporates a waist gasketing element 81 in the second waist region 38. Accordingly, when detailing the particular elements of the embodiment of FIG. 1 herein, the same disclosure will also apply to the embodiment of FIG. 24, as those same elements may also be present in the embodiment of FIG. 24 (whether explicitly shown or not). Due to clarity issues, some of the elements that are explicitly shown and referenced in FIG. 1 may appear missing from FIG. 24. For instance, the cuff separation bonds 45 are not explicitly shown in outboard part of the second waist region 38 of FIG. 24 due to providing clarity to the illustration of the waist gasketing element 81. However, even though not explicitly illustrated, the embodiment of FIG. 24 may include cuff separation bonds 45 in that region as detailed in FIG. 1 and described herein, as well as any other elements illustrated in FIG. 1 (or the figures that reference FIG. 1) and/or described herein.

The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements such that they gather about the waist of the wearer to provide improved fit and containment. The crotch region 37 is the portion of the absorbent article 20 which, when absorbent article 20 is worn, is generally positioned between the legs of the wearer.

The outer periphery of chassis 22 is defined by longitudinal edges 12 and waist edges (first waist edge 13 in first waist region 36 and second waist edge 14 in second waist region 38). The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape diaper when viewed in a plan view. The chassis 22 may have opposing lateral edges 14 that are oriented generally parallel to the lateral centerline 110.

The chassis 22 may comprise a liquid permeable topsheet 24, a backsheet 26, and an absorbent core 28 between the topsheet 24 and the backsheet 26. In embodiments that include one or more opacity strengthening patches 80, the chassis 22 also comprises the opacity strengthening patch(s). The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the absorbent article 20 with other features may be added to form the composite absorbent article structure. While the topsheet 24, the backsheet 26, and the absorbent core 28 may be assembled in a variety of well-known configurations, preferred absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, TN as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

Backsheet:

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, IN and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, TX, under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In certain embodiments the ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the non-woven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, VA, as supplier code X25007) disposed between two nonwoven layers (such as is available from BBA Fiberweb, Brentwood, TN as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the rear waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Figures 2, 3:
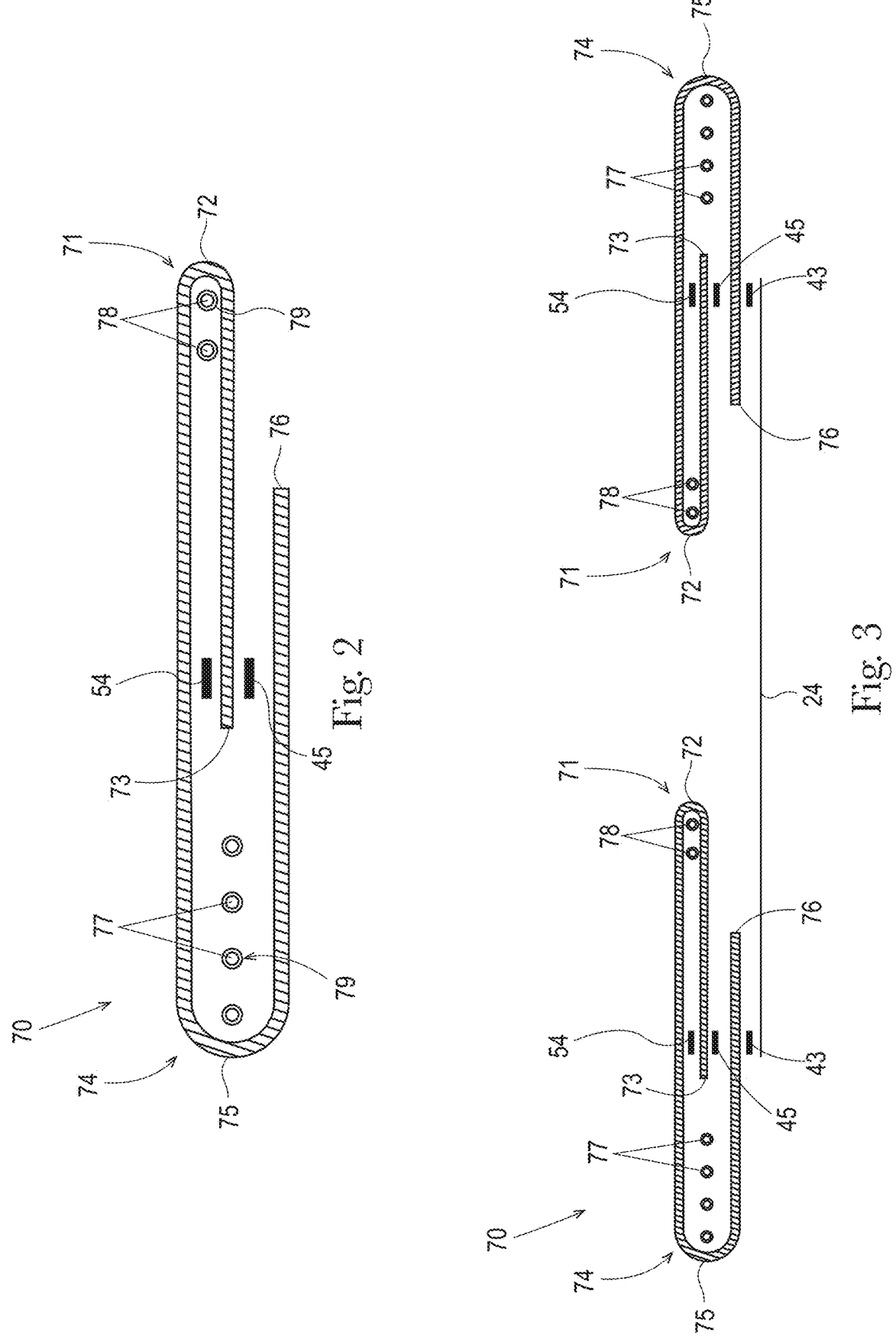
FIG. 2 is a schematic cross sectional view of an exemplary embodiment of one of the leg gasketing systems of FIG. 1, taken along the lateral centerline. The leg gasketing system is shown in a flat, uncontracted state.
FIG. 3 is a schematic cross sectional view of an exemplary embodiment of the leg gasketing systems and topsheet of FIG. 1, the cross section taken along the lateral centerline. The leg gasketing systems are shown in a flat, uncontracted state.

Leg Gasketing System:

The absorbent article 20 may include a leg gasketing system 70 that is attached to the chassis 22. FIGS. 2 and 3 depict schematic cross sectional views of the exemplary leg gasketing systems of FIG. 1 in a flat, uncontracted state, the views taken through the lateral centerline 110 (FIG. 2 is a schematic cross section of the left leg gasketing system, and FIG. 3 is a schematic cross section of both leg gasketing systems in relation to the topsheet). FIGS. 4-15 also depict schematic cross sectional views of the exemplary leg gasketing system 70 of FIG. 1. FIGS. 4-9 are cross sections of embodiments of the disposable absorbent article of FIG. 1 without an opacity strengthening patch 80, and FIGS. 10-15 are cross sections of embodiments of the disposable absorbent article of FIG. 1 with an opacity strengthening patch 80. In the embodiments of FIGS. 10-15, the opacity strengthening patches 80 are located in the four corners of the diaper chassis 22, overlapping portions of both the polymeric film inner layer of the backsheet 26 and the ears 40, 42. FIGS. 4, 7, 10 and 13 are schematic cross sectional views through line A-A of FIG. 1. FIGS. 5, 8, 11 and 14 are schematic cross sectional views through line B-B of FIG. 1. FIGS. 6, 9, 12 and 15 are schematic cross sectional views through line C-C of FIG. 1. In the various embodiments, the leg gasketing system 70 may include an inner cuff 71 that has an inner cuff folded edge 72 and an inner cuff material edge 73. The leg gasketing system 70 may further include an outer cuff 74 that has an outer cuff folded edge 75 and an outer cuff material edge 76.

In some embodiments, each leg gasketing system 70 comprises a single, continuous web of material. An embodiment having a single web of material may provide a cost advantage over embodiments having more than one web of material. Further, a leg gasketing system formed from one web of material may have fewer leaks, as there are no holes created by bonding more than one web of material. Also, an embodiment having one web of material may be more aesthetically pleasing, as few mechanical bonds are visible. In other embodiments, the leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing system embodiments that may be formed from a single, continuous web of material, multiple webs of material that are joined together to become one web of material, or multiple distinct webs of material that are separate from the disposable absorbent article chassis and form part of the leg gasketing system. All such embodiments are contemplated.

In one embodiment, the leg gasketing system 70 includes an inner cuff 71 that has an inner cuff folded edge 72 and an inner cuff material edge 73. The leg gasketing system 70 may further include an outer cuff 74 that has an outer cuff folded edge 75 and an outer cuff material edge 76. In some embodiments, the web of material is folded laterally inward (toward the longitudinal centerline 100 of the absorbent article 20) to form the outer cuff folded edge 75 and folded laterally outward (away from the longitudinal centerline 100 of the absorbent article 20) to form the inner cuff folded edge 72.

In one embodiment, at least a portion of the web of material between the outer cuff folded edge 75 and the outer cuff material edge 76 is attached to the chassis 22 (e.g., the topsheet 24, the backsheet 26, and/or the opacity strengthening patch 80) in the first waist region 36, the second waist region 38 and the crotch region 37. The attachment to the chassis 22 is made through utilization of one or more cuff attachment bonds 43, 44. In one embodiment, one or more of the cuff attachment bonds 43, 44 are continuous, or substantially continuous (e.g., in a continuously intermittent pattern) from the first waist edge 13 to the second waist edge 14. As seen in the exemplary embodiments of FIGS. 3-9, a first cuff attachment bond 43 attaches at least a portion of the web of material between the outer cuff folded edge 75 and the outer cuff material edge 76 to the topsheet 24. And a second cuff attachment bond 44 attaches at least a portion of the web of material between the outer cuff folded edge 75 and the outer cuff material edge 76 to the backsheet 26. In FIGS. 3-9, a single first cuff attachment bond 43 and two second cuff attachment bonds 44 are shown, but embodiments having multiple first cuff attachment bonds 43 and/or single or multiple second cuff attachment bonds 44 are contemplated. As seen in the exemplary embodiment of FIGS. 10-15, a first cuff attachment bond 43 attaches at least a portion of the web of material between the outer cuff folded edge 75 and the outer cuff material edge 76 to the topsheet 24. And at least one second cuff attachment bond 44 attaches at least a portion of the web of material between the outer cuff folded edge 75 and the outer cuff material edge 76 to the opacity strengthening patch 80 in at least a portion of the first waist region 36 and at least a portion of the second waist region 38. The opacity strengthening patch is attached to the backsheet 26 (inner or outer backsheet layer) by at least one OSP bond(s) 46. In the crotch region 37 and in a portion of the first waist region 36 and in a portion of the second waist region 38, at least a portion of the web of material between the outer cuff folded edge 75 and the outer cuff material edge 76 is attached to the backsheet 26 (inner or outer backsheet layer) through cuff attachment bond 44. In other words, from first waist edge 13 to second waist edge 14, at least a portion of the web of material between the outer cuff folded edge 75 and the outer cuff material edge 76 is attached to either the backsheet 26 or to the opacity strengthening patch 80 through continuous or substantially continuous second cuff attachment bond(s) 44. In FIGS. 10-15, a single first cuff attachment bond 43 and two second cuff attachment bonds 44 are shown, but embodiments having multiple first cuff attachment bonds 43 and/or a single or multiple second cuff attachment bonds 44 are contemplated. The cuff attachment bonds 43, 44 and the OSP bonds 46 may take the form of glue, heat bond, pressure bond, CPW bond, or any other bonding method known in the art. In the exemplary embodiments of FIGS. 3-15, the cuff attachment bonds 43, 44 and the OSP bonds 46 take the form of a glue bond.

In some embodiments, at least a portion of the web of material between the inner cuff folded edge 72 and the inner cuff material edge 73 is attached to the at least a portion of the web of material between the inner cuff folded edge 72 and the outer cuff folded edge 75. The attachment is made through utilization of one or more inner cuff bonds 54. In one embodiment, one or more of the inner cuff bonds 54 are continuous, or substantially continuous (e.g., in a continuously intermittent pattern) from the first waist edge 13 to the second waist edge 14. As seen in the exemplary embodiments of FIGS. 3-6 and 10-12, the inner cuff bond 54 attaches at least a portion of the web of material between the inner cuff folded edge 72 and the inner cuff material edge 73 to at least a portion of the web of material between the inner cuff folded edge 72 and the outer cuff folded edge 75. The inner cuff bonds 54 may take the form of glue, heat bond, pressure bond, CPW bond, or any other bonding method known in the art. In the exemplary embodiments of FIGS. 3-6 and 10-12, the inner cuff bonds 54 take the form of a glue bond. Some embodiments include inner cuff bonds 54 that are made by pressure bonding and/or CPW bonding.

Further, at least a portion of the web of material between the inner cuff folded edge 72 and the inner cuff material edge 73 is attached to at least a portion of the web of material between the outer cuff folded edge 75 and the outer cuff material edge 76 in at least the crotch region 37 and the first waist region 36. The attachment of the web of material between the inner cuff folded edge 72 and the inner cuff material edge 73 to the web of material between the outer cuff folded edge 75 and the outer cuff material edge 76 in at least the crotch region 37 and the first waist region 36 is made through utilization of one or more cuff separation bonds 45. As seen in FIGS. 1-15, the cuff separation bond attaches at least a portion of the web material between the inner cuff folded edge 72 and the inner cuff material edge 73 to the web of material between the outer cuff folded edge 75 and the outer cuff material edge 76 in the crotch region 37, the first waist region 36, and a portion of the second waist region 38. The cuff separation bond 45 may take the form of glue, heat bond, pressure bond, CPW bond, or any other bonding method known in the art. In the exemplary embodiments of FIGS. 3-15, the cuff separation bond 45 takes the form of a glue bond.

As illustrated in FIGS. 1 and 4-15, the web of material between the inner cuff folded edge 72 and the inner cuff material edge 73 is unattached to the web of material between the outer cuff folded edge 75 and the outer cuff material edge 76 in at least a portion of the second waist region 38. Due to the web of material between the inner cuff folded edge 72 and the inner cuff material edge 73 being unattached to the web of material between the outer cuff folded edge 75 and the outer cuff material edge 76 in at least a portion of the second waist region 38, a leg gasketing system pocket 47 is formed in at least a portion of the second waist region of the leg gasketing system 70. The leg gasketing system pocket 47 includes an inboard longitudinal edge 48 and an outboard longitudinal edge 49, which define lateral dimensions of the leg gasketing system pocket. In some embodiments, the inboard longitudinal edge 48 of the leg gasketing system pocket 47 is coterminous with a line that the cuff separation bond 45 runs along in the longitudinal direction. In some embodiments, the outboard longitudinal edge 49 is coterminous with the outer cuff folded edge 75. In another embodiment, the outboard longitudinal edge 49 is coterminous with the most outboard bond of the outer cuff 74.

In one embodiment, the leg gasketing system pocket 47 includes an opening 51 which runs a distance along the inboard longitudinal edge 48 of the leg gasketing system pocket 47. The opening 51 is created by a break in the cuff separation bond 45. Referring to FIG. 1, the cuff separation bond 45 runs in the longitudinal direction of the absorbent article, and is continuous, or substantially continuous (e.g., in a continuously intermittent pattern) in the first waist region 36 and the crotch region 37. The continuous cuff separation bond 45 continues into the second waist region 38, but then stops for a defined distance and then starts again along the same longitudinal line. The distance in which the cuff separation bond 45 stops along that longitudinal line is the distance in which the web material between the inner cuff folded edge 72 and the inner cuff material edge 73 is unattached to the web of material between the outer cuff folded edge 75 and the outer cuff material edge 76. Accordingly, this distance is the length of the opening 51 which runs along the inboard longitudinal edge 48 of the leg gasketing system pocket 47. The opening 51 has an inboard lateral edge 52 and an outboard lateral edge 53 where the cuff separation bond 45 starts and stops along the longitudinal line that the cuff separation bond 45 runs along. As illustrated in FIG. 1, the length of the opening 51 can be determined by measuring the distance between inboard lateral edge 52 and outboard lateral edge 53, taken along the longitudinal line that the cuff separation bond 45 runs along.

In another embodiment, the leg gasketing system pocket 47 includes an opening 51 which again runs a distance along the inboard longitudinal edge 48 of the leg gasketing system pocket 47. The opening 51 is created by a series of breaks in the cuff separation bond 45. Referring to FIG. 1, the cuff separation bond 45 runs in the longitudinal direction of the absorbent article, and is continuous in the first waist region 36 and the crotch region 37. The continuous cuff separation bond 45 continues into the second waist region 38, but then becomes an intermittent bond pattern (e.g., stop-start-stop-start) for a defined distance and then becomes continuous again along the same longitudinal line. The distance in which the cuff separation bond 45 becomes an intermittent bond pattern along that longitudinal line is the distance in which the web material between the inner cuff folded edge 72 and the inner cuff material edge 73 is intermittently attached to the web of material between the outer cuff folded edge 75 and the outer cuff material edge 76. This intermittent pattern for a distance of the cuff separation bond 45 creates series of small pockets, together referred to herein as a leg gasketing system pocket.

In other embodiments, the pocket and opening can occur in the first waist region, the second waist region, or in the crotch region as needed for the specific type of exudates and the particular situation where leakage prevention is desired. For instance, a wearer who sleeps on their belly (front) may benefit from the pocket and opening being located in the front waist region, as to stop urine leakage out of the front waist during sleep. Likewise, it may be important to create the opening on the crotch region for users wearing the article in the standing position as to contain exudates that are likely to locate centrally in the article due to the force of gravity when in a standing position.

In some embodiments, the opening 51 measures between about 5 mm and about 100 mm in the longitudinal direction, or any range or distance within the range of about 5 mm to about 100 mm; in some embodiments the opening measures about 75 mm or about 50 mm; and in other embodiments the opening measures between about 1 mm and about 20 mm. In one embodiment, the length of opening 51 is between about 1% and about 75% of the overall longitudinal length of the leg gasketing system pocket 47 (or any range or percentage within the range of about 1% to about 75%). The overall longitudinal length of the leg gasketing system pocket 47 is the distance from the furthest longitudinally inboard portion of the pocket to the furthest longitudinally outboard position of the pocket. In some embodiments, the furthest longitudinally outboard position of the pocket 47 is the second waist edge of absorbent article, and in other embodiments, the pocket 47 may end longitudinally short of the second waist edge. For the embodiment shown in FIG. 1, the overall longitudinal length of the leg gasketing system pocket 47 is the distance from the inboard lateral edge 52 of the opening 51 to the second waist edge 14 of the absorbent article 20, taken along the longitudinal line that the cuff separation bond 45 runs along. In other words, for the exemplary embodiment shown in FIG. 1, the longitudinal dimensions of the leg gasketing system pocket 47 are defined by the inboard lateral edge 52 of the opening 51 and the second waist edge 14. In one embodiment, the overall longitudinal length of the leg gasketing system pocket 47 measures between about 5 mm and about 200 mm in the longitudinal direction, or any range or distance within the range of about 5 mm to about 200 mm; in some embodiments, about 100 mm, about 75 mm, or about 50 mm; and in other embodiments the overall longitudinal length measures between about 1 mm and about 20 mm. In one embodiment, the outboard edge of the opening 51 of the leg gasketing system pocket 47 is positioned about 5 mm inboard from the second waist edge 14 in the longitudinal direction and the inboard edge of the opening is positioned about 100 mm inboard from the second waist edge 14 in the longitudinal direction. In other embodiments, the inboard/outboard edges of the opening can be any range or distance within the range of about 5 mm to about 200 mm inboard from the second waist edge 14 in the longitudinal direction; in some embodiments, the outboard edge of the opening is about 100 mm, about 75 mm, about 50 mm, about 20 mm, or about 1 mm inboard from the second waist edge 14 in the longitudinal direction; in some embodiments, the inboard edge of the opening is about 200 mm, about 100 mm, about 75 mm, about 50 mm or about 20 mm inboard from the second waist edge 14 in the longitudinal direction.

The overall lateral width of the leg gasketing system pocket 47 is the distance from the furthest laterally inboard portion of the pocket to the furthest laterally outboard portion of the pocket. For the embodiment shown in FIG. 1, the overall lateral width of the leg gasketing system pocket 47 is the distance from the inboard longitudinal edge 48 of the leg gasketing system pocket to the outboard longitudinal edge 49 of the leg gasketing system pocket, taken along a line that is parallel to the second waist edge 14 and centered in the middle of the opening 51 of the leg gasketing system pocket. In other words, for the exemplary embodiment shown in FIG. 1, the lateral dimension of the leg gasketing system pocket 47 (i.e., the width) is defined by inboard and outboard longitudinal edges 48, 49 of the leg gasketing system pocket 47. In one embodiment, the overall lateral width of the leg gasketing system pocket 47 measures between about 5 mm and about 60 mm in the lateral direction, or any range or distance within the range of about 5 mm to about 60 mm; in some embodiments, about 30 mm, about 25 mm, or about 20 mm; and in other embodiments, the overall lateral width measures between about 1 mm and about 20 mm. In one embodiment, the overall lateral width of the leg gasketing system pocket 47 is between about 1% and about 75% of the overall longitudinal length of the leg gasketing system pocket 47 (or any range or percentage within the range of about 1% to about 75%). In one embodiment, the length of opening 51 is between about 20% and about 100% of the overall lateral width of the leg gasketing system pocket 47 (or any range or percentage within the range of about 20% to about 100%).

When a wearer of an absorbent article has a runny bowel movement, many times the runny bowel movement spreads upon defecation and leaks out of the absorbent article in an area between the leg cuffs and wearer's legs, or in an area between the waist region and the wearer's back. Leaks of this type often happen because the snug fit between user's body and the attached absorbent article do not allow enough room for the runny bowel movement to remain contained within the absorbent article during the wearer's movement. One advantage of the leg gasketing system pocket 47 as detailed herein, in combination with the leg gasketing system(s) as detailed herein, are the additional pocketed areas that provide extra void volumes within the leg cuffs for containment of bodily extrudate (e.g., fecal material). When the wearer moves, a portion of the bodily extrudate will migrate into the leg gasketing system pocket 47 for containment and be held/trapped between two layers of nonwoven within the leg gasketing system before it can leak out in an area between the wearer's back and the back waist region of the absorbent article or an area between the leg cuffs and wearer's legs of the absorbent article. Thus, the leg gasketing system pocket 47 detailed herein reduces leaks. Moreover, leg gasketing system pocket 47 provides additional void volume within the leg cuffs to receive the fecal material which helps in isolating the fecal material from wearer's skin.

In one embodiment, the leg gasketing system pocket 47 is free of elastic members 77. In one embodiment, the leg gasketing system pocket 47 contains one or more snap back elastic members. In one embodiment, the leg gasketing system pocket 47 has a second opening 55 along the second waist edge 14 of the absorbent article. In one embodiment, the leg gasketing system pocket 47 is sealed along the second waist edge 14.

In one embodiment, at least a portion of the web of material between the outer cuff folded edge 75 and the outer cuff material edge 76 is attached to the chassis 22 (e.g., topsheet 24, backsheet 26, and/or opacity strengthening patch 80) in the first waist region 36, the second waist region 38 and the crotch region 37; and at least a portion of the web of material between the inner cuff folded edge 72 and the inner cuff material edge 73 is attached to the web of material between the outer cuff folded edge 75 and the outer cuff material edge 76 in the crotch region 37 and the first waist region 36; wherein the outer cuff includes an elastics adhesive 79 and at least one longitudinally oriented elastic member running parallel to the outer cuff folded edge 75, the elastics adhesive 79 and at least one elastic member disposed between 1) the web of material between the outer cuff folded edge 75 and the outer cuff material edge 76 and 2) the web of material between the outer cuff folded edge 75 and the inner cuff folded edge 72; wherein in at least a portion of the second waist region, the outer cuff is free of elastics adhesive 79 and elastic members 77, thus forming a leg gasketing system pocket 47 between 1) the web of material between the outer cuff folded edge 75 and the outer cuff material edge 76 and 2) the web of material between the outer cuff folded edge 75 and the inner cuff folded edge 72, the leg gasketing system pocket 47 having an outboard longitudinal edge 49 at the outer cuff folded edge 75; wherein the leg gasketing system pocket 47 comprises an opening 51 on an inboard longitudinal edge 48 of the leg gasketing system pocket.

In some embodiments, the pocket 47 includes a thermal or compression bond that defines at least a portion of the perimeter of the pocket (e.g., the entire perimeter of the pocket), such that the at least a portion of the pocket 47 (e.g., the entire pocket), can be made visible to a wearer or caregiver as to signal the functionality of the pocket 47 prior to use.

In some embodiments, the pocket 47 extends to the lateral edge of the chassis and creates channels for facilitating the flow of runny bowel movement. This open channel area can be sealed by any suitable bonding technique such as glue, mechanical bonds, thermal bonds, or the like.

In some embodiments, the pocket 47 can be used as an effective feature for a caregiver in applying the absorbent article easily on wearer. The pocket 47 can be used for inserting the fingers and spreading the absorbent article during application on the wearer, therefore providing ease of application. The lateral distance between the left and right pockets measures between about 120 mm and about 250 mm, or any range or distance within the range of about 120 mm to about 250 mm; in some embodiments, the lateral distance between the left and right pockets measures about 120 mm, about 150 mm, or about 200 mm; and in other embodiments the lateral distance between the left and right pockets is measured about 210 mm, or about 250 mm.

In another embodiment, the hydrophobic properties, such as Low Surface Tension Strikethrough or Hydro Head, can be increased in a least a portion of the pocket 47, in such a way that prevents exudates from leaking through the materials that comprise the pocket. Accordingly, this will maintain separation of the contained fecal material from the wearer. Increasing hydrophobic properties can be accomplished by applying hydrophobic coatings, inks, glues, silicones, additional materials, or any combination thereof, or by any other means known in the art. In one embodiment, the outer cuff 74 and inner cuff 71 are the same color. In one embodiment, the outer cuff 74 and inner cuff 71 are different colors. In one embodiment, there is an additional printing on one or more of the cuffs of the leg gasketing system 70. In embodiments with printing on both the inner and outer cuffs, the printing may be the same or different on each cuff.

In another embodiment, the leg gasketing system 70 includes a printed zone that outlines or defines at least a portion of the pocket 47 such that the benefit can be signaled prior to use.

Figure 4:
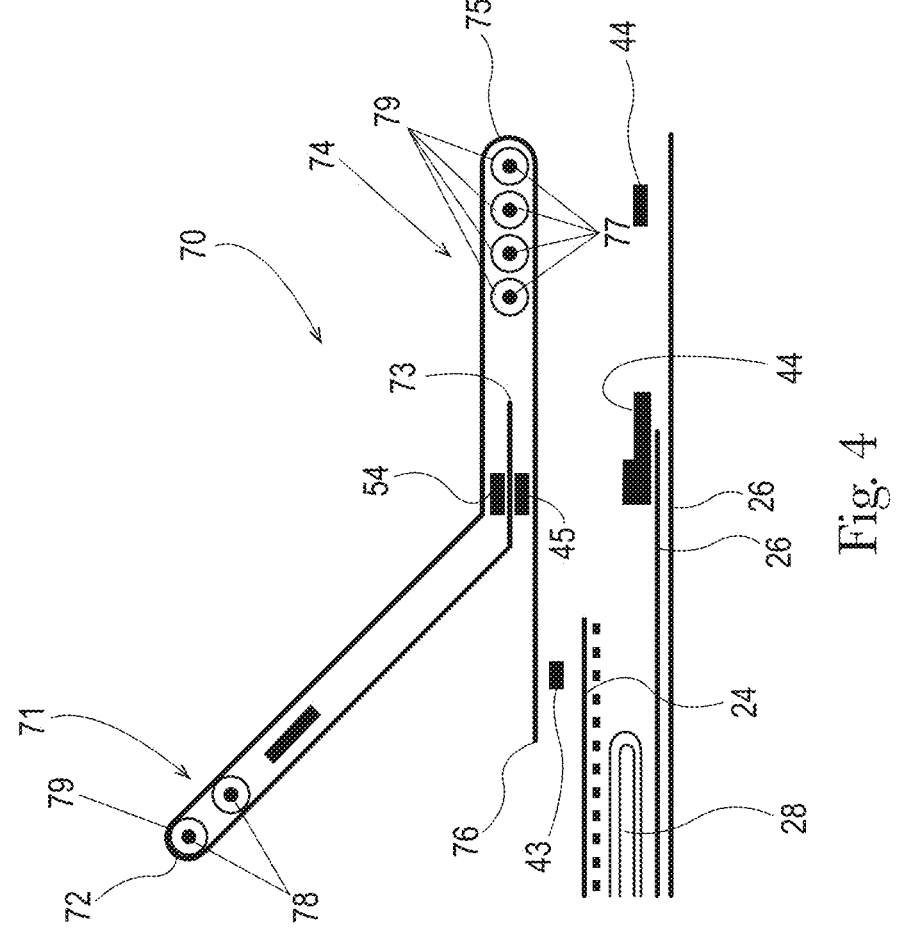
FIG. 4 is a schematic cross sectional view of an exemplary embodiment of the absorbent article of FIG. 1, the cross section taken along the line A-A.
Figure 5:
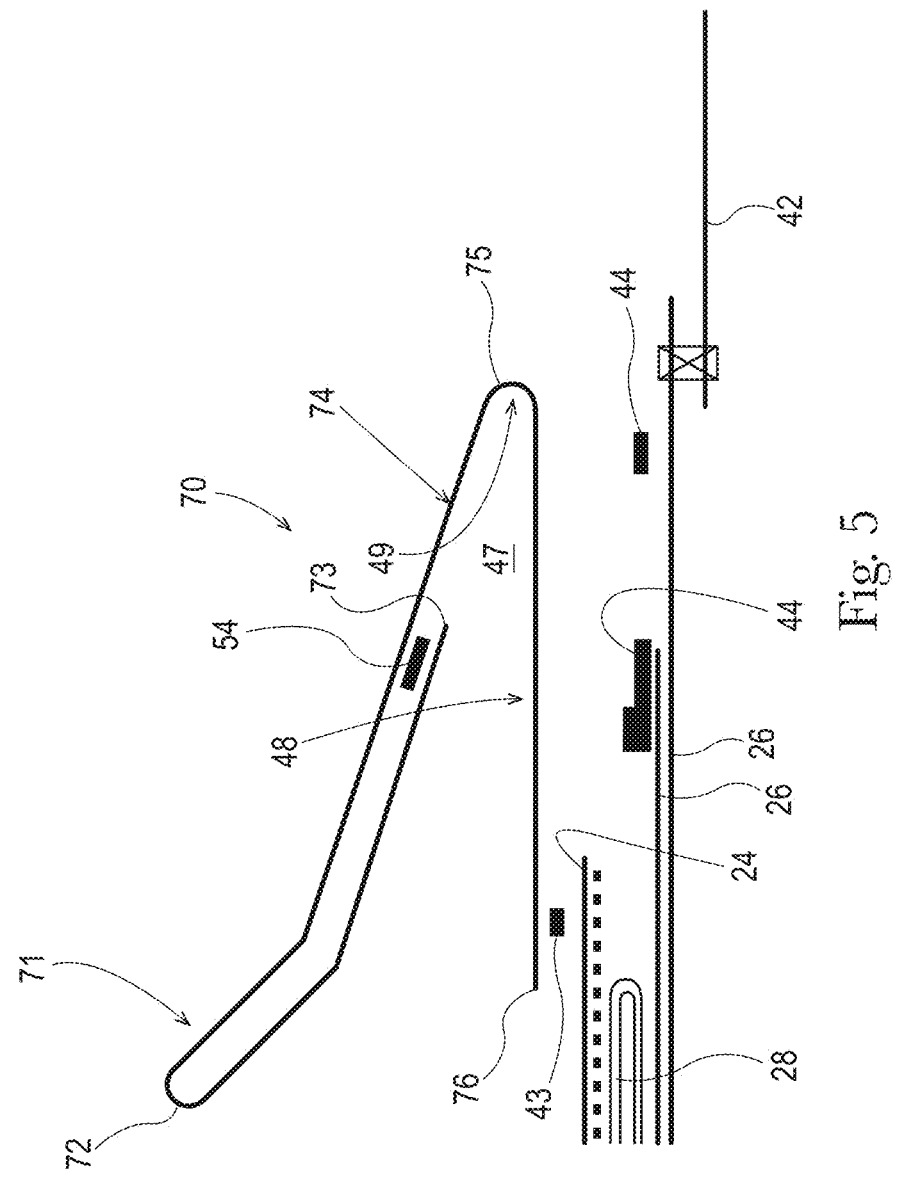
FIG. 5 is a schematic cross sectional view of an exemplary embodiment of the absorbent article of FIG. 1, the cross section taken along the line B-B.
Figure 6:
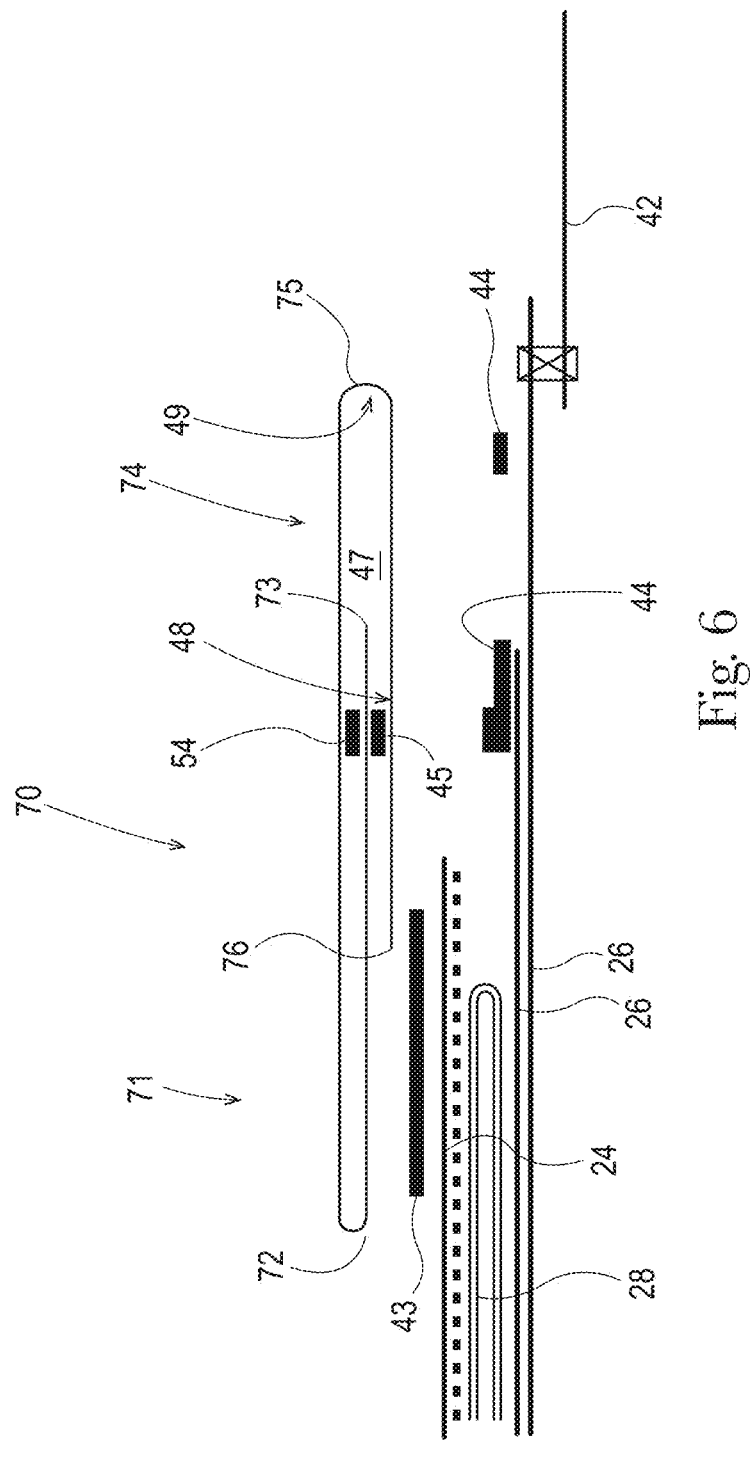
FIG. 6 is a schematic cross sectional view of an exemplary embodiment of the absorbent article of FIG. 1, the cross section taken along the line C-C.
Figure 7:
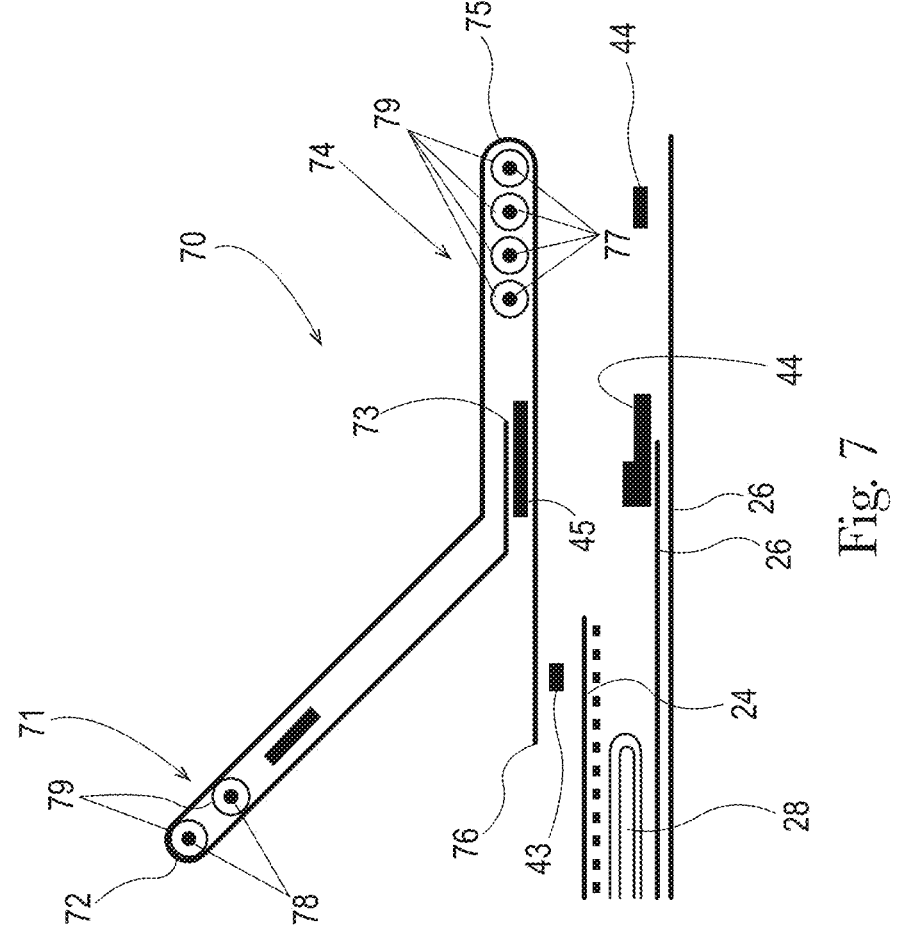
FIG. 7 is a schematic cross sectional view of an exemplary embodiment of the absorbent article of FIG. 1, the cross section taken along the line A-A.
Figure 8:
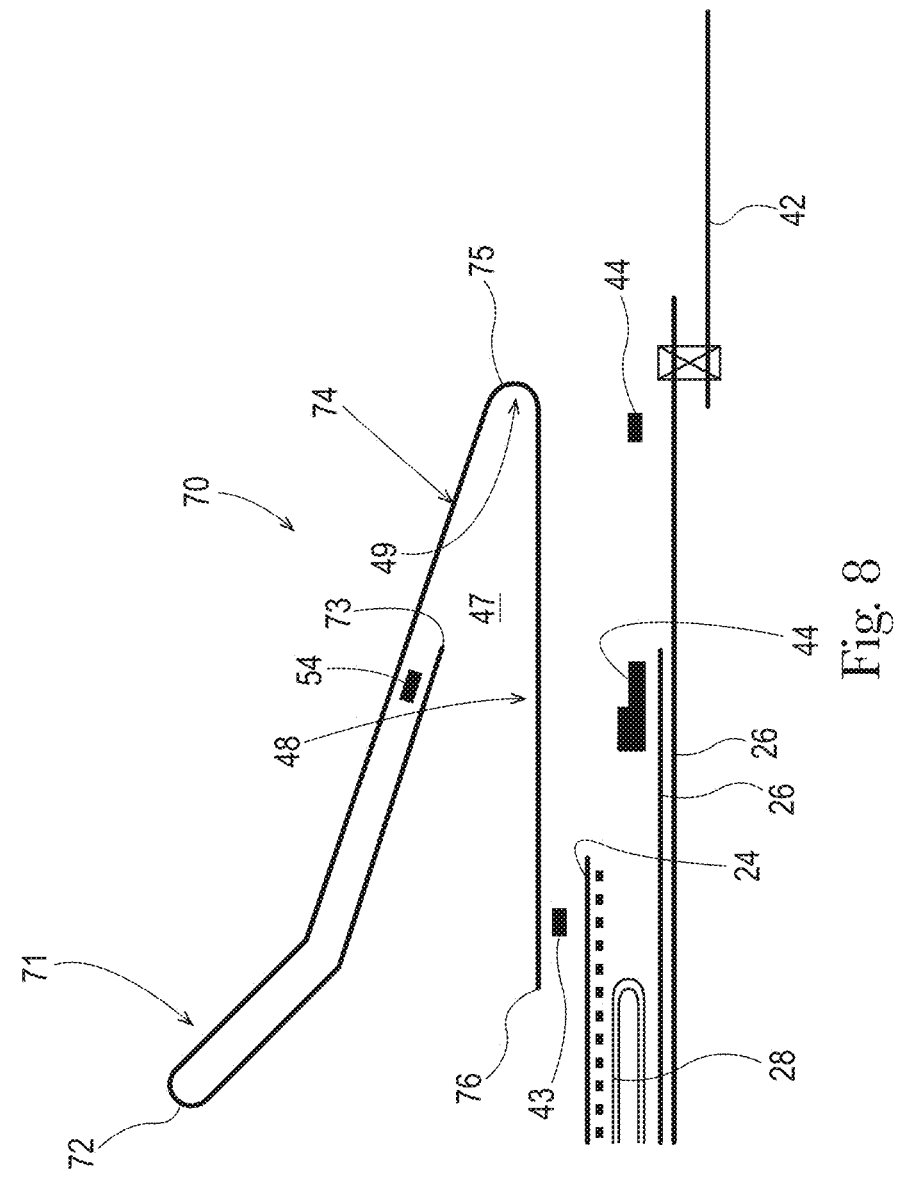
FIG. 8 is a schematic cross sectional view of an exemplary embodiment of the absorbent article of FIG. 1, the cross section taken along the line B-B.
Figure 9:
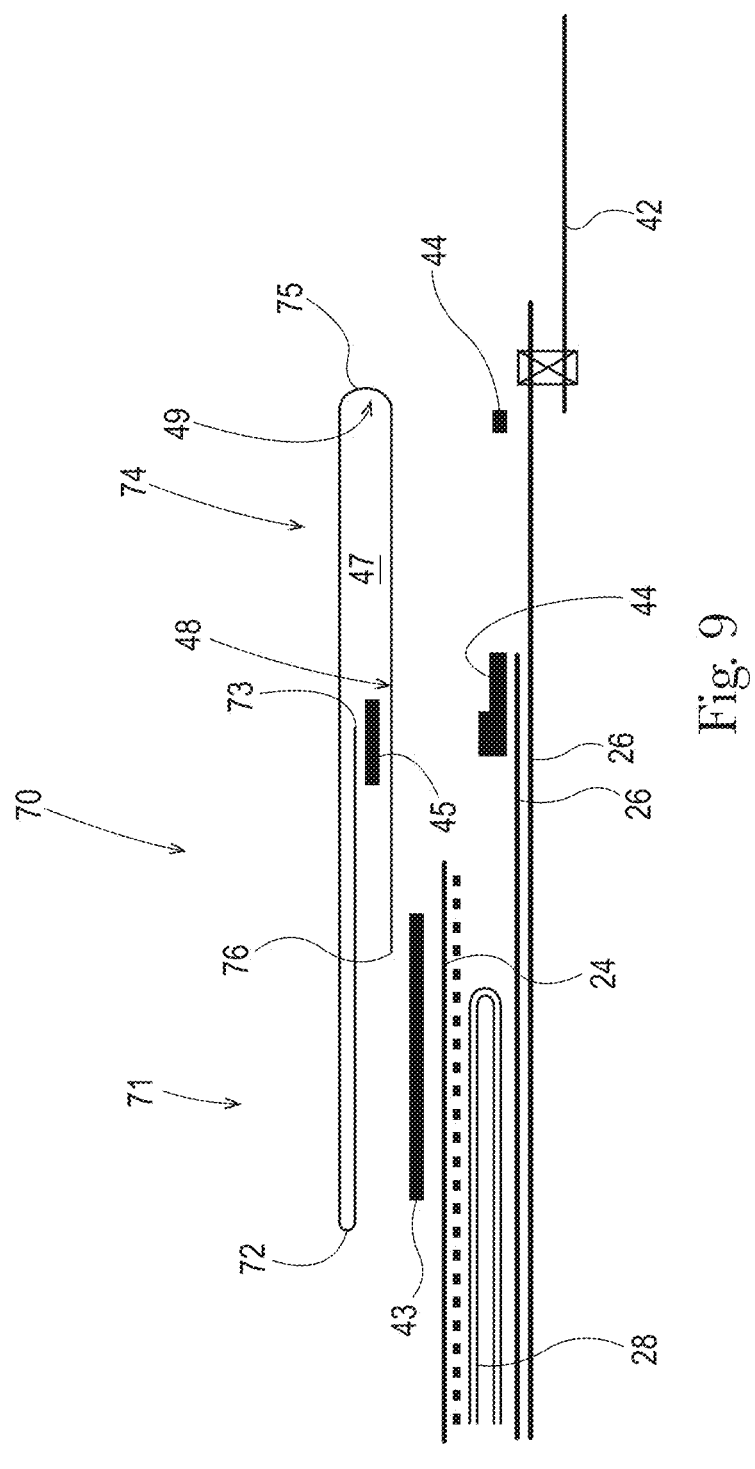
FIG. 9 is a schematic cross sectional view of an exemplary embodiment of the absorbent article of FIG. 1, the cross section taken along the line C-C.
Figure 10:
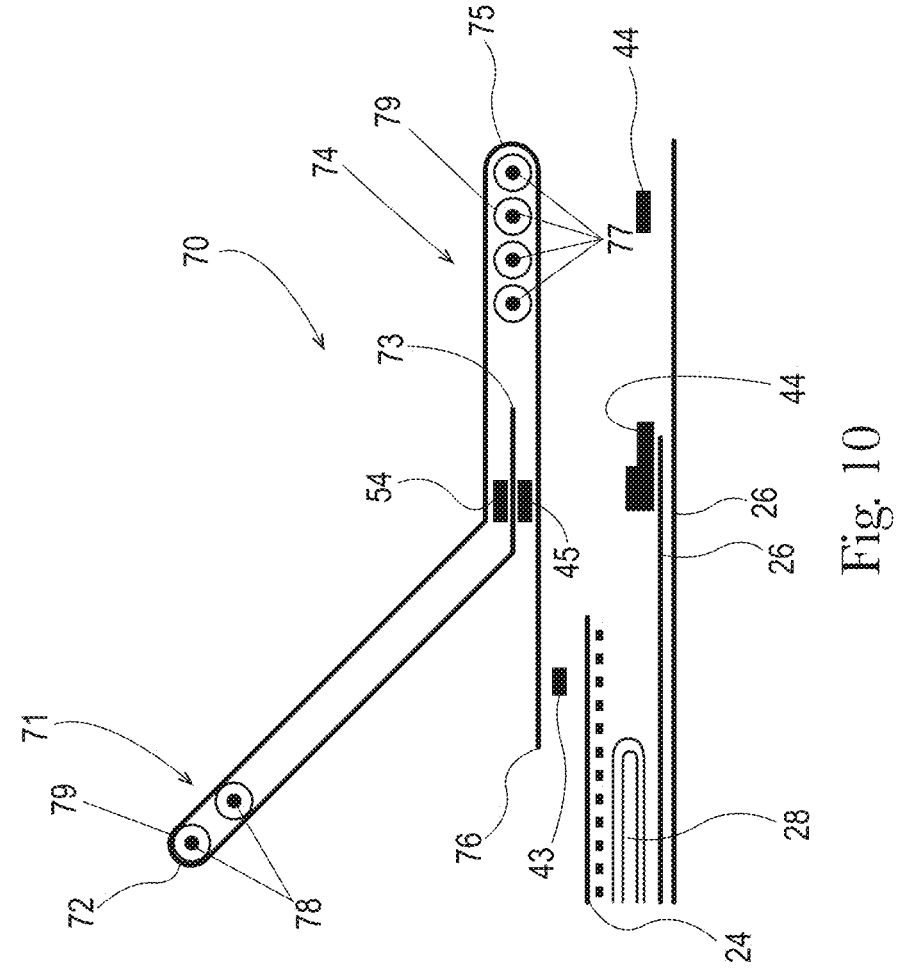
FIG. 10 is a schematic cross sectional view of an exemplary embodiment of the absorbent article of FIG. 1 with an opacity strengthening patch, the cross section taken along the line A-A.
Figure 11:
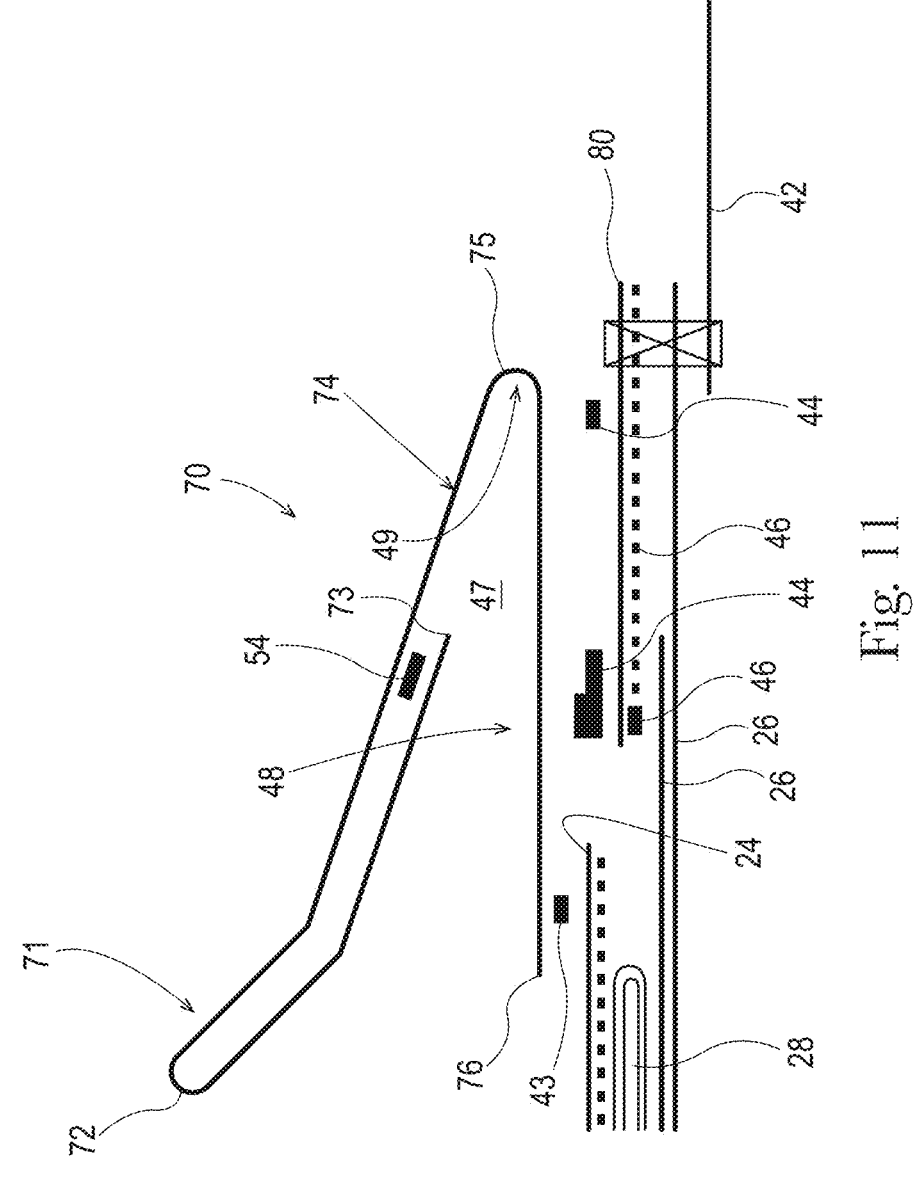
FIG. 11 is a schematic cross sectional view of an exemplary embodiment of the absorbent article of FIG. 1 with an opacity strengthening patch, the cross section taken along the line B-B.
Figure 12:
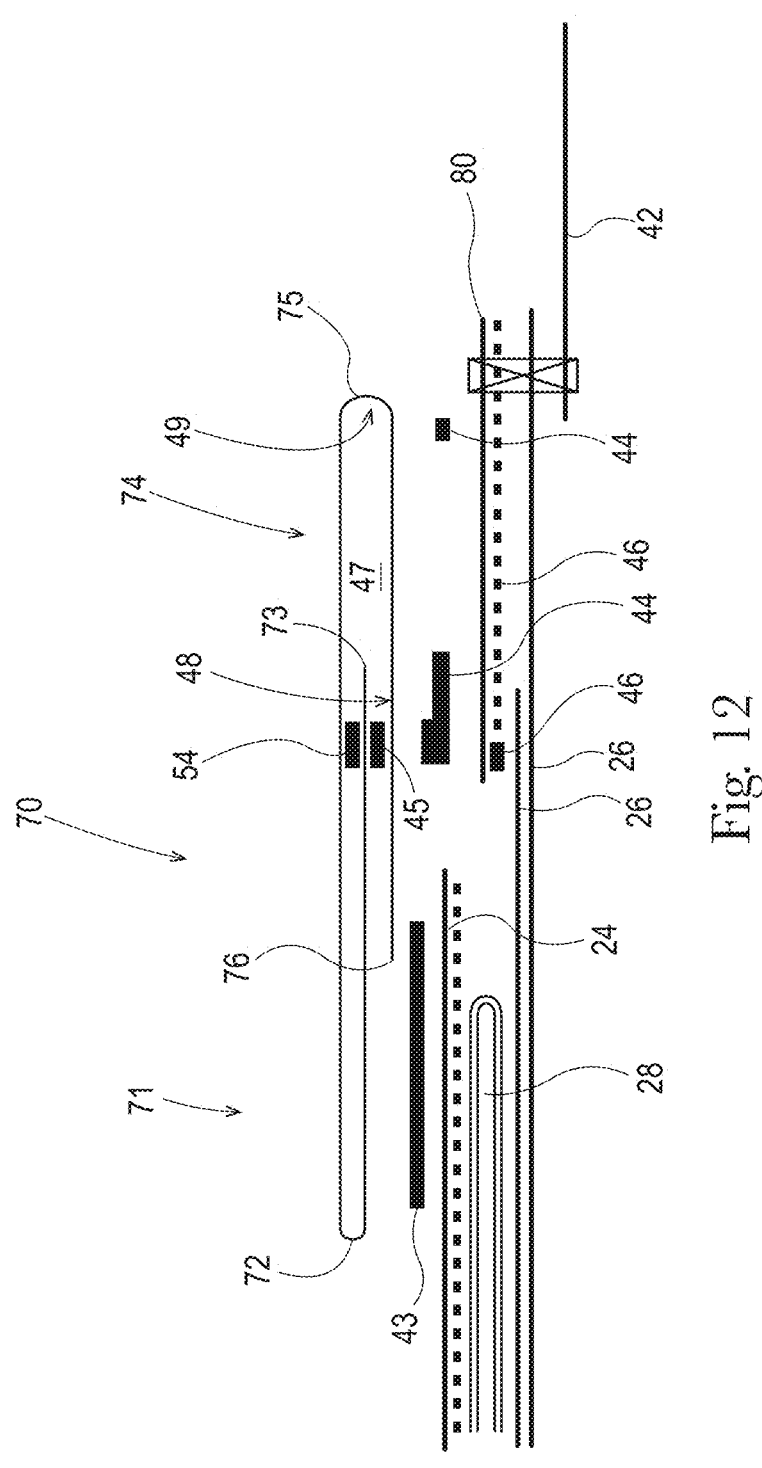
FIG. 12 is a schematic cross sectional view of an exemplary embodiment of the absorbent article of FIG. 1 with an opacity strengthening patch, the cross section taken along the line C-C.
Figure 13:
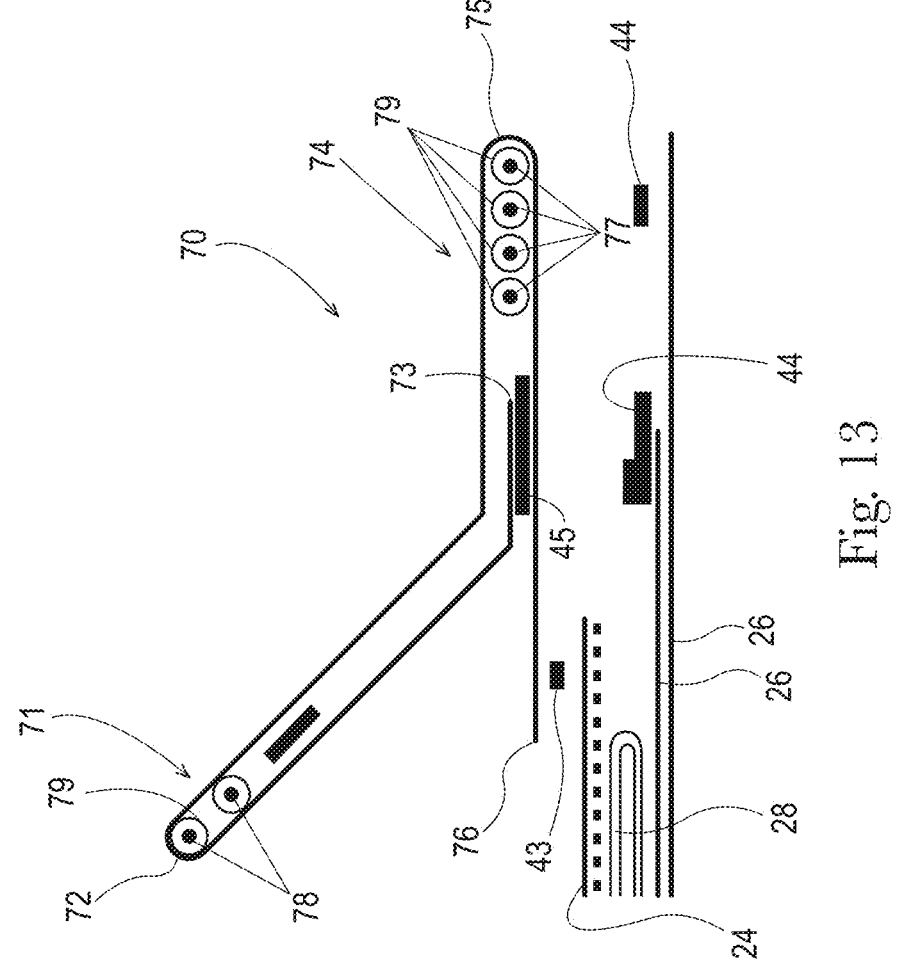
FIG. 13 is a schematic cross sectional view of an exemplary embodiment of the absorbent article of FIG. 1 with an opacity strengthening patch, the cross section taken along the line A-A.
Figure 14:
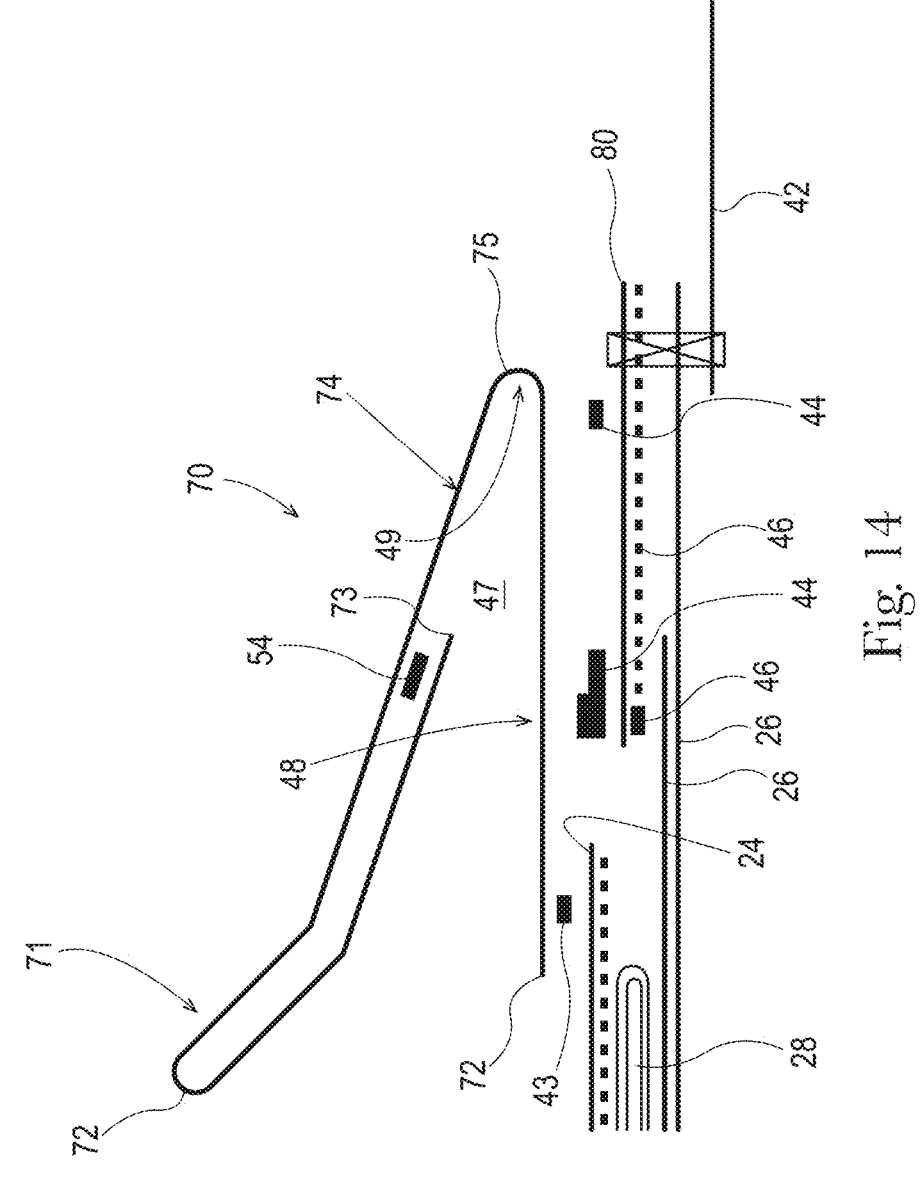
FIG. 14 is a schematic cross sectional view of an exemplary embodiment of the absorbent article of FIG. 1 with an opacity strengthening patch, the cross section taken along the line B-B.
Figure 15:
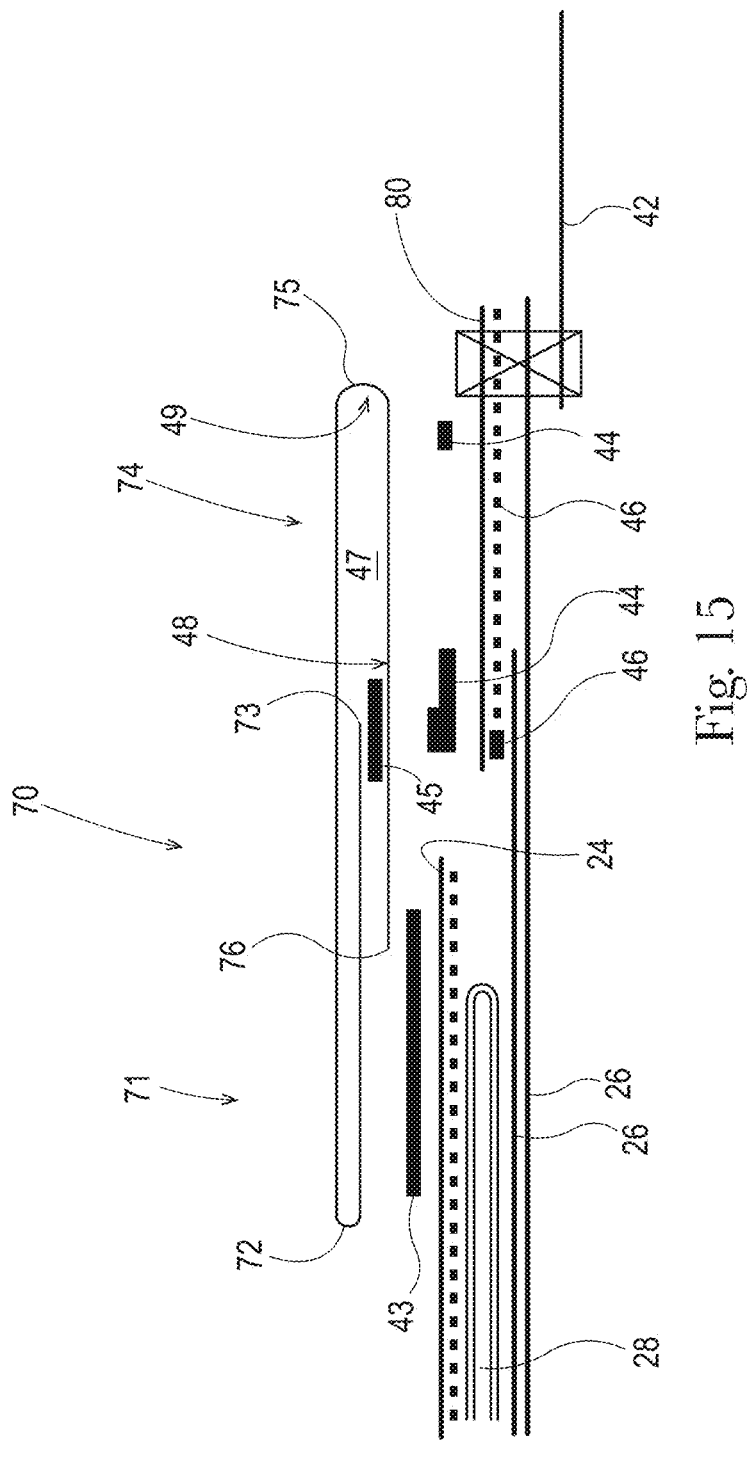
FIG. 15 is a schematic cross sectional view of an exemplary embodiment of the absorbent article of FIG. 1 with an opacity strengthening patch, the cross section taken along the line C-C.
Figure 16:
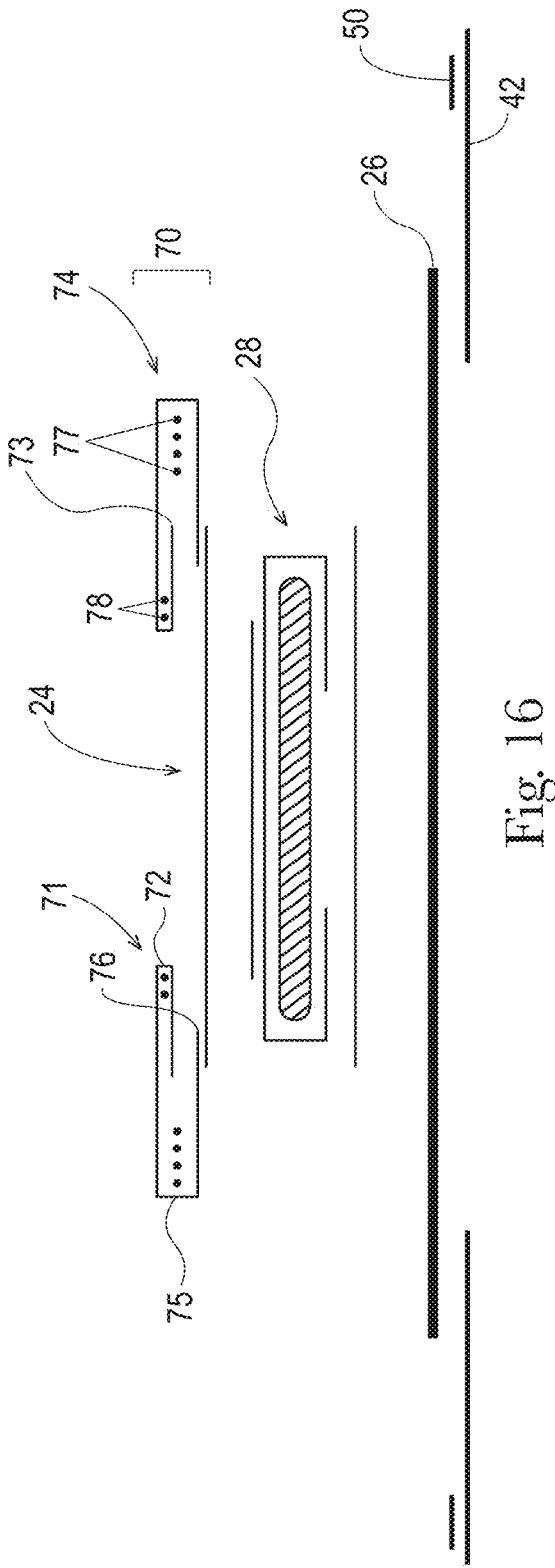
FIG. 16 is a schematic cross sectional view of an exemplary absorbent article as described herein.
Figures 17A, 17B, 17C, 17D, 17E, 17F, 17G, 17H:
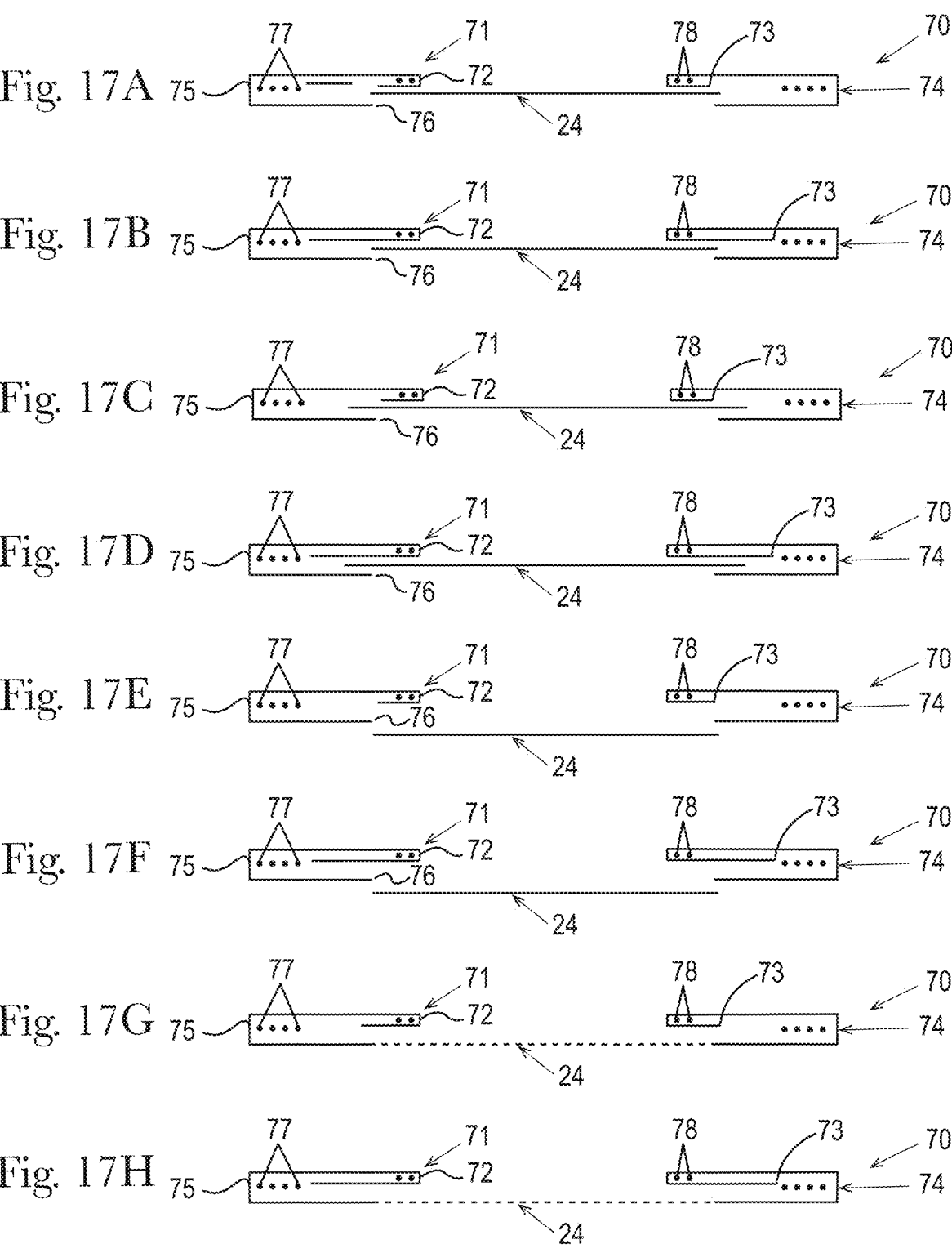
FIGS. 17a-t are schematic cross sectional views of additional exemplary embodiments of leg gasketing systems suitable for use in the embodiments of the absorbent articles detailed herein.
Figures 17I, 17J, 17K, 17L, 17M, 17N, 17O, 17P:
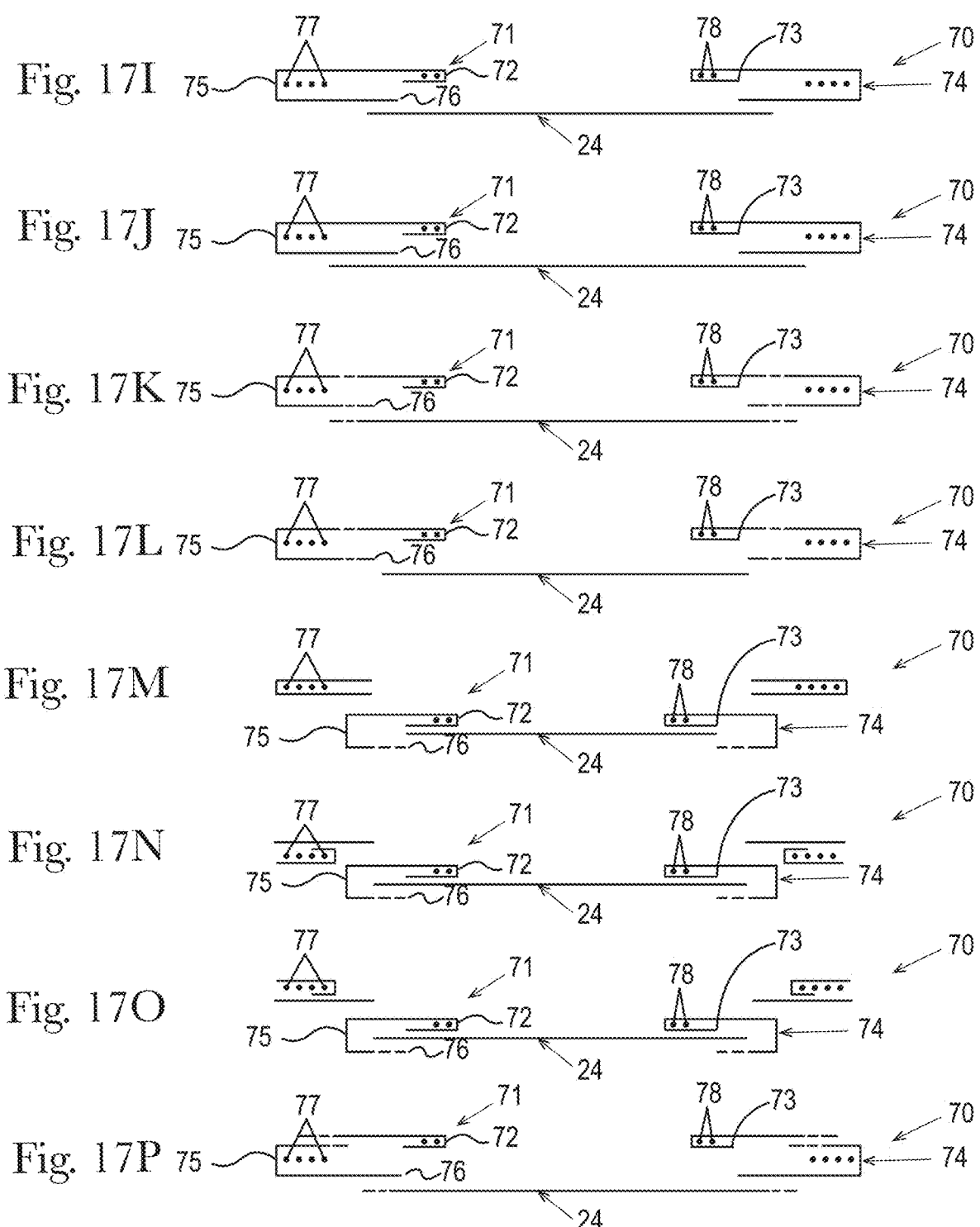
Figures 17Q, 17R, 17S, 17T:
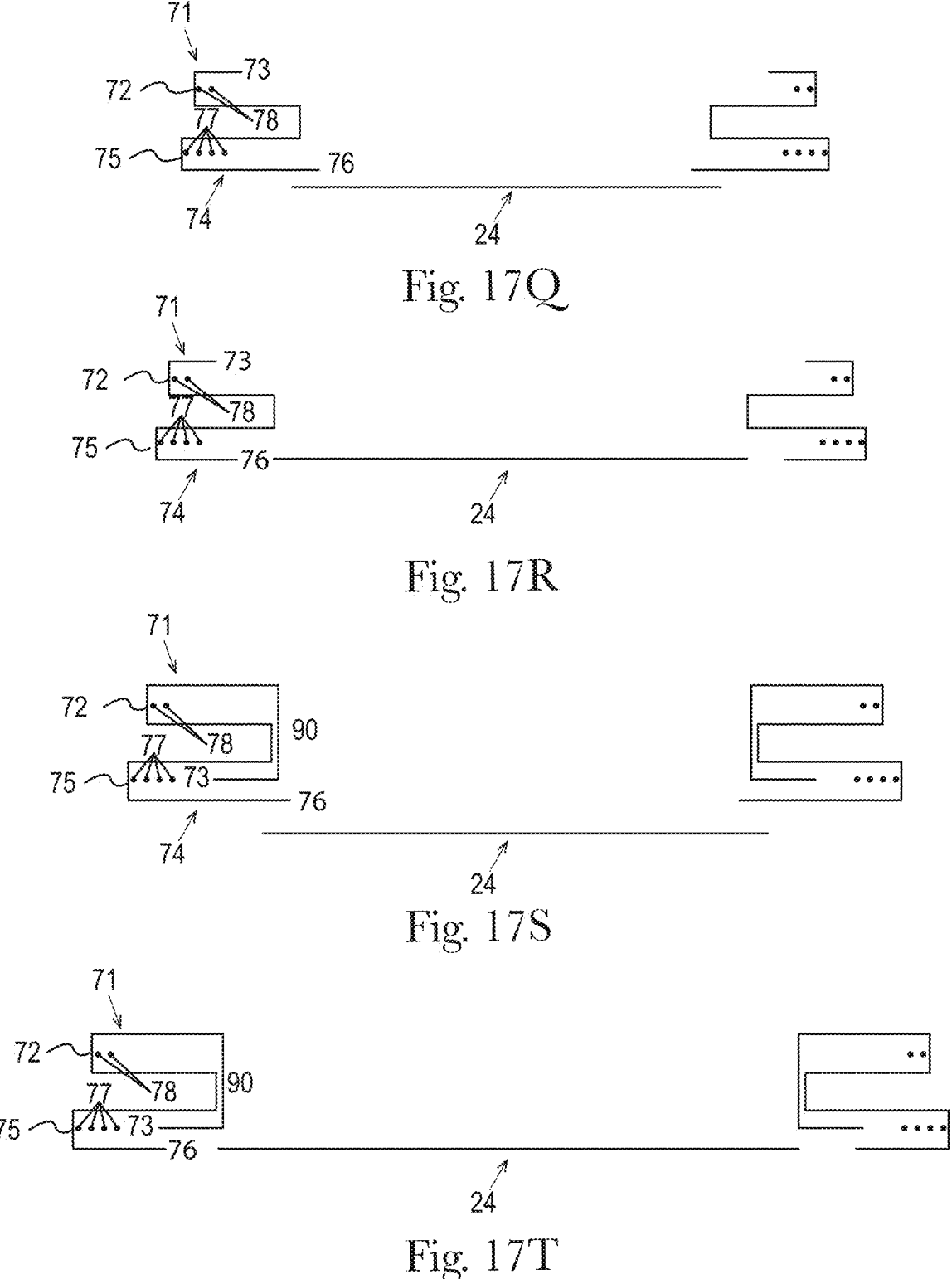
Figure 18:
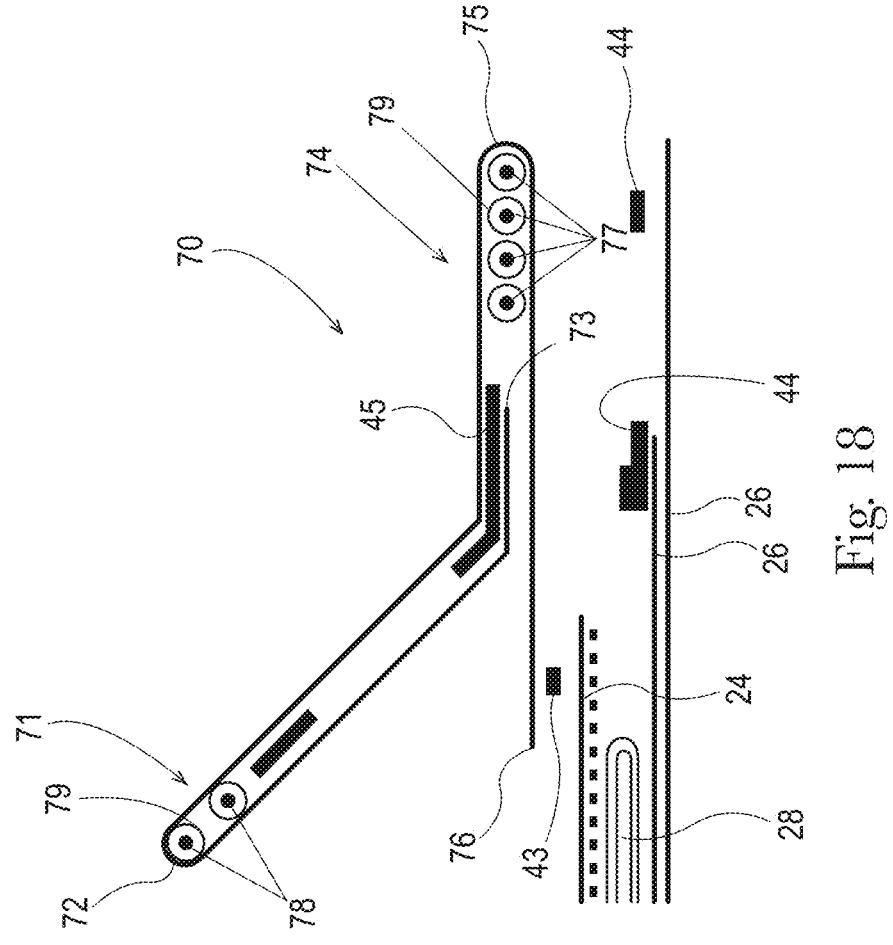
FIG. 18 is a schematic cross sectional view of an exemplary embodiment of the absorbent article of FIG. 1, the cross section taken along the line A-A.
Figure 19:
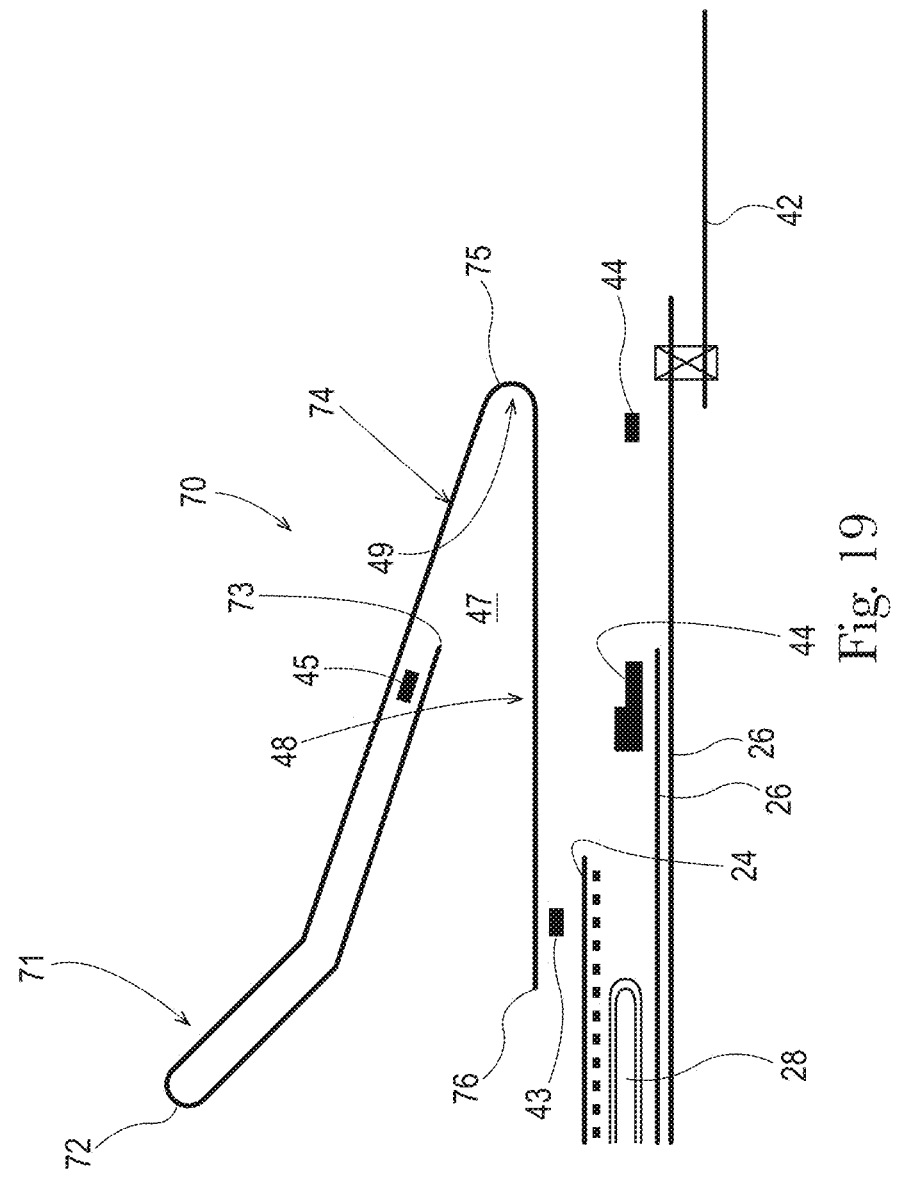
FIG. 19 is a schematic cross sectional view of an exemplary embodiment of the absorbent article of FIG. 1, the cross section taken along the line B-B.
Figure 20:
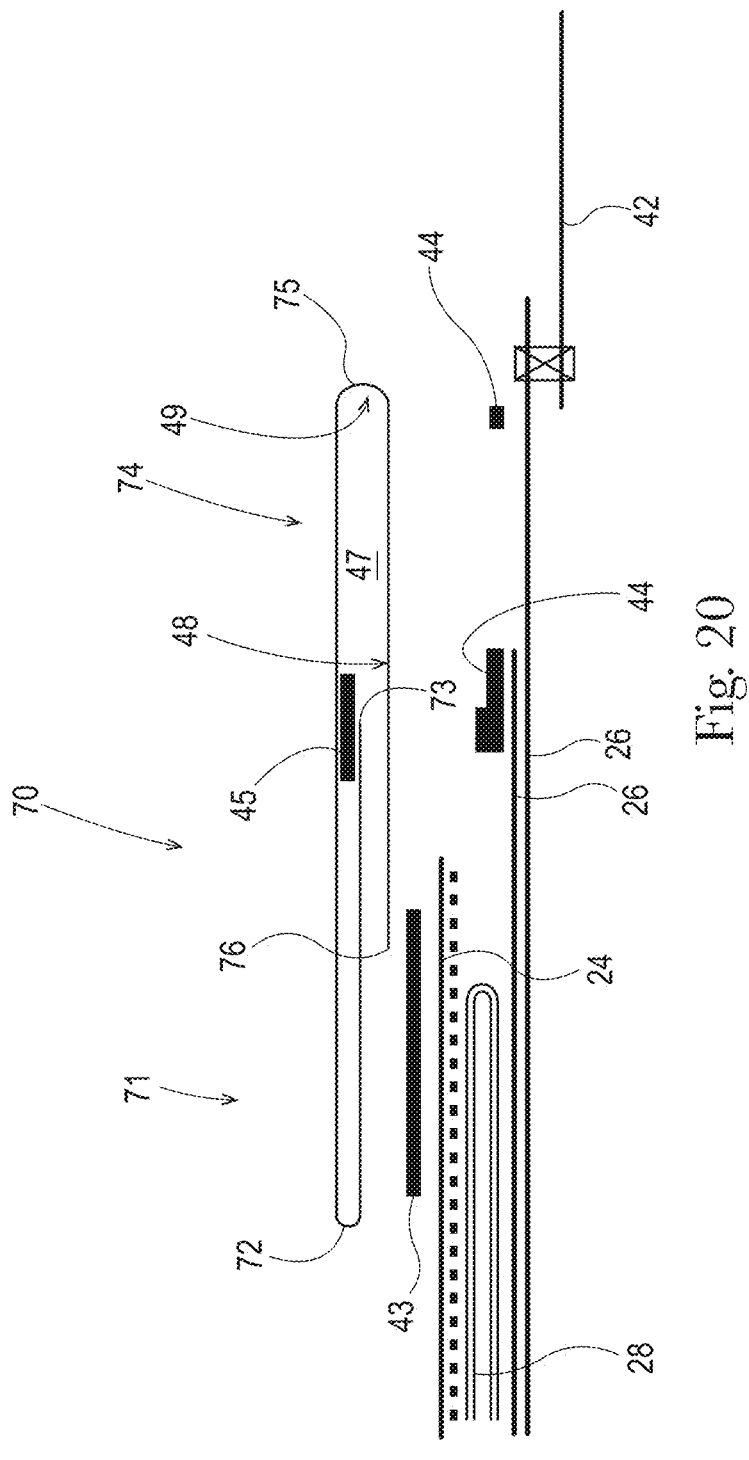
FIG. 20 is a schematic cross sectional view of an exemplary embodiment of the absorbent article of FIG. 1, the cross section taken along the line C-C.
Figure 21:
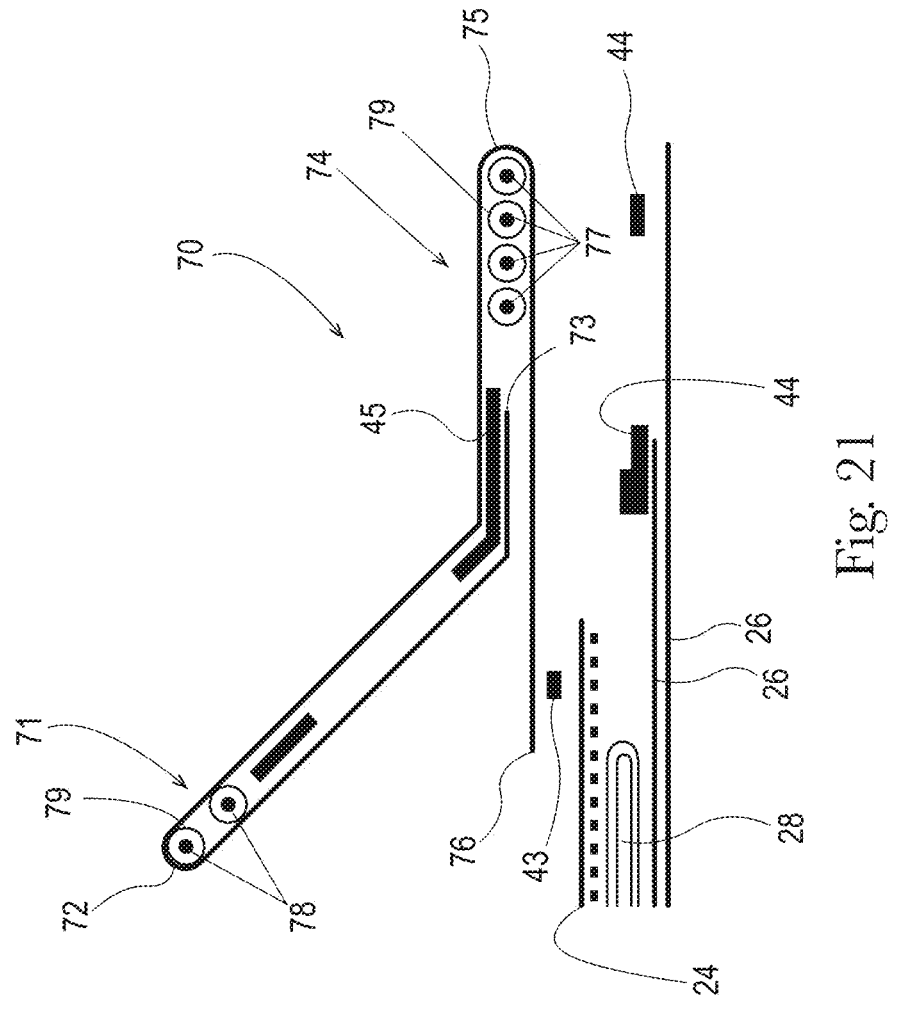
FIG. 21 is a schematic cross sectional view of an exemplary embodiment of the absorbent article of FIG. 1 with an opacity strengthening patch, the cross section taken along the line A-A.
Figure 22:
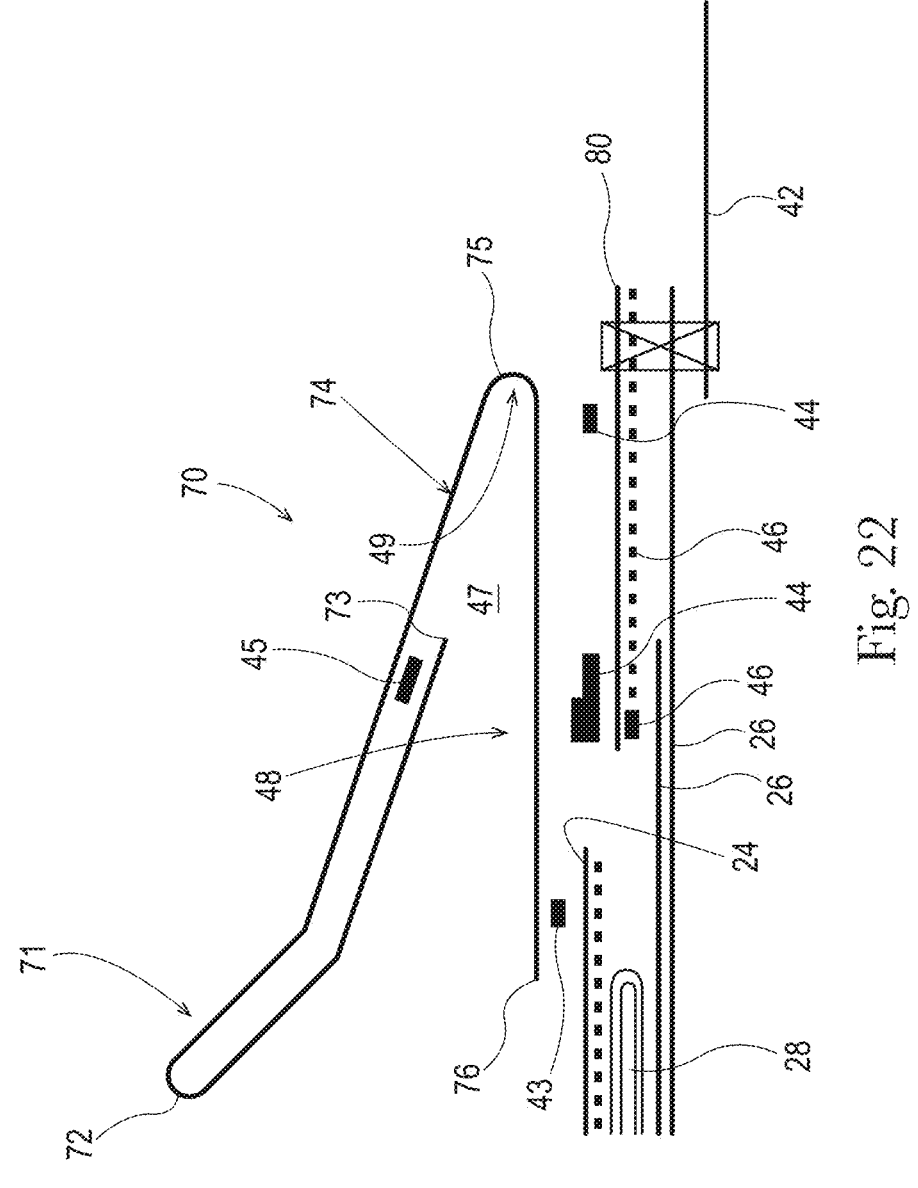
FIG. 22 is a schematic cross sectional view of an exemplary embodiment of the absorbent article of FIG. 1 with an opacity strengthening patch, the cross section taken along the line B-B.
Figure 23:
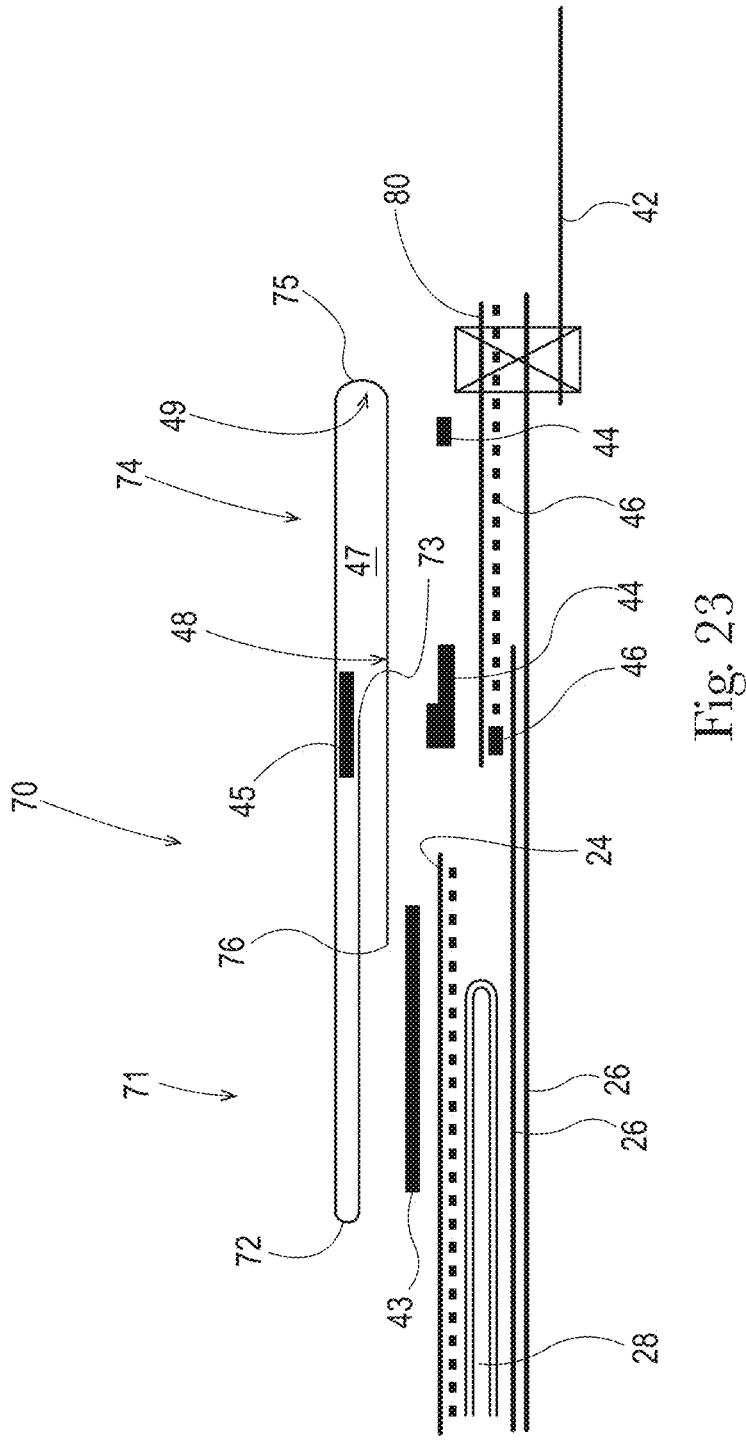
FIG. 23 is a schematic cross sectional view of an exemplary embodiment of the absorbent article of FIG. 1 with an opacity strengthening patch, the cross section taken along the line C-C.

In one embodiment, the outer cuff 74 comprises elastic members 77 positioned in a lateral array between the outer cuff folded edge 75 and outer cuff material edge 76. As illustrated in FIGS. 2-4, the elastics 77, 78 are attached to the portion of the web of material that forms the outer cuff by elastics adhesive 79. In such an embodiment, the elastics are positioned between 1) the portion of the web of material between the outer cuff folded edge 75 and the outer cuff material edge 76, and 2) the portion of the web material between the outer cuff folded edge 75 and the inner cuff folded edge 72. The outer cuff 74 may comprise at least two elastic members 77, at least three elastic members 77, at least four elastic members 77, at least five elastic members 77, or at least six elastic members 77. In one embodiment, the elastic members 77 may be disposed between the outer cuff folded edge 75 and the inner cuff material edge 73.

In one embodiment, the inner cuff 71 comprises an array of elastic members 78 positioned in a lateral array between the inner cuff folded edge 72 and the inner cuff material edge 73. The elastics attached to the portion of the web of material that forms the inner cuff by elastics adhesive 79. In such an embodiment, the elastics are positioned between 1) the portion of the web of material between the inner cuff folded edge 72 and the inner cuff material edge 73, and 2) the portion of the web material between the inner cuff folded edge 72 and the outer cuff folded edge 75. The inner barrier leg cuff 71 may comprise at least one elastic member 78, at least two elastic members 78, at least three elastic members 78, at least four elastic members 78, or at least five elastic members 78. In one embodiment, the elastic members 78 may be disposed between the inner cuff folded edge 72 and the outer cuff material edge 76.

In one embodiment, the outer cuff 74 comprises at least one more elastic member 77 than the inner cuff 71 elastic member(s) 78. In one embodiment, the inner cuff material edge 73 is laterally outboard the outer cuff material edge 76.

In one embodiment, the elastic members 77 and 78 are spaced at least 2 mm apart from one edge of the member to the other edge of the member, optionally at least 3 mm apart; optionally at least 3.5 mm apart; optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. In one embodiment, the outermost elastic members 77 and 78 are less than about 2 mm from the outer cuff material edge 76 and inner cuff material edge 73; optionally less than about 1.5 mm, less than about 1 mm.

In one embodiment, the outer cuff 74 has four elastic members 77 that are about 4 mm apart. The outer cuff 74 may have four elastic members that are about 2 mm/7 mm/2 mm apart. The outer cuff 74 may have three elastic members 77 that are about 6 mm apart. The outer cuff 74 may have two elastic members that are about 12 mm apart. The outer cuff 74 may have two elastic members that are about 3 mm/6 mm/3 mm apart, as spaced from the outer cuff folded edge 75. In any embodiment, the elastic members may be about 2 mm from the outer cuff folded edge 75, optionally about 0 mm from the outer cuff folded edge 75.

In one embodiment, the leg gasketing system 70 has an inner cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner cuff 71 and a second material comprising the outer cuff 74. The first and second material may overlap and be joined together along a longitudinal edge of each material by any suitable bonding means (i.e., a single web), or be separate webs of material. In one embodiment, the web of material is folded laterally inward to form the outer cuff folded edge 75 and folded laterally outward to form the inner cuff folded edge 72. In one embodiment, the proximal edges of the outer cuff 74 are coterminous. In one embodiment, the proximal edges of the outer cuff 74 are spaced greater than about 2 mm apart; greater than about 4 mm; greater than about 6 mm; greater than about 10 mm apart. In one embodiment, the proximal material edges of the cuff are both bonded to the inner cuff. In one embodiment, only one of the proximal material edges of the outer cuff 74 are bonded to the inner cuff. In one embodiment, the proximal material edges of the outer cuff are held together with any suitable bonding means.

In one embodiment, the leg gasketing system 70 is spaced laterally inward of the chassis longitudinal edge 12 by about 10 mm, optionally about 20 mm, optionally about 30 mm, optionally about 60 mm or more. In another embodiment, the laterally outboard edge of the chassis is defined by the lateral edge of the outer cuff. In another embodiment, the backsheet and/or polymeric film are spaced laterally inward of the outer cuff edge by about 10 mm; optionally about 20 mm; optionally about 30 mm; optionally about 40 mm.

In one embodiment, the laterally outboard edge of the leg gasketing system 70 is disposed laterally inboard of at least a portion of the longitudinal edge of the article in at least one of the waist regions. Thus, in one embodiment, the front ears 40 and/or back ears 42 extend past the leg gasketing system 70.

In one embodiment, the height of the inner cuff 71 is at least about 10 mm, at least about 20 mm, a least about 30 mm, at least about 32 mm, at least about 35 mm, at least about 38 mm. In one embodiment, the height of the outer cuff 74 is at least about 15 mm, at least about 23 mm, at least about 25 mm, at least about 27 mm, at least about 30 mm. The height of the inner cuff is measured from the inner cuff folded edge 72 to an inboard edge of the cuff separation bond 45 in the crotch region. The outer cuff height is measured from the outer cuff folded edge 75 to the outboard edge of the cuff separation bond 45 in the crotch region. Thus, the inner and outer cuffs are measured from their respective folded edges to the point where the inner cuff is connected to the first material beyond the inner cuff material edge.

One advantage of the leg gasketing system 70 detailed herein is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

In one embodiment of the absorbent articles detailed herein, the backsheet polymeric film is less than about 50 mm wider than the absorbent core; optionally less than about 40 mm wider, less than about 30 mm wider. In one embodiment, the backsheet polymeric film is at least about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

In one embodiment of the absorbent articles detailed herein, the leg cuff is joined to the topsheet and/or backsheet by a slot coated adhesive. In one embodiment, at least about 12 gsm of adhesive is applied; optionally at least about 15 gsm of adhesive is applied; optionally at least about gsm of adhesive is applied; optionally, at least about 25 gsm of adhesive is applied; optionally at least about 40 gsm of adhesive is applied; optionally at least about 60 gsm of adhesive is applied. In one embodiment, the adhesive is at least about 1 mm wide; optionally at least about 3 mm wide; optionally at least about 7 mm wide. In one embodiment, the adhesive is at least about 2 mm inboard of the outboard lateral edge of the film; optionally at least 4 mm inboard of the outboard lateral edge of the film; optionally at least about 6 mm inboard of the outboard lateral edge of the film. In one embodiment, the leg cuff is joined to the topsheet and/or backsheet by two overlapping and redundant spiral adhesive sprays; optionally three overlapping and redundant spiral adhesive sprays.

In another embodiment, the descriptions of the invention including the pocket 47 and opening 51 that allow for trapping exudates can be used in conjunction with an article that does not contain an absorbent core. This is useful for a product that is designed to be used in the medical industry as it can enable the collection of exudates for analysis easier without the exudates being absorbed into the product.

Additional embodiments of exemplary leg gasketing systems 70 that are be useful in the absorbent articles detailed herein are shown in FIGS. 11a-11t of the accompanying drawings.

Figure 25:
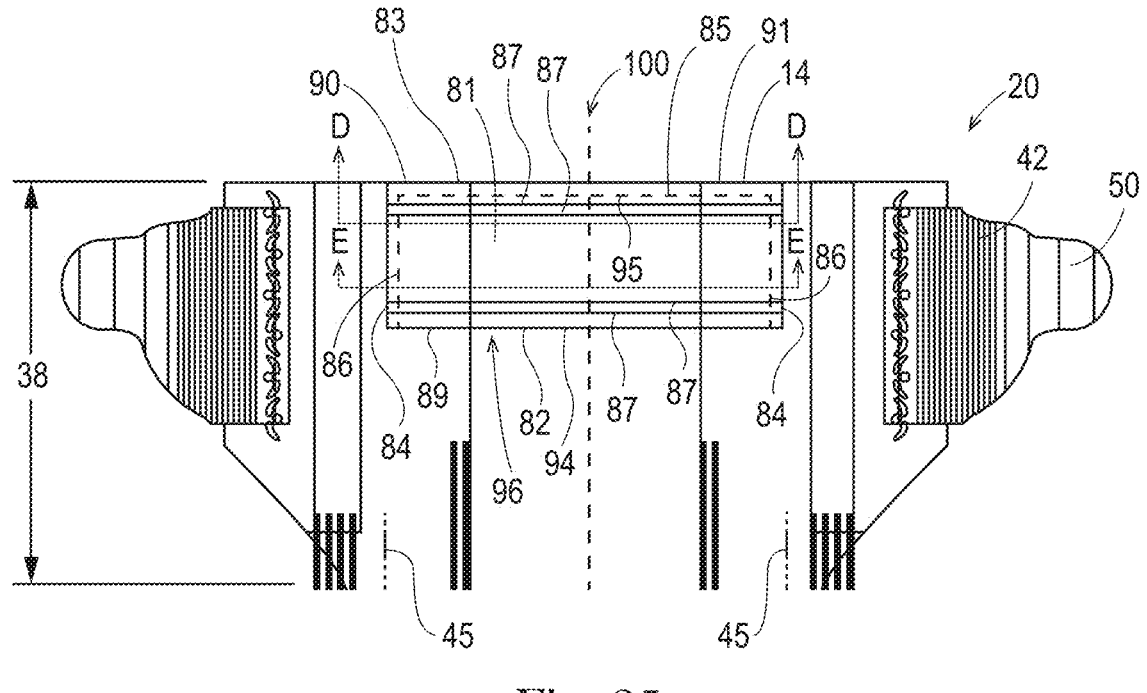
FIG. 25 is a close-up schematic plan view of the second waist region of the exemplary embodiment of the absorbent article depicted in FIG. 24.
Figure 26:
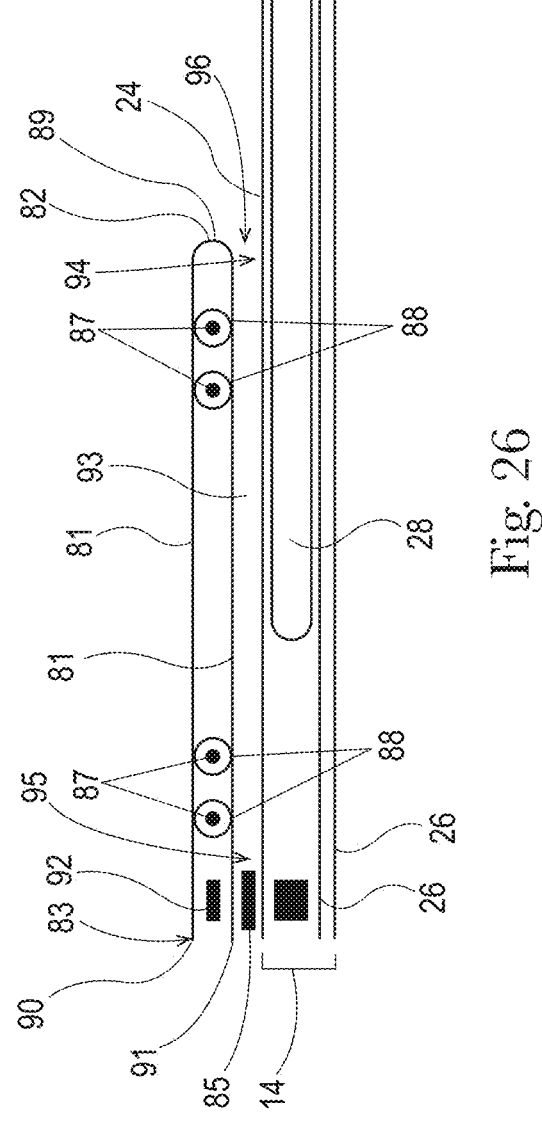
FIG. 26 is a schematic cross sectional view of an exemplary embodiment of the absorbent article of FIG. 25, the cross section taken along the longitudinal centerline.
Figure 27:
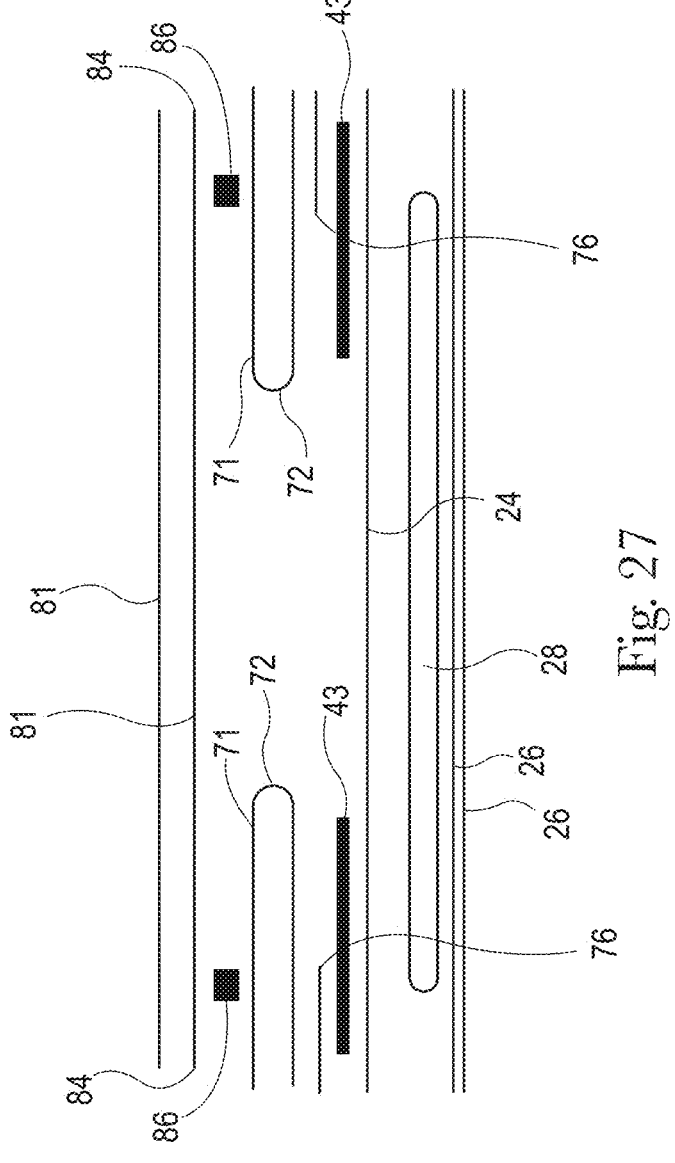
FIG. 27 is a schematic cross sectional view of an exemplary embodiment of the absorbent article of FIG. 25, the cross section taken along the line D-D.
Figure 28:
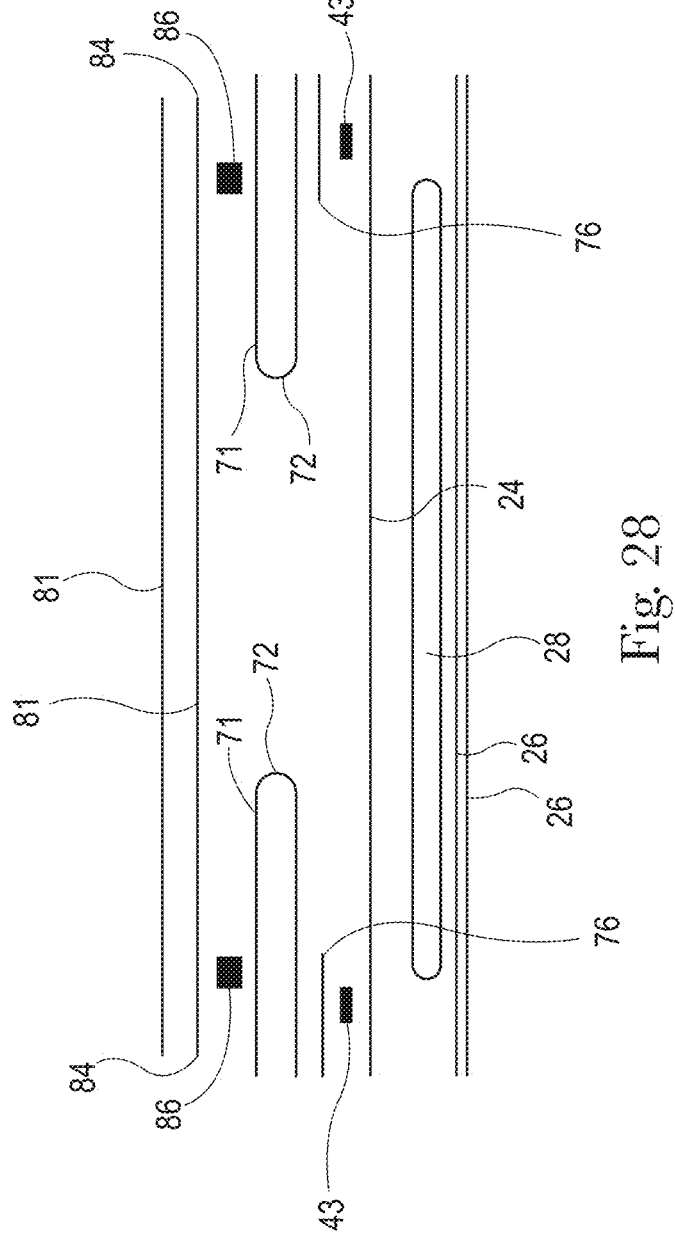
FIG. 28 is a schematic cross sectional view of an exemplary embodiment of the absorbent article of FIG. 25, the cross section taken along the line E-E.
Figure 29:
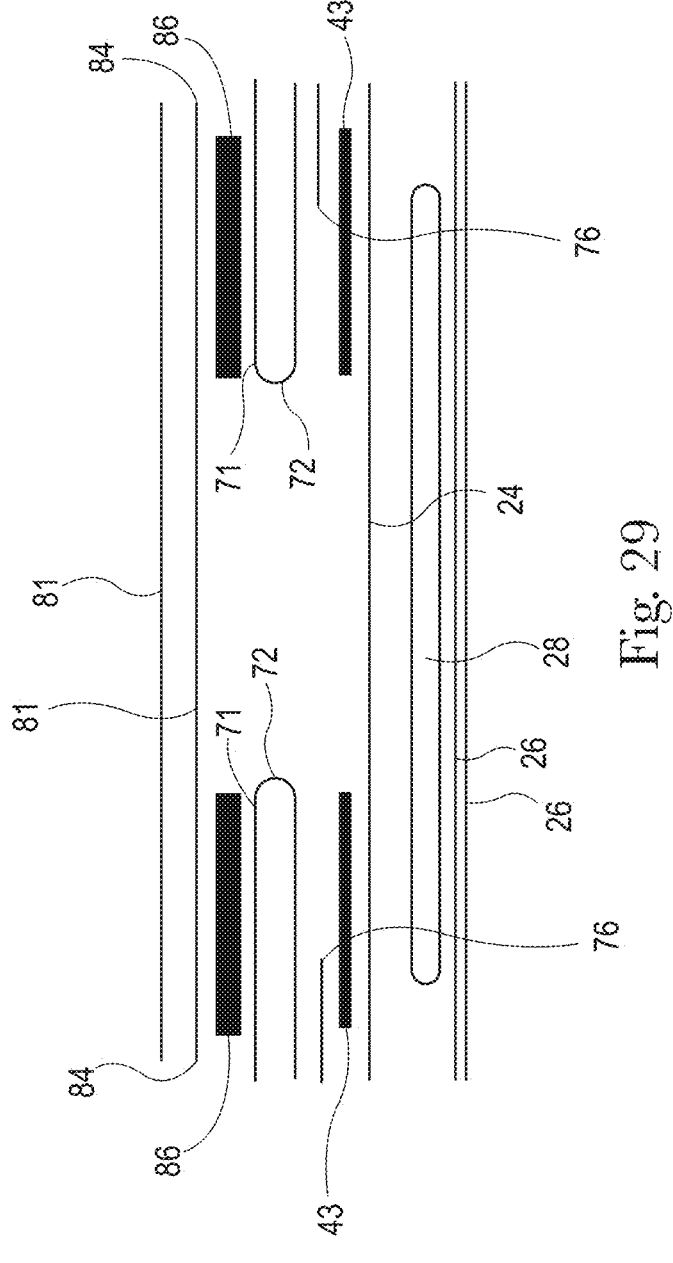
FIG. 29 is a schematic cross sectional view of an exemplary embodiment of the absorbent article of FIG. 25, the cross section taken along the line D-D.
Figure 30:
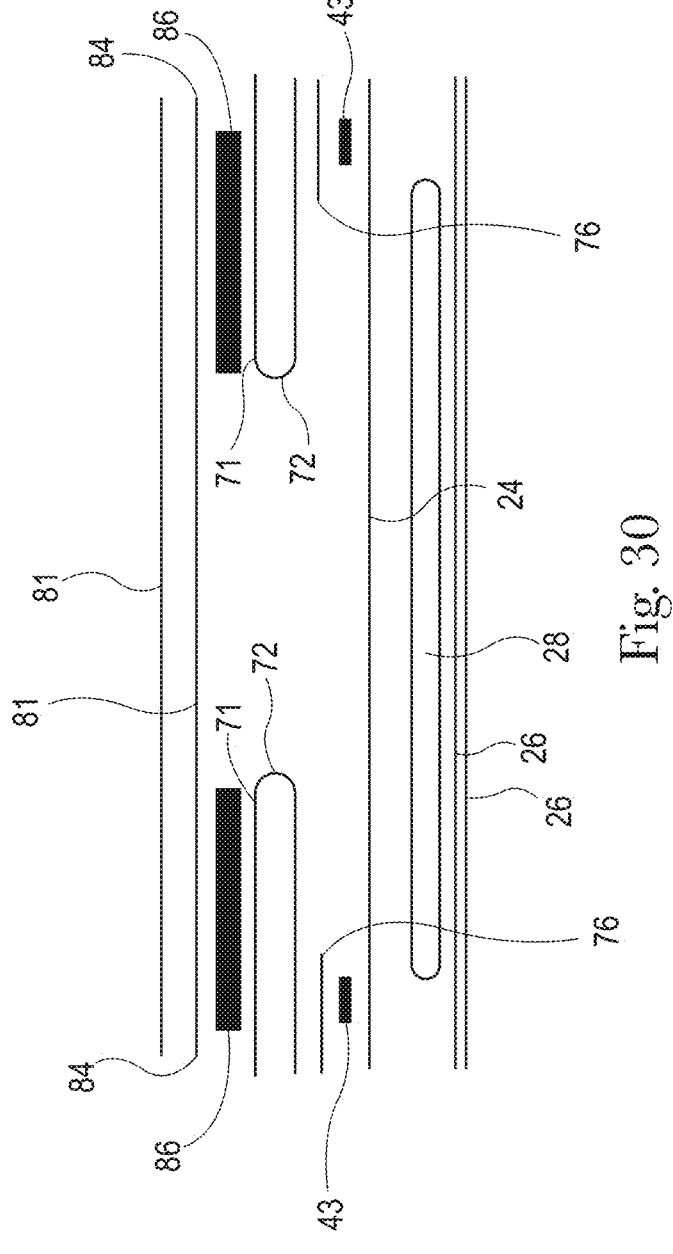
FIG. 30 is a schematic cross sectional view of an exemplary embodiment of the absorbent article of FIG. 25, the cross section taken along the line E-E.

Waist Gasketing Element:

The disposable absorbent article 20 may include at least one waist gasketing element 81 that is attached to both the chassis 22 and the leg gasketing system 70. FIG. 24 is a schematic view of an embodiment of the disposable absorbent article 20 as detailed herein that includes a waist gasketing element 81 in the second waist region 38. FIG. 25 is a close-up schematic view of the second waist region 38 of FIG. 24. FIG. 26 depicts a schematic cross sectional view of the exemplary second waist region 38 of FIG. 25 in a flat, uncontracted state, the view taken through the longitudinal centerline 100. FIGS. 27-30 also depict schematic cross sectional views of the second waist region 38 of FIG. 25. FIGS. 27 and 29 are schematic cross sectional views through line D-D of FIG. 25. FIGS. 28 and 30 are schematic cross sectional views through line E-E of FIG. 25.

In one embodiment, the at least one waist gasketing element 81 comprises a single, continuous web of material. An embodiment having a single web of material may provide a cost advantage over embodiments having more than one web of material. Further, a waist gasketing element formed from one web of material may have fewer leaks, as there are no holes created by bonding more than one web of material. Also, an embodiment having one web of material may be more aesthetically pleasing, as few mechanical bonds are visible. In other embodiments, the waist gasketing element(s) 81 may be formed from more than one web of material (e.g., multiple webs of material that are joined together to become one web of material, or multiple distinct webs of material that are separate from the disposable absorbent article chassis and form part of the waist gasketing element). Herein, locations (e.g., folded edge, material edge, etc.) on the waist gasketing element 81 are detailed in reference to "a web of material" or "a portion of the web of material." The recitations of "a web of material" or "the web of material" refer to waist gasketing element embodiments that may be formed from a single, continuous web of material, multiple webs of material that are joined together to become one web of material, a single material that is folded to form multiple layers of the same material, a single material that is slit apart and rejoined together, or multiple distinct webs of material that are separate from the disposable absorbent article chassis and form part of the leg gasketing system. All such embodiments are contemplated.

In one embodiment, the waist gasketing element 81 includes an inboard lateral edge 82, an outboard lateral edge 83, and two longitudinal edges 84. In some embodiments, the web of material forming the waist gasketing element 81 is folded longitudinally outward (away from the lateral centerline 110 of the absorbent article 20) to form the inboard lateral edge 82. In such embodiments, the inboard lateral edge 82 is also the location of the waist gasketing element folded edge 89 and the outboard lateral edge 83 is also the location of the waist gasketing element first material edge 90 and the waist gasketing element second material edge 91. Although an embodiment depicting a waist gasketing element 81 with one folded edge 89 and two material edges 90, 91 is shown in FIGS. 24-30, alternate constructions of useful waist gasketing elements are contemplated. For example, an alternate waist gasketing element 81 may include two distinct webs of material and therefore have four material edges (two on the inboard lateral edge 82, and two on the outboard lateral edge 83). As another example, an alternate waist gasketing element may have a continuous web material that is formed into having two folded edges (one on the inboard lateral edge 82, and one on the outboard lateral edge 83) and two material edges.

Further, the waist gasketing element 81 is attached to: 1) the chassis 22 of the disposable absorbent article 20 and 2) the leg gasketing system 70, such that at least a portion of the outboard lateral edge 83 of the waist gasketing element 81 is attached to the chassis 22 and at least a portion of the outboard lateral edge 83 of the waist gasketing element 81 is attached to the web of material of the leg gasketing system 70; and wherein the inboard lateral edge 82 of the waist gasketing element 81 is unattached to the chassis 22 of the disposable absorbent article 20. In embodiments that include a waist gasketing element 81 that has a waist gasketing element folded edge 89, a waist gasketing element first material edge 90, and a waist gasketing element second material edge 91, at least a portion of the web of material between the waist gasketing element folded edge 89 and waist gasketing element second material edge 91 is attached to the topsheet 24 and/or backsheet 26 of the chassis 22. The attachment of the waist gasketing element 81 to the chassis 22 is made through utilization of one or more outboard lateral edge bonds 85. As seen in the embodiment of FIGS. 24-26, the outboard lateral edge bond 85 attaches at least a portion of the waist gasketing element's web of material between the waist gasketing element folded edge 89 and the waist gasketing element second material edge 91 to the topsheet 24. In one embodiment, the attachment bond 85 is at the second waist edge 14 of the chassis 22; in other embodiments, the attachment bond is placed at least 2 mm inboard from the waist edge of the chassis; at least 10 mm inboard from the waist edge of the chassis; at least 20 mm inboard from the waist edge of the chassis; at least 50 mm inboard from the waist edge of the chassis; or any range or distance within the range of about 2 mm to about 50 mm inboard from the waist edge of the chassis. The outboard lateral edge bond 85 may take the form of glue, heat bond, pressure bond, CPW bonds, or any other bonding method known in the art. In the exemplary embodiments of FIGS. 24-26, the outboard lateral edge bond 85 takes the form of a glue bond, thermal bond or compression bond.

In embodiments that include a waist gasketing element 81 that has a waist gasketing element folded edge 89, a waist gasketing element first material edge 90, and a waist gasketing element second material edge 91, at least a portion of the web of material between the waist gasketing element folded edge 89 and waist gasketing element second material edge 91 is attached to the web of material forming the leg gasketing system 70. The attachment of the waist gasketing element 81 to the web of material forming the leg gasketing system 70 is made through utilization of one or more longitudinal edge bond(s) 86. As seen in the embodiment of FIGS. 24-30, the longitudinal edge bonds 86 attach at least a portion of the waist gasketing element's web of material between the waist gasketing element folded edge 89 and the waist gasketing element second material edge 91 to the web of material forming the leg gasketing system 70. In the embodiment illustrated in FIGS. 27-28, the longitudinal edge bonds 86 are located adjacent to the longitudinal edges 84 of the waist gasketing element 81 (or may be coterminous therewith). In another embodiment (not illustrated), the longitudinal edge bonds 86 are located adjacent to the inner cuff folded edge 72 of the leg gasketing system 70 (or may be coterminous therewith). In the embodiment illustrated in FIGS. 29-30, the longitudinal edge bonds 86 are wider than in the embodiment of FIGS. 27-28, and span the distance between 1) the longitudinal edges 84 of the waist gasketing element 81 and 2) the inner cuff folded edge 72 of the leg gasketing system 70. In other words, specifically regarding the longitudinal edge bonds 86 for the embodiment shown in FIGS. 29-30, the waist gasketing element 81 is attached to the leg gasketing system 70 over substantially the entire area that the leg gasketing system 70 overlaps with the waist gasketing element 81. In some embodiments, the waist gasketing element 81 is attached to the leg gasketing system 70 over more than about 50%, more than about 60%, more than about 70%, more than about 80%, more than about 90%, or more than about 95%, of the entire area that the leg gasketing system 70 overlaps with the waist gasketing element 81. The longitudinal edge bonds 86 may take the form of glue, heat bond, pressure bond, CPW bonds, or any other bonding method known in the art. In the exemplary embodiments of FIGS. 24-30, the longitudinal edge bonds 86 take the form of a glue bond, thermal bond or compression bond.

In some embodiments, the portion of the web material between the waist gasketing element folded edge 89 and the waist gasketing element first material edge 90 is attached to the portion of the web material between the waist gasketing element folded edge 89 and the waist gasketing element second material edge 91 by at least one waist gasketing element bond 92. In the embodiment illustrated in FIGS. 24-26, the waist gasketing element bond 92 is located adjacent to the waist gasketing element first material edge 90 and the waist gasketing element second material edge 91 (waist gasketing element bond 92 may also be coterminous with the waist gasketing element second material edge 91). The waist gasketing element bond 92 may take the form of glue, heat bond, pressure bond, CPW bonds, or any other bonding method known in the art. In the exemplary embodiments of FIGS. 24-26, the waist gasketing element bond 92 takes the form of a glue bond.

As illustrated in FIGS. 24-30, the inboard lateral edge 82 of the waist gasketing element 81 is unattached to the chassis 22 of the disposable absorbent article 20. Due to the waist gasketing element 81 being unattached to the chassis 22, a waist gasketing element pocket 93 is formed. The waist gasketing element pocket 93 is illustrated in FIG. 26. The waist gasketing element pocket 93 includes an inboard lateral edge 94 and an outboard lateral edge 95, which define the longitudinal length dimension of the waist gasketing element pocket 93. In some embodiments, the inboard lateral edge 94 of the waist gasketing element pocket 93 is coterminous with the waist gasketing element folded edge 89. In some embodiments, the outboard lateral edge 95 of the waist gasketing element pocket 93 is coterminous with the outboard lateral edge bond 85. In another embodiment, the outboard lateral edge 95 is coterminous with the most outboard bond of the waist gasketing element 81. The waist gasketing element pocket 93 includes an opening 96 which runs a distance along the inboard lateral edge 94 of the waist gasketing element pocket 93.

For the embodiment shown in FIG. 25, the overall longitudinal length of the waist gasketing element pocket 93 is the distance from the waist gasketing element folded edge 89 of the waist gasketing element pocket to the outboard lateral edge bond 85. In other words, for the exemplary embodiment shown in FIG. 25, the longitudinal dimensions of the waist gasketing element pocket 93 are defined by the waist gasketing element folded edge 89 and the outboard lateral edge bond 85. In one embodiment, the overall longitudinal length of the waist gasketing element pocket 93 measures between about 5 mm and about 100 mm in the longitudinal direction, or any range or distance within the range of about 5 mm to about 100 mm; in some embodiments, about 60 mm, about 40 mm, or about 35 mm; and in other embodiments the overall longitudinal length measures between about 1 mm and about 30 mm.

For the embodiment shown in FIG. 25, the overall lateral width of the waist gasketing element 81 is the distance from the longitudinal edge 84 of one side of the waist gasketing element 81 to the longitudinal edge 84 of the other side of the waist gasketing element. In one embodiment, the overall lateral width of the waist gasketing element 81 measures between about 60 mm and about 200 mm in the lateral direction, or any range or distance within the range of about 60 mm to about 200 mm; in some embodiments, about 60 mm, about 100 mm, or about 150 mm; and in other embodiments the overall lateral width measures between about 50 mm and about 300 mm.

When a wearer of an absorbent article has a runny bowel movement, many times the runny bowel movement spreads upon defecation and leaks out of the absorbent article in an area between the waist region and the wearer's back. Leaks of this type often happen because the snug fit between user's body and the attached absorbent article do not allow enough room for the runny bowel movement to remain contained within the absorbent article during the wearer's movement. One advantage of the waist gasketing element 81 detailed herein, in combination with the leg gasketing system(s) as detailed herein, are the additional pocketed areas (47 and 93) that provide extra void volumes within the leg cuffs and waist region for containment of bodily extrudate (e.g., fecal material). When the wearer moves, a portion of the bodily extrudate will migrate into the waist gasketing element pocket 93 for containment and be held/trapped between two layers of nonwoven before it can leak out in an area between the wearer's back and the back waist region of the absorbent article. Thus, the waist gasketing element 81 detailed herein reduces leaks. Moreover, the waist gasketing element pocket 93 provides additional void volume within the waist region to receive the fecal material which helps in isolating the fecal material from wearer's skin.

Further, the waist gasketing element pocket 93 may work in conjunction with the leg gasketing system pocket 47 to provide even more void volume within the absorbent article to receive fecal material and/or provide an easier path for fecal material to find the leg gasketing system pocket opening 51. The gasketing action of any elastic material (e.g., leg elastics 87, detailed below) within the waist gasketing element 81 may function to lift the inboard lateral edge 82 of the waist gasketing element 81 away from the chassis 22 of the absorbent article. The longitudinal edge bonds 86 of the waist gasketing element 81 attach the waist gasketing element to the inner cuff 71 and/or the outer cuff 74 of the leg gasketing system 70. Accordingly, the gasketing action of any elastic material (e.g., leg elastics 87) within the waist gasketing element 81 may also function to lift the inner cuff 71 and/or outer cuff 74 of the leg gasketing system 70 away from the chassis 22, therefore amplifying the opening 51 of the leg gasketing system pocket 51. With the opening 51 of the leg gasketing system pocket 51 opened up, the pocket can more readily accept fecal material.

While not being bound by theory, it is believed that the waist gasketing element 81 can provide a seal to the body which is created by multiple aspects of the invention. First, the waist gasketing element 81 is elasticated and designed to be under tension in use. The tension in use is created by the caregiver in the process of applying the product as she/he is trying to achieve a snug fit. Through the Capstan effect, the tension created during application and the radius of the body provides a force between the waist gasketing element and the body which is in the normal direction with respect to the body. This normal force between the waist gasketing element 81 and the body provides the initial seal that causes bodily extrudate to run between the waist gasketing element 81 and the chassis or topsheet, and causes the bodily extrudate to be forced into the waist gasketing element pocket 93. Furthermore, it is known that rapidly excreted bodily extrudate has a pressure which causes the distribution of the bodily extrudate throughout the absorbent article 20. If the bodily extrudate is trapped between the waist gasketing element 81 and the chassis 22, then the pressure created from the bodily extrudate will act to further seal the waist gasketing element 81 against the body, adding to the normal force created by the aforementioned Capstan effect and creating an even better seal. Since the waist gasketing element 81 is sealed to the body, bodily extrudate can't escape and then an amount of the bodily extrudate is forced laterally sideways into the leg gasketing system pocket 47 for storage.

To achieve the maximum effectiveness from the Capstan effect, which leads to the sealing of the waist gasketing element 81 to the body, the leg gasketing system should ideally be positioned in an area of the body which has a continuous convex surface or a continuous cylindrical shape or approximation thereof. If the body surface becomes concave or "valley-like" at any point, the waist gasketing element 81 will not be able to form a proper seal between the body and the waist gasketing element. This will allow exudates to escape through the space between the body and the waist gasketing element 81. Therefore, it important to position the waist gasketing element 81 above the gluteal groove, in such a way as to ensure that the body has the right geometry to enable the seal to be adequately formed. Ideally, the waist gasketing element 81 can be positioned at the top of the gluteal groove, 10 mm above the gluteal grove, 25 mm above the gluteal groove, or 50 mm above the gluteal groove.

In addition, it may be useful to make the waist gasketing element 81 tall enough so that if the chassis 22 does not fit close to the body, the waist gasketing element can still remain in contact. Additionally, it may be useful to provide enough void volume in the waist gasketing element pocket 93 such that sufficient amounts of bodily extrudate can reside there. To ensure that the waist gasketing element 81 is sufficiently above the gluteal groove and also is tall enough to seal to the body and create enough void volume, it is advantageous to position the waist gasketing element at the top of the absorbent article 20, near or coincident to the waist edge 13, 14, or as close as possible to the waist edge. With variability in the placement of the materials in high speed diaper making applications, it may be necessary to position the waist gasketing element 81 in such a way as to enable it to be cut apart as a part of the manufacturing process such that a portion of the waist gasketing element 81 is attached to a first absorbent article and the remainder is attached to the next absorbent article in the manufacturing process. This ensures that the top edge of the waist gasketing element 81 is coterminous to the waist edge 13, 14. Thus, the waist gasketing element 81 is not spaced down from the waist edge of the absorbent article. In other embodiments, the outboard lateral edge 83 of the waist gasketing element 81 is placed 5 mm inboard of the second waist edge 14 of chassis 22; whereas in some embodiments, the outboard lateral edge 83 of the waist gasketing element is placed at least 10 mm inboard from the waist edge 13, 14 of the chassis 22; at least 20 mm inboard from the waist edge of the chassis; at least 50 mm inboard from the waist edge of the chassis; or any range or distance within the range of about 2 mm to about 100 mm inboard from the waist edge of the chassis.

In some embodiments, the waist gasketing element pocket 93 includes a thermal or compression bond that defines at least a portion of the perimeter of the pocket (e.g., the entire perimeter of the pocket), such that the at least a portion of the pocket 93 (e.g., the entire pocket), can be made visible to a wearer or caregiver as to signal the functionality of the pocket 93 prior to use.

In yet another embodiment, the waist gasketing element pocket 93 includes a glue or bond that defines at least a portion of the perimeter of the pocket (e.g., the entire perimeter of the pocket), such that the at least a portion of the pocket 93 (e.g., the entire pocket), can be made visible to a wearer or caregiver as to signal the functionality of the pocket 93 prior to use.

In another embodiment, the hydrophobic properties, such as Low Surface Tension Strikethrough or Hydro Head, can be increased in a least a portion of the waist gasketing element 81, or in the whole waist gasketing element, in such a way that prevents exudates from leaking through the materials that comprise the waist gasketing element. Accordingly, this will maintain separation of the contained fecal material from the wearer. Increasing hydrophobic properties can be accomplished by applying hydrophobic coatings, inks, glues, silicones, additional materials, or any combination thereof, or by any other means known in the art. Additionally, it may be advantageous to include an N-fiber material in the waist gasketing element to provide the similar benefits as associated with the leg cuff, as detailed herein.

In one embodiment, the waist gasketing element 81 and the leg gasketing system 70 are the same color. In one embodiment, the waist gasketing element 81 and the leg gasketing system 70 are different colors. In one embodiment, there is an additional printing on the waist gasketing element 81.

In another embodiment, the waist gasketing element 81 includes a printed zone that outlines or defines at least a portion of the waist gasketing element pocket 93 such that the benefit can be signaled prior to use.

In one embodiment, the waist gasketing element 81 includes elastic members 87 positioned in a longitudinal array between the inboard lateral edge 82 and the outboard lateral edge 83 of waist gasketing element 81. As illustrated in FIG. 26, the elastics 87 are attached to the portion of the web of material that forms the waist gasketing element 81 by elastics adhesive 88. In such an embodiment, the elastics are positioned between 1) the portion of the web of material between the waist gasketing element folded edge 89 and the waist gasketing element first material edge 90, and 2) the portion of the web material between the waist gasketing element folded edge 89 and the waist gasketing element second material edge 91. The waist gasketing element 81 may comprise at least two elastic members 87, at least three elastic members 87, at least four elastic members 87, at least five elastic members 87, at least six elastic members 87, at least seven elastic members 87, at least eight elastic members 87, at least nine elastic members 87, at least ten elastic members 87, at least eleven elastic members, or at least twelve elastic members 87.

In one embodiment, the elastic members 87 are spaced at least 2 mm apart from one edge of the member to the other edge of the member; optionally at least 3 mm apart; optionally at least 3.5 mm apart; optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. In one embodiment, the most inboard elastic members 87 are less than about 2 mm from the waist gasketing element folded edge 89; optionally less than about 1.5 mm, less than about 1 mm. In one embodiment, the most outboard elastic members 87 are less than about 2 mm from the outboard lateral edge 83; optionally less than about 1.5 mm, less than about 1 mm.

In one embodiment, the waist gasketing element 81 has four elastic members 87 that are each about 4 mm apart. The waist gasketing element 81 may have four elastic members that are about 2 mm/7 mm/2 mm apart. The waist gasketing element 81 may have five elastic members that are about 6.5 mm/7.5 mm/9 mm/11 mm apart. The waist gasketing element 81 may have three elastic members 77 that are each about 6 mm apart. The waist gasketing element 81 may have two elastic members that are about 12 mm apart. The waist gasketing element 81 may have four elastic members that are about 3 mm/6 mm/10 mm/20 mm/30 mm spaced from the inboard lateral edge 82. In some embodiments, the elastic members may be about 2 mm from the inboard lateral edge 82, or about 0 mm from the outer inboard lateral edge 82 (or be disposed directly adjacent the inboard folded edge 89).

In one embodiment, the elastic members 87 have a prestrain level of at least 50%; optionally at least 95%; optionally at least 150%; optionally at least 200%; optionally at least 250%; optionally at least 300%; optionally at least 350%; or any range distance within the range of about 50% to about 350%. The prestrain level is the amount of strain put on the elastics before the elastic is glued down with elastics adhesive to the waist gasketing element 81 web of material. In some embodiments, the prestrain level of each elastic member 87 can be identical, in other embodiments, the prestrain levels can be different from elastic to elastic. In one preferred embodiment, the prestrain of elastic member(s) proximate the inboard lateral edge 82 can be higher than the prestrain level of the elastic member(s) proximate the outboard lateral edge 90. In this preferred embodiment, the contraction level of the inboard lateral edge 82 is greater than the contraction level of the outboard lateral edge 90.

In one embodiment, the waist gasketing element 81 has ability to elongate in lateral direction from its relaxed state by at least 15 mm, by 35 mm, 40 mm, 50 mm, 60 mm, 70 mm, 80 mm, or even up to 100 mm; or any range or distance within the range of about 15 mm to about 100 mm.

In one embodiment, the decitex (g/mm) type can be different from elastic to elastic in the waist gasketing element 81. In one preferred embodiment, the decitex (g/mm) of elastic member(s) proximate the inboard lateral edge 82 can be higher than the decitex (g/mm) of the elastic member(s) proximate the outboard lateral edge 90. In this embodiment the contractive forces proximate to the lateral inboard edge 82 are higher than the contractive forces in the lateral outboard edge 90.

The waist gasketing element 81 may be attached to the chassis 22 and the leg gasketing system 70 when the elastics 87 of the waist gasketing element are only partially extended, but the chassis of the absorbent article 20 is fully extended. In addition, in one embodiment, the waist gasketing element 81 may be fully extended when the corresponding waist region is fully extended in the lateral direction. In another embodiment, the waist gasketing element may not be fully extended when the corresponding waist region is fully extended. In other words, in some embodiments, at least some gathers in the web material of the waist gasketing element 81 are still present when attaching the waist gasketing element 81 to the chassis 22 and the leg gasketing system 70, while the materials of the chassis are fully extended. Once attached, the elastics 87 of the waist gasketing element 81 may retract from their state of partial extension to a relaxed state. Attaching the waist gasketing element 81 to the chassis 22 in this way allows the waist gasketing element 81 to be only partially extended when the waist region of the absorbent article is fully extended in use. In other words, in some embodiments, when a user fully extends the waist region of the disposable absorbent article 20, at least some gathers in the web material of the waist gasketing element 81 are still present.

Although the waist gasketing element 81 described herein has be only specifically detailed as being located in the second waist region 38, in some embodiments the waist gasketing element may be present in the first waist region 36. In some embodiments, a waist gasketing element 81 as detailed herein may be included in both the first waist region 36 and the second waist region 38. For instance, a wearer who sleeps on their belly (front) may benefit from the waist gasketing element 81 being located in the front waist region 36, as to stop urine leakage out of the front waist during sleep. As with the waist gasketing element located in the rear waist region, a waist gasketing element in the front waist region (i.e., first waist region 36) can also work in conjunction with a leg gasketing system pocket for the storage of urine as needed to prevent leakage out of the front of the product.

Opacity Strengthening Patch:

In some embodiments of the disposable absorbent articles detailed herein, an opacity strengthening patch 80 may be included as part of the chassis 22. The opacity strengthening patch 80 is an additional layer of material. The opacity strengthening patch 80 may be connected to the leg gasketing system 70, the polymeric film layer, and/or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 and/or the polymeric film layer (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 22 where strength and opacity is desirable. Materials suitable to act as the opacity strengthening patch include materials having a basis weight of at least about 10 gsm, at least about gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

In one embodiment, the opacity strengthening patch 80 is discrete and is located in the front and back waist regions of the article. In one embodiment, the opacity strengthening patch is about 70 mm long in the front, optionally about 90 mm long in the front; optionally about 120 mm long in the front. In one embodiment, the opacity strengthening patch is about 70 mm long in the back, optionally about 100 mm long in the back, optionally about 140 mm long in the back. In one embodiment, the opacity strengthening patch is continuous and spans the entire length of the product.

In one embodiment, the opacity strengthening patch has a hunter color opacity of greater than about 15%, optionally greater than about 25%, optionally greater than about 40%, optionally greater than 60%.

In one embodiment the opacity strengthening patch is laterally outboard of the polymeric film layer. In one embodiment, the opacity strengthening patch overlaps the polymeric film layer in the lateral direction such that it can be affixed to the polymeric film in order to transmit laterally directed application and wearing forces from the opacity strengthening patch to the polymeric film layer. Any suitable bonding means known in the art may be used to affix the opacity strengthening patch to the polymeric film layer. In one embodiment, the opacity strengthening patch overlaps the polymeric film layer by about 5 mm, optionally about 10 mm, optionally about 15 mm, optionally about 20 mm, optionally less than about 30 mm.

In one embodiment, there is a lateral gap between the opacity strengthening patch and the polymeric film layer and the opacity strengthening patch is affixed by any suitable bonding means to the leg gasketing system, and the leg gasketing system is affixed to the polymeric film layer by any suitable bonding means such that application and wearing loads can transmit from the opacity strengthening patch to the gasketing system and then from the gasketing system to the polymeric film layer. In this embodiment, the gap is preferably less than 30 mm, more preferably less than 20 mm, more preferably less than 10 mm.

In one embodiment, there is a lateral gap between the opacity strengthening patch and the polymeric film layer; the opacity strengthening patch may be affixed by any suitable bonding means to the leg gasketing system and the body facing and garment facing sides of the leg gasketing system may be affixed together by any suitable bonding means so that the loads from the opacity strengthening patch are shared by both layers of the leg gasketing system. The leg gasketing system may be affixed to the polymeric film layer by any suitable bonding means such that application and wearing loads can transmit from the opacity strengthening patch to the leg gasketing system and then from the leg gasketing system to the polymeric film layer.

In one embodiment, the opacity strengthening patch overlaps the leg gasketing system in the lateral direction such that it can be affixed securely to the opacity strengthening patch layer by any suitable bonding means as a way to transmit application and wearing forces from the opacity strengthening patch to the leg gasketing system. In this embodiment, the opacity strengthening patch may overlap the leg gasketing system by about 5 mm, optionally about 10 mm, optionally less than about 15 mm, optionally less than about 25 mm.

In one embodiment the leg gasketing system has about the same lateral tensile strength properties as the opacity strengthening patch. In one embodiment the combined properties of the leg gasketing system and the backsheet non-woven outer cover has about the same lateral tensile strength as the opacity strengthening patch. In another embodiment the outercover nonwoven has very low lateral strength between about 0% and about 10% engineering strain. In one embodiment, the outercover nonwoven may exhibit the following tensile properties: at 10% engineering strain for a 1 inch wide sample, 0.4N.

Construction Materials:

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

In one embodiment, the inner cuff 71 web of material has a hydrostatic head of greater than about 2 mbar, greater than about 3 mbar, greater than about 4 mbar. In one embodiment, the outer cuff 74 web of material has a hydrostatic head of less than about 200 mbar, less than about 100 mbar, less than about 75 mbar, less than about 50 mbar, less than about 25 mbar, less than about 15 mbar.

In one embodiment, the folded outer cuff web of material has a basis weight of 10 gsm; optionally 13 gsm; optionally 15 gsm; optionally 18 gsm.

In one embodiment, the inner cuff 71 web of material has an opacity of from about 15% to about 50% hunter opacity; optionally from about 20% to about 45% hunter opacity. In one embodiment, the outer cuff 74 web of material has an opacity of from about 45% to about 75% hunter opacity; optionally from about 50% to about 70% hunter opacity; optionally less than about 75% hunter opacity; optionally less than about 70% hunter opacity.

In one embodiment, the inner cuff 71 web of material has an air permeability of less than about 50 $m^3/m^2/min$; optionally less than about 45 $m^3/m^2/min$. In one embodiment, the outer cuff 74 web of material has an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

In one embodiment, the inner cuff 71 web of material has a WVTR of less than about 5500 $g/m^2/24$ hrs; optionally less than about 5400 $g/m^2/24$ hrs. In one embodiment, the outer cuff 74 web of material has a WVTR of greater than about 4250 $g/m^2/24$ hrs; optionally greater than about 4500 $g/m^2/24$ hrs; optionally greater than about 5000 $g/m^2/24$ hrs; optionally greater than about 5250 $g/m^2/24$ hrs; optionally greater than about 5500 $g/m^2/24$ hrs.

The gasketing cuffs 70 may be substantially inelastic or may be elastically extensible to dynamically fit at the wearer's leg. The gasketing cuff 70 may be formed by one or more elastic members 77 and 78 (such as elastic strands) operatively joined to the topsheet 24, backsheet 26, or any other suitable substrate used in the formation of the absorbent article 20. Suitable gasketing cuff construction is further described in U.S. Pat. No. 3,860,003

The inner cuff 71 may span the entire longitudinal length of the absorbent article 20. The inner cuff 71 may be formed by a flap and an elastic member 78 (such as elastic strands). The inner cuff 71 may be a continuous extension of any of the existing materials or elements that form the absorbent article 20.

The inner cuff 71 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap may comprise a nonwoven web such as spunbond webs, meltblown webs, carded webs, and combinations thereof (e.g., spunbond-meltblown composites and variants). Laminates of the aforementioned substrates may also be used to form the flap. A particularly suitable flap may comprise a nonwoven available from BBA Fiberweb, Brentwood, TN as supplier code 30926. A particularly suitable elastic member is available from Invista, Wichita, KS as supplier code T262P. Further description of diapers having inner barrier cuffs and suitable construction of such barrier cuffs may be found in U.S. Pat. Nos. 4,808,178 and 4,909,803. The elastic member 78 may span the longitudinal length of the inner cuff 71. In other embodiments, the elastic member 78 may span at least the longitudinal length of the inner cuff 71 within the crotch region 37. It is desirable that the elastic member 78 exhibits sufficient elasticity such that the inner cuff 71 remains in contact with the wearer during normal wear, thereby enhancing the barrier properties of the inner cuff 71. The elastic member 78 may be connected to the flap at opposing longitudinal ends. In certain embodiments, the flap may be folded over onto itself so as to encircle the elastic member 78.

The inner cuff 71 and/or outer cuff 74 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning MI, Salzburg as supplier code 0010024820.

EXAMPLES to the Y opacity procedure which prompts the operator to cover the sample with either the white or black calibration tile during the measurement.

Articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the

| Product | Lot No. | Opacity % | | Air Permeability m³/m²/min | | WVTR g/m²/24 hrs | | Hydrohead mbar | | 32 dyne Strikethrough Sec | |
|---|---|---|---|---|---|---|---|---|---|---|---|
| | | Outer Cuff | Inner Cuff | Outer Cuff | Inner Cuff | Outer Cuff | Inner Cuff | Outer Cuff | Inner Cuff | Outer Cuff | Inner Cuff |
| Prototype N-Fiber | NA | 58.7 ± 2.2 | 37.6 ± 3.2 | 26.8 ± 5.6 | 36.9 ± 4.6 | 5905 ± 129 | 5224 ± 87 | 16.8 ± 2.1 | 12.3 ± 1.3 | 21.0 ± 3.5 | 9.2 ± 1.5 |
| Prototype SMS | NA | 65.8 ± 1.8 | 39.0 ± 1.0 | 65.6 ± 11.5 | 38.5 ± 3.8 | 5748 ± 276 | 5193 ± 145 | 16.3 ± 1.8 | 10.0 ± 1.7 | 15.6 ± 1.9 | 7.6 ± 1.4 |
| Pampers BabyDry | 0089U011390422 | 80.1 ± 0.4 | 38.8 ± 3.8 | 2.1 ± 1.0 | 56.1 ± 6.3 | 4063 ± 67 | 5252 ± 157 | >200 | 6.7 ± 0.8 | >100 | 10.1 ± 0.5 |
| Luvs | 1047U011390518 | 85.3 ± 1.2 | 36.4 ± 3.4 | 3.1 ± 1.9 | 90.2 ± 9.3 | 304 ± 144 | 5244 ± 26 | >200 | 6.5 ± 1.0 | >100 | 11.8 ± 1.4 |
| Huggies Little Movers | BI006912B | 80.1 ± 1.0 | 45.4 ± 4.2 | 2.6 ± 0.4 | 45.0 ± 15.7 | 3673 ± 190 | 5581 ± 90 | >200 | 8.3 ± 1.3 | >100 | 14.3 ± 3.5 |
| Huggies Supreme | NM1275U1F0755 | 72.7 ± 2.2 | 53.6 ± 2.3 | 4.4 ± 1.1 | 145.2 ± 23.2 | 375 ± 77 | 5688 ± 85 | >200 | 9.2 ± 1.8 | >100 | 14.6 ± 3.1 |

\* Results are expressed as the average ± one standard deviation
\* Prototype N-Fiber is a 13 gsm SMNS available from Polymer Group Inc
\* Prototype SMS is a 15 gsm SMS (Spunbonded-Meltblown-Spunbonded) nonwoven available from Fibertex under the Comfort Line Test Methods Opacity Method Opacity is measured using a 0° illumination/45° detection, circumferential optical geometry, spectrophotometer with a computer interface such as the HunterLab LabScan XE running Universal Software (available from Hunter Associates Laboratory Inc., Reston, VA) or equivalent instrument. Instrument calibration and measurements are made using the standard white and black calibration plates provided by the vendor. All testing is performed in a room maintained at 23±2° C. and 50±2% relative humidity.

The spectrophotometer is conFIG.d for the XYZ color scale, D65 illuminant, 10° standard observer, with UV filter set to nominal. The instrument is standardized according to the manufacturer's procedures using the 0.7 inch port size and 0.5 inch area view. After calibration, the software is set black standard tile without moving the specimen. A second reading is taken, and the opacity is calculated as follows:

$$\text{Opacity} = (Y \, \text{value}_{(black\ backing)} / Y \, \text{value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2 C.° and 50%±2% relative humidity.

Articles are preconditioned at 23° C.±2 C.° and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens from the cuffs on the right side of the article are prepared.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Carr (cat. No. 4591K11) or equivalent. The Teflon tape is applied up to the top edge of the vial but should not cover any portion of the vial's opening. The mass of the vial assembly (vial+specimen+sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

$$\text{WVTR}(g/m^2/24 \text{ hrs})=([\text{starting mass}(g)-\text{final mass}(g)]/\text{surface area}(m^2))/24 \text{ hrs}$$

Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m²/24 hrs.

Air Permeability Test

Air permeability is tested using a TexTest FX3300 Air Permeability Tester (available from Advanced Testing Instruments, Greer, SC) with a custom made 1 cm² circular aperture (also available from Advanced Testing Instruments) or equivalent instrument. The instrument is calibrated according to the manufacturer's procedures. All testing is performed in a room maintained at 23° C.±2 C.° and 50%±2% relative humidity.

The articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m³/m²/min.

Hydrostatic Head Test

Hydrostatic head is tested using a TexTest FX3000 Hydrostatic Head Tester (available from Advanced Testing Instruments, Greer, SC) with a custom made 1.5 cm² circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2 C.° and about 50%±2% relative humidity.

Precondition the articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strike-through time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, OH 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2 C.° and about 50%±2% relative humidity. The Ahlstrom filter paper and test articles are conditioned in this controlled environment for 24 hours and 2 hours before testing.

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer. Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises:

a topsheet;

a backsheet; and an absorbent core disposed between the topsheet and the backsheet;

a leg gasketing system and at least one waist gasketing element;

wherein the leg gasketing system comprises a web of material forming an inner cuff and an outer cuff;

wherein the inner cuff comprises an inner cuff folded edge and an inner cuff material edge and the outer cuff comprises an outer cuff material edge, such that the web of material is folded laterally outward to form the inner cuff folded edge;

wherein at least a portion of the web of material between the inner cuff folded edge and the outer cuff material edge is attached to the topsheet in the first waist region, the second waist region and the crotch region;

a waist gasketing element comprising an inboard lateral edge, an outboard lateral edge, and two longitudinal edges; wherein the waist gasketing element further comprises a continuous web material formed to comprise a waist gasketing element first material edge, a waist gasketing element second material edge, and a waist gasketing element folded edge, wherein in the waist gasketing element folded edge defines the inboard lateral edge, wherein the waist gasketing element first material edge is attached to the continuous web of material between the waist gasketing element folded edge and the waist gasketing element second material edge by at least one waist gasketing element bond, and wherein at least a portion of the web of material between the waist gasketing element folded edge and waist gasketing element second material edge is attached to the topsheet;

elastic strands bonded with the continuous web of material;

wherein waist gasketing element is connected with the topsheet and the leg gasketing system, such that at least a portion of the outboard lateral edge of the waist gasketing element is attached to the topsheet and at least a portion of the outboard lateral edge of the waist gasketing element is attached to the web of material forming the leg gasketing system; and wherein the inboard lateral edge of the waist gasketing element is unattached to the topsheet to form a waist gasketing element pocket; and wherein at least a portion of the inboard lateral edge of the waist gasketing element is attached to the leg gasketing system.

2. The disposable absorbent article of claim 1, wherein the waist gasketing element further comprising two inboard elastic strands adjacent the inboard edge and separated from each other by about 6 mm, and two outboard elastic strands adjacent the outboard edge separated from each other by about 6 mm.

3. The disposable absorbent article of claim 2, wherein a prestrain level of elastic strands proximate the inboard lateral edge is higher than a prestrain level of elastic strands proximate the outboard lateral edge.

4. The disposable absorbent article of claim 2, wherein a decitex of elastic strands proximate the inboard lateral edge is higher than a decitex of elastic strands proximate the outboard lateral edge.

5. The disposable absorbent article of claim 2, wherein the absorbent core extends longitudinally between the two inboard elastic strands and the two outboard elastic strands such that the inboard elastic strands extend laterally across the absorbent core and the two outboard elastic strands do not extend laterally across the absorbent core.

6. The disposable absorbent article of claim 1, wherein the outboard lateral edge of the waist gasketing element is coterminous with the second waist edge of the disposable absorbent article.

7. The disposable absorbent article of claim 1, wherein the outboard lateral edge of the waist gasketing element is inboard of the second waist edge of the disposable absorbent article.

8. The disposable absorbent article of claim 1, wherein at least a portion of each of the two longitudinal edges of the waist gasketing element are attached to the leg gasketing system.

9. The disposable absorbent article of claim 1, wherein an entire length of each of the two longitudinal edges of the waist gasketing element are attached to the leg gasketing system.

10. The disposable absorbent article of claim 1, wherein the waist gasketing element is attached to leg gasketing system over substantially an entire area that the leg gasketing system overlaps with the waist gasketing element.

11. The disposable absorbent article of claim 1, wherein the elastic strands of the waist gasketing element are only partially extended when the respective waist region is fully extended.

12. The disposable absorbent article of claim 1, wherein the at least one of the leg gasketing system and the at least one waist gasketing element comprises an N-fiber material.

13. The disposable absorbent article of claim 1, wherein the disposable absorbent article is a pant-type diaper.

14. The disposable absorbent article of claim 1, wherein the waist gasketing element pocket defines a longitudinal length between about 1 mm to about 30 mm.

15. The disposable absorbent article of claim 1, wherein the absorbent core is substantially cellulose free.

16. The disposable absorbent article of claim 1, wherein the waist gasketing element second material edge defines the outboard board lateral edge.

17. The disposable absorbent article of claim 1, wherein the waist gasketing element bond is coterminous with the waist gasketing element second material edge.

\* \* \* \* \*